United States Patent [19]

Ishikawa et al.

[11] Patent Number: 5,496,928
[45] Date of Patent: Mar. 5, 1996

[54] ENDOTHELIN ANTAGONISTIC SUBSTANCE

[75] Inventors: Kiyofumi Ishikawa; Takehiro Fukami; Takashi Hayama; Kenji Niiyama; Toshio Nagase; Toshiaki Mase; Kagari Fujita; Masaki Ihara; Fumihiko Ikemoto; Mitsuo Yano; Masaru Nishikibe, all of Tsukuba, Japan

[73] Assignee: Banyu Pharmaceutical Co., Ltd., Tokyo, Japan

[21] Appl. No.: 230,534

[22] Filed: Apr. 20, 1994

Related U.S. Application Data

[63] Continuation of Ser. No. 981,424, Nov. 25, 1992, abandoned, which is a continuation-in-part of Ser. No. 945,414, Sep. 16, 1992, which is a continuation-in-part of Ser. No. 884,642, May 18, 1992, abandoned, which is a division of Ser. No. 712,095, Jun. 7, 1991, abandoned.

[30] Foreign Application Priority Data

| Jun. 7, 1990 | [JP] | Japan | 1-149105 |
| Dec. 4, 1991 | [JP] | Japan | 2-347670 |
| Dec. 18, 1991 | [JP] | Japan | 2-353738 |
| Aug. 10, 1992 | [JP] | Japan | 3-234207 |

[51] Int. Cl.$^6$ ............................... A61K 38/06
[52] U.S. Cl. ..................... 530/331; 548/496; 562/575
[58] Field of Search ............... 514/18, 19; 530/331; 548/496; 562/575

[56] References Cited

U.S. PATENT DOCUMENTS

| 3,872,074 | 3/1975 | Konig | 260/112.5 |
| 5,114,918 | 5/1992 | Ishikawa et al. | 514/11 |

FOREIGN PATENT DOCUMENTS

| 76446/91 | 11/1991 | Australia | C07K 5/08 |
| 0457195 | 11/1991 | European Pat. Off. | |
| 0460679 | 12/1991 | European Pat. Off. | |
| WO93/10144 | 5/1993 | WIPO | |

*Primary Examiner*—Jill Warden
*Assistant Examiner*—David Lukton
*Attorney, Agent, or Firm*—Oblon, Spivak, McClelland, Maier & Neustadt

[57] ABSTRACT

Peptides having the formula:

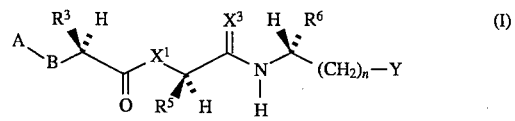

inhibit the binding of endothelin and are useful in treating diseases associated with excess production or secretion of endothelin.

6 Claims, 2 Drawing Sheets

ENDOTHELIN ANTAGONISTIC SUBSTANCE

This application is a CONTINUATION of application Ser. No. 07/981,424 filed Nov. 25, 1992, now abandoned, which is a Continuation-in-Part of Ser. No. 07/945,414 filed Sep. 16, 1992, which is a Continuation-in-Part of Ser. No. 07/884,642 filed May 18, 1992, now abandoned, which is a Division of Ser. No. 07/712,095 filed Jun. 7, 1991, now abandoned.

The present invention relates to novel compounds having antagonism against three endothelin isopeptides (endothelin-1, endothelin-2 and endothelin-3), which are physiologically highly active endogenous peptides, processes for their preparation and their use as a drug.

Two endothelin receptor subtypes $ET_A$ and $ET_B$ are known so far. The compounds of the present invention possess high affinity to at least the $ET_B$ receptors, thereby inhibiting vasoconstriction and bronchoconstriction induced by the endothelins. The compounds of the present invention provide a new therapeutic potential, particularly for the treatment of hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, endotoxin shock, endotoxin-induced multiple organ failure or disseminated intravascular coagulation, and/or cyclosporin-induced renal failure or hypertension.

Endothelin is a polypeptide composed of 21 amino acids, and it is produced by vascular endothelial cells of human or pig. Endothelin has a potent vasoconstrictor effect and a sustained and potent pressor action (Nature, 332, 411–415 (1988)).

Three endothelin isopeptides (endothelin-1, endothelin-2 and endothelin-3), which resemble one another in structure, exist in the bodies of animals including human, and these peptides have vasoconstriction and pressor effects (Proc. Natl. Acad, Sci, USA, 86, 2863–2867 (1989)).

As reported, the endothelin levels are clearly elevated in the blood of patients with essential hypertension, acute myocardial infarction, pulmonary hypertension, Raynaud's disease, diabetes or atherosclerosis, or in the washing fluids of the respiratory tract or the blood of patients with asthmaticus as compared with normal levels (Japan, J. Hypertension, 12, 79, (1989), J. Vascular Medicine Biology, 2, 207 (1990), Diabetologia, 33, 306–310 (1990), J. Am. Med. Association, 264, 2868 (1990), and The Lancet, ii, 747–748 (1989) and ii, 1144–1147 (1990)).

Further, an increased sensitivity of the cerebral blood vessel to endothelin in an experimental model of cerebral vasospasm (Japan. Soc. Cereb. Blood Flow & Metabol., 1, 73 (1989)), an improved renal function by the endothelin antibody in an acute renal failure model (J. Clin, Invest., 83, 1762–1767 (1989), and inhibition of gastric ulcer development with an endothelin antibody in a gastric ulcer model (Extract of Japanese Society of Experimental Gastric Ulcer, 50 (1991)) have been reported. Therefore, endothelin is assumed to be one of mediators causing acute renal failure or cerebral vasospasm following subarachnoid hemorrhage.

Further, endothelin is secreted not only by endothelial cells but also by tracheal epithelial cells or from kidney cells (FEBS Letters, 255, 129–132 (1989), and FEBS Letters, 249, 42–46 (1989)).

Endothelin was also found to control the release of physiologically active endogenous substances such as renin, atrial natriuretic peptide, endothelium-derived relaxing factor (EDRF), thromboxane $A_2$, prostacyclin, noradrenaline, angiotensin II and substance P (Biochem. Biophys, Res. Commun., 157, 1164–1168 (1988); Biochem. Biophys, Res. Commun., 155, 167–172 (1989); Proc. Natl. Acad. Sci. USA, 85, 9797–9800 (1989); J. Cardiovasc. Pharmacol., 13, S89–S92 (1989); Japan. J. Hypertension, 12, 76 (1989) and Neuroscience Letters, 102, 179–184 (1989)). Further, endothelin causes contraction of the smooth muscle of gastrointestinal tract and the uterine smooth muscle (FEBS Letters, 247, 337–340 (1989); Eur. J. Pharmacol., 154, 227–228 (1988); and Biochem. Biophys. Res. Commun., 159, 317–323 (1989)). Further, endothelin was found to promote proliferation of rat vascular smooth muscle cells, suggesting a possible relevance to the arterial hypertrophy (Atherosclerosis, 78, 225–228 (1989)). Furthermore, since the endothelin receptors are present in a high density not only in the peripheral tissues but also in the central nervous system, and the cerebral administration of endothelin induces a behavioral change in animals, endothelin is likely to play an important role for controlling nervous functions (Neuroscience Letters, 97, 276–279 (1989)). Particularly, endothelin is suggested to be one of mediators for pain (Life Sciences, 49, PL61–PL65 (1991)).

On the other hand, endotoxin is one of potential candidates to promote the release of endothelin. Remarkable elevation of the endothelin levels in the blood or in the culture supernatant of endothelial cells was observed when endotoxin was exogenously administered to animals or added to the culture endothelial cells, respectively. These findings suggest that endothelin is one of important mediators for endotoxin-induced diseases (Biochem. Biophys. Res. Commun., 161, 1220–1227 (1989); and Acta Physiol. Scand., 137, 317–318 (1989)).

Further, it was reported that cyclosporin remarkably increased endothelin secretion in the renal cell culture (LLC-PK1 cells) (Eur. J. Pharmacol., 180, 191–192 (1990)). Further, dosing of cyclosporin to rats reduced the glomerular filtration rate and increased the blood pressure in association with a remarkable increase in the circulating endothelin level. This cyclosporin-induced renal failure can be suppressed by the administration of endothelin antibody (Kidney Int., 37, 1487–1491 (1990)). Thus, it is assumed that endothelin is significantly involved in the pathogenesis of the cyclosporin-induced diseases.

Such various effects of endothelin are caused by the binding of endothelin to endothelin receptors widely distributed in many tissues (Am. J. Physiol., 256, R856–R866 (1989)).

It is known that vasoconstriction by the endothelins is caused via at least two subtypes of endothelin receptors (J. Cardiovasc. Pharmacol., 17(Suppl.7), S119–S121 (1991)). One of endothelin receptors is $ET_A$ receptor selective to ET-1 rather than ET-3, and the other is $ET_B$ receptor equally active to ET-1 and ET-3. These receptor proteins are reported to be different from each other (Nature, 348, 730–735 (1990)).

These two subtypes of endothelin receptors are differently distributed in tissues. It is known that the $ET_A$ receptor is present mainly in cardiovascular tissues, whereas the $ET_B$ receptor is widely distributed in various tissues such as brain, kidney, lung, heart and vascular tissues.

Substances which specifically inhibit the binding of endothelin to the endothelin receptors are believed to antagonize various pharmacological activities of endothelin and to be useful as a drug in a wide field. The present inventors already disclosed potent endothelin $ET_A$ receptor antagonists in EP 0460679A2. Since, the action of the endothelins is caused via not only the $ET_A$ receptor but also the $ET_B$ receptor, novel substances with $ET_B$ receptor antagonistic activity are desired to block activities of the endothelins in various diseases.

Endothelin is an endogenous substance which directly or indirectly (by controlling liberation of various endogenous substances) induces sustained contraction of vascular or non-vascular smooth muscles, and its excess production or excess secretion is believed to be one of pathogeneses for hypertension, pulmonary hypertension, Raynaud's disease, bronchial asthma, gastric ulcer, diabetes, arteriosclerosis, acute renal failure, myocardial infarction, angina pectoris, cerebral vasospasm and cerebral infarction. Further, it is suggested that endothelin serves as an important mediator involved in disease such as endotoxin shock, endotoxin-induced multiple organ failure or disseminated intravascular coagulation, and/or cyclosporin-induced renal failure or hypertension. Two endothelin receptors $ET_A$ and $ET_B$ are known so far. An antagonistic agent against the $ET_B$ receptor as well as the $ET_A$ receptor is useful as a drug. Accordingly, it is an object of the present invention to provide a novel therapeutics for the treatment of the above-mentioned various diseases by an invention of a potent $ET_B$ receptor antagonist.

In order to accomplish the above object, the present inventors have synthesized various peptide derivatives and have investigated their endothelin antagonistic activities, and as a result have found that novel peptide derivatives represented by the following formula (I) and their pharmaceutically acceptable salts have strong potent $ET_B$ receptor antagonistic activities. The present invention has been accomplished on the basis of this discovery.

Thus, the present invention provides a peptide derivative of the formula:

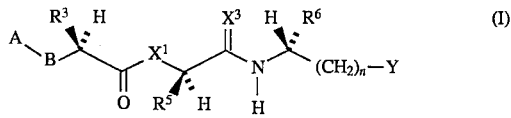

wherein A is a group of the formula $R^{11}O$—CO— (wherein $R^{11}$ is a lower alkyl group or a phenyl group), or a group of the formula $R^{12}R^{13}N$—C(=O)— (wherein $R^{12}$ is a lower alkyl group, a cycloalkyl group, a 1-adamantyl group, a phenyl group wherein one or two optional hydrogen atoms on the benzene ring may independently be replaced by a halogen atom, a trifluoromethyl group, a nitro group, an amino group or a formylamino group, a pyridyl group, or a thienyl group, $R^{13}$ is a hydrogen atom, a lower alkyl group or a cycloalkyl group, or R12 and $R^{13}$ form, together with the adjacent nitrogen atom, a 5- to 9-membered nitrogen-containing saturated heterocyclic ring having 4 to 8 carbon atoms, wherein among methylene groups forming the ring, one optional methylene group not adjacent to the above nitrogen atom may be replaced by a thio group, and one to four optional hydrogen atoms on the carbon atoms of the heterocyclic ring may independently be replaced by a lower alkyl group, and further two adjacent carbon atoms in the heterocyclic ring may form a benzo-fused ring); B is an oxygen atom or a group of the formula —$NR^2$— (wherein $R^2$ is a hydrogen atom or a lower alkyl group); $R^3$ is a lower alkyl group, a cycloalkyl group, an aryl group, a heterocyclic group, a cycloalkyl lower alkyl group, an aryl lower alkyl group or a heterocyclic lower alkyl group; $X^1$ is an oxygen atom or a group of the formula —$NR^4$— (wherein $R^4$ is a hydrogen atom or a lower alkyl group); $R^5$ is a 3-indolylmethyl, 3-benzothienylmethyl, 1-naphthylmethyl or benzyl group wherein one or two optional hydrogen atoms on the ring may be replaced by a hydroxyl group, a halogen atom, a formyl group, a lower alkyl group, a lower alkoxy group, a lower alkylthio group, a lower alkylsulfinyl group, a lower alkylsulfonyl group, a lower alkoxycarbonyl group, a nitro group or a group of the formula $R^{51}$—CO—$X^2$ {wherein $R^{51}$ is a lower alkyl group, a lower alkoxy group, or an amino group which may be substituted by a lower alkyl group, and $X^2$ is an oxygen atom or a group of the formula —$NR^{52}$— (wherein $R^{52}$ is a hydrogen atom or a lower alkyl group)}; $X^3$ is an oxygen atom or a sulfur atom; $R^6$ is a hydrogen atom, or a lower alkyl or lower alkenyl group which may have a substituent selected from the group consisting of a hydroxyl group, a lower alkoxy group, a lower alkylthio group and a heterocyclic group; n is 0 or 1; Y is a hydroxymethyl group, a group of the formula $CO_2R^{71}$ (wherein $R^{71}$ is a hydrogen atom or a lower alkyl group), a group of the formula $CONHR^{72}$ (wherein $R^{72}$ is a hydrogen atom or a lower alkyl group which may have a substituent selected from the group consisting of a hydroxyl group, a carboxyl group and a sulfo group), a 1H-tetrazol-5-yl group, a sulfo group and a phosphono group; or a pharmaceutically acceptable salt thereof.

Figure 1:
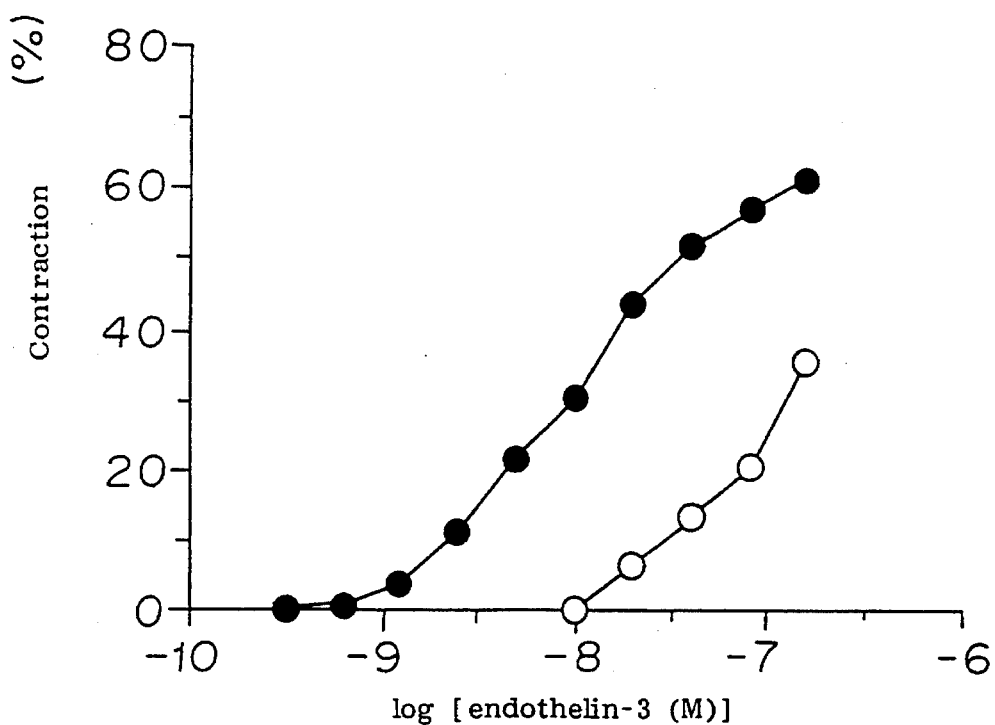
FIG. 1 shows the activities of 10 μM of Compound 4 (o) against endothelin-3-induced contraction of isolated guinea pig bronchial tube as compared with the case in which no drug is present (●).

Now, the present invention will be described in further detail with reference to the preferred embodiments.

Now, the meanings of various abbreviations used in this specification will be given.

| Abbreviation | Meaning of Abbreviation |
|---|---|
| DβAbu | D-3-aminobutyric acid |
| DBal | D-3-(3-benzothienyl)alanine |
| Ile | L-isoleucine |
| DIle | D-isoleucine |
| Leu | L-leucine |
| γMeLeu | γ-methyl-L-leucine |
| DMet | D-methionine |
| DNal | D-3-(1-naphthyl)alanine |
| Nle | L-norleucine |
| DNle | D-norleucine |
| Nva | L-norvaline |
| DNva | D-norvaline |
| DPhe(m-$NO_2$) | D-3-(3-nitrophenyl)alanine |
| DPhe(m-$NH_2$) | D-3-(3-aminophenyl)alanine |
| DLPhe(3-COOEt) | DL-3-(3-ethoxycarbonylphenyl)alanine |
| DLPhe(3-COOMe) | DL-3-(3-methoxycarbonylphenyl)alanine |
| DSer | D-serine |
| DSer(Me) | O-methyl-D-serine |
| D-mTyr | D-methatyrosine |
| DL-mTyr | DL-methatyrosine |
| DTrp | D-tryptophan |
| DTrp(7-OBzl) | D-(7-benzyloxy)tryptophan |
| DTrp(7-OH) | D-(7-hydroxy)tryptophan |
| DTrp(COOEt) | D-($N^{in}$-ethoxycarbonyl)tryptophan |
| DTrp(COOMe) | D-($N^{in}$-methoxycarbonyl)tryptophan |
| DTrp(OH) | D-($N^{in}$-hydroxy)tryptophan |
| DTrp(OMe) | D-($N^{in}$-methoxy)tryptophan |
| DLTrp(Me) | DL-($N^{in}$-methyl)tryptophan |
| DTrp(2-SMe) | D-(2-methylthio)tryptophan |
| DTrp(2-Br) | D-(2-bromo)tryptophan |

-continued

| Abbreviation | Meaning of Abbreviation |
|---|---|
| DTrp(2-Cl) | D-(2-chloro)tryptophan |
| DTrp(1-Me,2-Cl) | D-(2-chloro-1-methyl)tryptophan |
| Ac | acetyl |
| Boc | tert-butoxycarbonyl |
| Et | ethyl |
| Me | methyl |
| $n_{Pr}$ | n-propyl |
| $i_{Pr}$ | isopropyl |
| $n_{Bu}$ | n-butyl |
| $t_{Bu}$ | tert-butyl |
| Ph | phenyl |
| Bzl | benzyl |
| c-Pent | cyclopentyl |
| Cpeg | L-cyclopentylglycine |
| Cprg | L-cyclopropylglycine |
| CDI | 1,1'-carbonyldiimidazole |
| DCC | N,N'-dicyclohexylcarbodiimide |
| DMAP | 4-(dimethylamino)pyridine |
| DMF | N,N-dimethylformamide |
| DMSO | dimethylsulfoxide |
| NMP | N-methylpyrrolidone |
| NMM | N-methylmorpholine |
| EDCI.HCl | 1-ethyl-3-(3-dimethylaminopropyl)-carbodiimide.hydrochloride |
| HOBT.H$_2$O | 1-hydroxy-1H-benzotriazole.monohydrate |
| HOSu | N-hydroxysuccinimide |
| TBAHS | tetra-n-butylammonium hydrogensulfate |
| TEA | triethylamine |
| TFA | trifluoro acetic acid |
| THF | tetrahydrofuran |
| TsOH | p-toluene sulfonic acid |
| Ts | p-toluenesulfonyl |
| Z | benzyloxycarbonyl |
| MOPS | 3-morpholinopropane sulfonic acid |
| HEPES | 2-[4-(2-hydroxyethyl)-1-piperazinyl]-ethane sulfonic acid |
| Tris | tris(hydroxymethyl)aminomethane |
| PMSF | phenylmethanesulfonyl = fluoride |

Now, the definitions of the various terms mentioned in this specification will be explained.

In this specification, the lower alkyl group means a linear or branched alkyl group having 1 to 6 carbon atoms such as a methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl or 1-ethyl-1-methylpropyl group.

The cycloalkyl group may, for example, be a cyclopropyl, cyclobutyl, cyclopentyl, cyclohexyl, cycloheptyl, cyclooctyl or cyclononyl group.

The aryl group may, for example, be a phenyl, 1-naphthyl or 2-naphthyl group.

The heterocyclic group means a heterocyclic or fused heterocyclic group containing at least one hetero atom such as an oxygen, nitrogen or sulfur atom, for example, a thienyl, furyl, thiazolyl, imidazolyl, pyridyl, indolyl or benzothienyl group.

The lower alkenyl group means a linear or branched alkenyl group having 1 to 6 carbon atoms such as a vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 4-pentenyl or 5-pentenyl group.

The lower alkoxy group means a linear or branched alkoxy group having 1 to 6 carbon atoms such as a methoxy, ethoxy, propoxy or isopropoxy group.

The lower alkanoyloxy group means a linear or branched alkanoyloxy group having 2 to 6 carbon atoms such as an acetoxy or propionyloxy group.

The halogen atom means a fluorine, chlorine, bromine or iodine atom.

The lower alkylthio group means a linear or branched alkylthio group having 1 to 6 carbon atoms such as a methylthio, ethylthio, propylthio or isopropyl group. The lower alkylsulfinyl group means a linear or branched alkylsulfinyl group having 1 to 6 carbon atoms such as a methylsulfinyl, ethylsulfinyl, propylsulfinyl or isopropylsulfinyl group. The lower alkylsulfonyl group means a linear or branched alkylsulfonyl group having 1 to 6 carbon atoms such as a methylsulfonyl, ethylsulfonyl, propylsulfonyl or isopropylsulfonyl group.

Now, this invention will be described in more detail with reference to specific examples for the various symbols used in the formula (I).

In A, $R^{11}$ means a lower alkyl group or a phenyl group. Examples of the lower alkyl group are methyl, ethyl, propyl, isopropyl, butyl, isobutyl, sec-butyl, tert-butyl, pentyl, isopentyl, neopentyl, tert-pentyl, 1,1-dimethylbutyl, 1-ethyl-1-methylpropyl and 1,1,2-trimethylpropyl groups.

In A, $R^{12}$ means a lower alkyl group, a cycloalkyl group, a 1-adamantyl group, a phenyl group wherein 1 or 2 optional hydrogen atoms on the benzene ring may be replaced by an optional group selected from the group consisting of a halogen atom, a trifluoromethyl group, a nitro group, an amino group and a formylamino group, a pyridyl group or a thienyl group. Otherwise, $R^{12}$ and $R^{13}$ may form, together with the adjacent nitrogen atom, a heterocyclic group as indicated below. Examples of the lower alkyl group are methyl, ethyl, propyl, isopropyl, butyl, isobutyl, sec-butyl, tert-butyl, pentyl, isopentyl, neopentyl, tert-pentyl, 1,1-dimethylbutyl, 1-ethyl-1-methylpropyl and 1,1,2-trimethylpropyl groups. Examples of the cycloalkyl group are cyclopropyl, cyclobutyl, cyclopentyl, cyclohexyl and cycloheptyl groups. Examples of the phenyl group wherein 1 or 2 optional hydrogen atoms on the benzene ring may be replaced by an optional group selected from the group consisting of a halogen atom, a trifluoromethyl group, a nitro group, an amino group and a formylamino group, are phenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2,6-difluorophenyl, 2,6-dichlorophenyl, 2,6-dibromophenyl, 2-aminophenyl, 2-formylaminophenyl, 2-trifluoromethylphenyl, 2-nitrophenyl, 3-aminophenyl and 3-formylaminophenyl groups. Examples of the pyridyl group are 2-pyridyl, 3-pyridyl and 4-pyridyl groups. Examples of the thienyl group are 2-thienyl and 3-thienyl groups.

In A, $R^{13}$ means a hydrogen atom, a lower alkyl group or a cycloalkyl group. Otherwise, $R^{13}$ and $R^{12}$ may form, together with the adjacent nitrogen atom, a heterocyclic group as indicated below. Examples of the lower alkyl group are methyl, ethyl, propyl, isopropyl, butyl, isobutyl, sec-butyl, tert-butyl, pentyl, isopentyl, neopentyl and tert-pentyl groups. Examples of the cycloalkyl group are cyclopropyl, cyclobutyl, cyclopentyl, cyclohexyl and cycloheptyl groups.

In A, $R^{12}$ and $R^{13}$ may also form, together with the adjacent nitrogen atom, a 5- to 9-membered nitrogen-containing saturated heterocyclic group having 4 to 8 carbon atoms. Among methylene groups forming the heterocycle, one optional methylene group not adjacent to the above nitrogen atom may be replaced by a thio group, and one to four optional hydrogen atoms on the carbon atoms of the heterocycle may independently be replaced by a lower alkyl group, and further two adjacent carbon atoms in the heterocycle may form a fused-benzene ring. Examples of the heterocyclic group are pyrrolidino, piperidino, perhydroazepin-1-yl, perhydroazocin-1-yl, perhydroazonin-1-yl, 1,3-thiazolidin-1-yl, indolin-1-yl, isoindolin-2-yl, 3-pyrolin-1-yl, 1,5-dihydro-2H-pyrrol-1-yl, perhydro-1,4-thiadin-4-yl, 1,2,3,4-tetrahydroquinolin-1-yl, 1,2,3,4-tetrahydroisoquinolin-2-yl, 1,2,3,4-tetrahydropyridin-1-yl, 1,2,3,6-tetrahydropyridin-1-yl, perhydro-1,4-thiazepin-4-yl, 2,3,4,5-tetrahydro-1-benzazepin-1-yl, 2,3,4,5-tetrahydro-2-benzazepin-2-yl, 1,2,4,5-tetrahydro-3-benzazepin-3-yl, 2,3,4,5-tetrahydro-1H-azepin-1-yl, 2,3,6,7-tetrahydro-1H-azepin-1-yl, 1,3,4,7-tetrahydro-2H-azepin-1-yl, perhydro-1,4-thiazocin-4-yl, 1,2,3,4,5,6-hexahydro-1-benzazocin-1-yl, 1,2,3,4,5,6-hexahydro-2-benzazocin-2-yl, 1,2,3,4,5,6-hexahydro-3-benzazocin-3-yl, 1,2,3,4,5,6-hexahydroazocin-1-yl, 1,2,3,4,7,8-hexahydroazocin-1-yl and 1,2,3,4,5,8-hexahydroazocin-1-yl groups, or the above-mentioned heterocyclic groups wherein one to four optional hydrogen atoms on the carbon atoms of the heterocycle may independently be replaced by a lower alkyl group. Examples of the lower alkyl group are methyl, ethyl, propyl, isopropyl, butyl, isobutyl, sec-butyl and tert-butyl groups.

In B, $R^2$ means a hydrogen atom or a lower alkyl group. Examples of the lower alkyl group are methyl and ethyl groups.

$R^3$ means a lower alkyl group, a cycloalkyl group, an aryl group, a heterocyclic group, a cycloalkyl lower alkyl group, an aryl lower alkyl group or a heterocyclic lower alkyl group. Examples of the lower alkyl group are propyl, isopropyl, butyl, isobutyl, sec-butyl, tert-butyl, pentyl, isopentyl, neopentyl and tert-pentyl groups. Examples of the cycloalkyl group are cyclopropyl, cyclobutyl, cyclopentyl and cyclohexyl groups. An example of the aryl group is a phenyl group. Examples of the heterocyclic group are 2-thienyl, 3-thienyl, 2-thiazolyl, 4-thiazolyl, 5-thiazolyl, 2-furyl and 3-furyl groups. Examples of the cycloalkyl lower alkyl group are cyclopropylmethyl, 1-cyclopropylethyl, 2-cyclopropylethyl, 1-cyclopropyl-1-methylethyl, cyclobutylmethyl, 1-cyclobutylethyl, 2-cyclobutylethyl, 1-cyclobutyl-1-methylethyl, cyclopentylmethyl, 1-cyclopentylethyl, 2-cyclopentylethyl, 1-cyclopentyl-1-methylethyl, 1-cyclohexylmethyl, 1-cyclohexylethyl, 1-cyclohexyl-1-methylethyl, 1-cycloheptylmethyl, 1-cycloheptylethyl, 1-cyclooctylmethyl and 1-cyclooctylethyl groups. Examples of the aryl lower alkyl group are benzyl and phenylethyl groups. Examples of the heterocyclic lower alkyl group are 2-thienylmethyl, 3-thienylmethyl, 2-thienylethyl, 2-thiazolylmethyl, 2-furylmethyl, 3-furylmethyl, 2-pyridylmethyl, 3-pyridylmethyl, 4-pyridylmethyl, 2-indolylmethyl, 3-indolylmethyl, 2-benzothienylmethyl and 3-benzothienylmethyl groups.

In $X^1$, $R^4$ means a hydrogen atom or a lower alkyl group. Examples of the lower alkyl group are methyl and ethyl groups.

$R^5$ is a 3-indolylmethyl, 3-benzothienylmethyl, 1-naphthylmethyl group or benzyl group wherein one or two optional hydrogen atoms on the ring may be replaced by a hydroxyl group, a formyl group, a lower alkyl group, a lower alkoxy group, a lower alkoxycarbonyl group, a nitro group or a group of the formula $R^{51}$—CO—$X^2$— {wherein $R^{51}$ is a lower alkyl group, a lower alkoxy group, or an amino group which may be replaced by a lower alkyl group, and $X^2$ is an oxygen atom or a group of the formula —$NR^{52}$— (wherein $R^{52}$ is a hydrogen atom or a lower alkyl group)}. Examples of the substituted or unsubstituted 3-indolylmethyl, 3-benzothienylmethyl, 1-naphthylmethyl or benzyl group, are 3-indolylmethyl, (1-methoxycarbonyl-3-indolyl)methyl, (1-ethoxycarbonyl-3-indolyl)methyl, (1-propoxycarbonyl-3-indolyl)methyl, (1-isopropoxycarbonyl-3-indolyl)methyl, (1-butoxycarbonyl-3-indolyl)methyl, (1-isobutoxycarbonyl-3-indolyl)methyl, (1-sec-butoxycarbonyl-3-indolyl)methyl, (1-tert-butoxycarbonyl-3-indolyl)methyl, (1-formyl-3-indolyl)methyl, (1-hydroxyl-3-indolyl)methyl, (7-hydroxy-3-indolyl)methyl, (1-methyl-3-indolyl)methyl, (1-methoxy-3-indolyl)methyl, (7-methoxy-3-indolyl)methyl, (1-acetoxy-3-indolyl)methyl, (2-acetoxy-3-indolyl)methyl, (7-acetoxy-3-indolyl)methyl, (7-hydroxy-1-methoxycarbonyl-3-indolyl)methyl, (7-methoxy-1-methoxycarbonyl-3-indolyl)methyl, (2-bromo-3-indolyl)methyl, (2-chloro-3-indolyl)methyl, (2-fluoro-3-indolyl)methyl, (2-chloro-1-methyl-3-indolyl)methyl, (2-methylthio-3-indolyl)methyl, (2-methylsulfinyl-3-indolyl)methyl, (2-methylsulfonyl-3-indolyl)methyl, 2-nitrophenylmethyl, 3-nitrophenylmethyl, 4-nitrophenylmethyl, 2-methoxycarbonylphenylmethyl, 3-methoxycarbonylphenylmethyl, 4-methoxycarbonylphenylmethyl, 2-ethoxycarbonylphenylmethyl, 3-ethoxycarbonylphenylmethyl, 4-ethoxycarbonylphenylmethyl, 2-acetoxyphenylmethyl, 3-acetoxyphenylmethyl, 4-acetoxyphenylmethyl, 2-methoxycarbonyloxyphenylmethyl, 3-methoxycarbonyloxyphenylmethyl, 4-methoxycarbonyloxyphenylmethyl, 2-carbamoyloxyphenylmethyl, 3-carbamoyloxyphenylmethyl, 4-carbamoyloxyphenylmethyl, 2-methylcarbamoyloxyphenylmethyl, 3-methylcarbamoyloxyphenylmethyl, 4-methylcarbamoyloxyphenylmethyl, 2-dimethylcarbamoyloxyphenylmethyl, 3-dimethylcarbamoyloxyphenylmethyl, 4-dimethylcarbamoyloxyphenylmethyl, 2-acetamidophenylmethyl, 3-acetamidophenylmethyl, 4-acetamidophenylmethyl, 2-methoxycarbonylaminophenylmethyl, 3-methoxycarbonylaminophenylmethyl, 4-methoxycarbonylaminophenylmethyl, 2-ureidophenylmethyl, 3-ureidophenylmethyl, 4-ureidophenylmethyl, 2-(3-methylureido)phenylmethyl, 3-(3-methylureido)phenylmethyl, 4-(3-methylureido)phenylmethyl, 2-(3,3-dimethylureido)phenylmethyl, 3-(3,3-dimethylureido)phenylmethyl, 4-(3,3-dimethylureido)phenylmethyl, 2-hydroxyphenylmethyl, 3-hydroxyphenylmethy, 4-hydroxyphenylmethyl, 2-methoxyphenylmethyl, 3-methoxyphenylmethyl and 4-methoxyphenylmethyl groups.

Among them, preferred are 3-indolylmethyl groups wherein the 1- and/or 2-position of the indole ring may be substituted by 1 to 2 substituents selected from the group consisting of a halogen atom, a lower alkyl group, a lower alkoxy group, a lower alkanoyloxy group, a lower alkylthio group, a lower alkylsulfinyl group, a lower alkylsulfonyl group, and a lower alkoxycarbonyl group, such as, 3-indolylmethyl, (1-methoxycarbonyl-3-indolyl)methyl, (1-ethoxycarbonyl-3-indolyl)methyl, (1-propoxycarbonyl-3-indolyl)methyl, (1-isopropoxycarbonyl-3-indolyl)methyl, (1-butoxycarbonyl-3-indolyl)methyl, (1-isobutoxycarbonyl-3-indolyl)methyl, (1-sec-butoxycarbonyl-3-indolyl)methyl, 1-tert-butoxycarbonyl-3-indolyl)methyl, (1-acetoxy-3-indolyl)methyl, (2-acetoxy-3-indolyl)methyl, (1-methoxy-3-indolyl)methyl, (2-bromo-3-indolyl)methyl, (2-chloro-3-indolyl)methyl, (2-fluoro-3-indolyl)methyl, (2-chloro-1-methyl-3-indolyl)methyl, (2-methylthio-3-indolyl)methyl, (2-methylsulfinyl-3-indolyl)methyl and (2-methylsulfonyl-3-indolyl)methyl groups.

$R^6$ means a hydrogen atom, or a lower alkyl or lower alkenyl group which may have 1 to 3 substituents selected from the group consisting of hydroxyl, lower alkoxy, lower alkylthio and heterocyclic groups. Examples of the lower alkyl or lower alkenyl group which may be substituted by 1 to 3 substituents selected from the group consisting of hydroxyl, lower alkoxy, lower alkylthio and heterocyclic groups, are methyl, ethyl, propyl, isopropyl, butyl, isobutyl, sec-butyl, tert-butyl, pentyl, isopentyl, neopentyl, tert-pentyl, hexyl, hydroxymethyl, 1-hydroxyethyl, methoxymethyl, 1-methoxyethyl, methylthiomethyl, ethylthiomethyl, propylthiomethyl, butylthiomethyl, 2-methylthioethyl, 2-ethylthioethyl, 3-indolylmethyl, 4-imidazolylmethyl, vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 4-pentenyl, 5-pentenyl, 1-hydroxy-2-propenyl, 1-methoxy-2-propenyl, 1-methylthio-2-propenyl, 2-hydroxy-3-butenyl and 2-ethylthio-3-butenyl groups. Among them, preferred are a lower alkyl or lower alkenyl group which may have a substituent selected from the group consisting of lower alkoxy and lower alkylthio groups, such as, methyl, ethyl, propyl, isopropyl, butyl, isobutyl, neopentyl, tert-pentyl, hexyl, methoxymethyl, 1-methoxyethyl, methylthiomethyl, ethylthiomethyl, propylthiomethyl, butylthiomethyl, 2-methylthioethyl, 2-ethylthioethyl, vinyl, allyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 4-pentenyl, 1-hydroxy-2-propenyl, 1-methoxy-2-propenyl, 1-methylthio-2-propenyl, 2-hydroxy-3-butenyl and 2-ethylthio-3-butenyl groups.

$R^{71}$ means a hydrogen atom or a lower alkyl group. Examples of the lower alkyl group are methyl, ethyl, propyl, isopropyl, butyl, isobutyl, sec-butyl, tert-butyl, pentyl, isopentyl, neopentyl and hexyl groups.

$R^{72}$ means a hydrogen atom or a lower alkyl group which may be substituted by a substituent selected from the group consisting of hydroxyl, carboxyl, and sulfo groups. Examples of the lower alkyl group which may be substituted by a substituent selected from the group consisting of hydroxyl, carboxyl, and sulfo groups, are 2-hydroxyethyl, carboxymethyl, 1-carboxyethyl, 2-carboxyethyl, sulfomethyl and 2-sulfoethyl groups.

Now, the process for producing the novel peptide derivatives of the present invention will be described.

A peptide derivative of the present invention can be prepared by a method wherein amino acids composing the target peptide derivative are condensed one by one, and then, if necessary, removing a C-terminal protective group (Method 1). Peptide derivatives prepared by Method 1 can be converted into other peptide derivatives of the present invention, as the case requires, by a combination of the following reactions: (1) alkoxycarbonylation, aryloxycarbonylation or carbamoylation of the N-terminal α-amino group after removal of an N-terminal amino-protecting group (Methods 2 and 3), (2) alkoxycarboylation (Method 4) or hydroxylation or alkoxylation (Method 5) at the 1-position of the indole ring of tryptophan, and (3) halogenation (Method 6), or lower alkylthiolation, lower alkylsulfinylation or lower alkylsulfonation (Method 7) at the 2-position of the indole ring of tryptophan. Furthermore, these peptide derivatives can, if necessary, be converted to pharmaceutically acceptable salts.

Each method will be detailed as follows.

METHOD 1

Method 1 is a conventional synthetic method for peptides, that is, a method wherein amino acids or amino acid derivatives are condensed one by one to prepare a desired peptide derivative. Furthermore, after condensation, a C-terminal protective group can be removed by alkaline hydrolysis, catalytic hydrogenation or acid decomposition. Condensation can be conducted according to known methods such as a DCC method, an azide method, an active ester method and a mixed acid anhydride method (described, for example, by M. Bodansky and M. A. Ondetti in Peptide Synthesis, Interscience, New York, 1966; by F. M. Finn and K. Hofmann in The Proteins, Vol. 2, ed. by H. Nenrath and R. L. Hill, Academic Press Inc., New York, 1976; by Nobuo Izumiya et al. in Peptide Synthesis, Maruzen, 1975).

For example, in the case wherein condensation is carried out by a DCC method, an α-amino acid derivative or an α-hydroxycarboxylic acid derivative of the formula

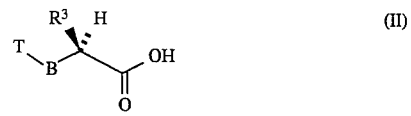

(II)

wherein T is A or an α-amino-protecting group, and A, B and $R^3$ are as defined before, is treated with a condensing reagent such as DCC(or EDCI.HCl)-HOBT.H$_2$O in a suitable solvent such as DMSO, NMP, DMF, THF, 1,4-dioxane, acetonitrile, dichloromethane or chloroform at around −40° C. to room temperature, then condensed with an α-amino acid derivative or an α-hydroxycarboxylic acid derivative having an α-carboxyl-protecting group, of the formula:

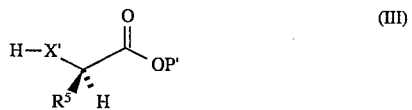

(III)

wherein $P^1$ is an α-carboxyl-protecting group, and $X^1$ and $R^5$ are as defined before, to afford a dipeptide derivative of the formula:

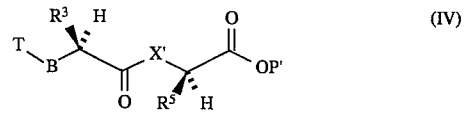

(IV)

wherein T, B, $R^3$, $R^5$, $X^1$ and $P^1$ are as defined before. An N-terminal α-amino-protecting group is usually selected from the groups well-known to those skilled in the art, for example, from urethane type protective groups such as a Z group, a Boc group, a p-methoxybenzyloxycarbonyl group and a p-nitrobenzyloxycarbonyl group, while the C-terminal α-carboxyl group is usually protected as, for example, a methyl ester, an ethyl ester, a benzyl ester or a tert-butyl ester. Each protective group should be selected so that it can be selectively deprotected after condensation. For example, in the case that a Boc group is selected as an N-terminal protective group, it is preferable to protect the C-terminus as a methyl group, an ethyl group or a benzyl group. A Boc group will be readily removed by use of a mild acid such as TFA, while the carboxyl-protecting groups described above will be usually intact under these conditions. On the other hand, a methyl, ethyl or benzyl ester will be easily deprotected by alkaline hydrolysis and a benzyl ester will be also deprotected by catalytic hydrogenation, while a Boc group will be intact under these conditions.

In the case that T is an α-amino-protecting group, the group T will be formally converted to A by removal of T from the dipeptide derivative (IV) followed by N-alkoxycarbonylation, N-aryloxycarbonylation or N-carbamoylation which will be carried out under the reaction conditions described later in Method 2.

A C-terminal protective group of the dipeptide derivative (IV) prepared in the above-mentioned manner is now removed, and the resulting deprotected dipeptide is treated with a condensation reagent (for example, EDCI.HCl-HOBT.H$_2$O) in the same manner described above and then with an amino acid whose C-terminal carboxyl group is protected, to afford a desired peptide derivative.

In the case that each of B and X$^1$ is —NR$^2$— or —NR$^4$—, and P$^1$ is a lower alkyl group or a benzyl group, the dipeptide derivative (IV) may be treated with an excess amount of hydrazine in a solvent such as methanol or DMF at room temperature to afford the corresponding hydrazide, which can be converted to a desired peptide derivative by an azide method. Namely, the hydrazide is first converted to the corresponding azide on treatment with a reagent such as a lower alkyl ester of nitrous acid (for example, tert-butyl nitrite or isoamyl nitrite) or an alkaline metal salt of nitrous acid (for example, sodium nitrite or potassium nitrite) in the presence of a strong acid such as hydrochloric acid or sulfuric acid (this reaction can be performed in a solvent such as water, and/or DMF, THF or 1,4-dioxane at around −60° C. to −15° C.). Then, the azide is mixed with a tertiary amine such as TEA, and a C-terminal ester derivative of an amino acid at −70° C. to −60° C., and then allowed to react at −20° C. to room temperature to afford a desired peptide derivative. A tetrabutylammonium-, triethylammonium-, sodium- or potassium-salt of an amino acid can also be used instead of the C-terminal ester derivative.

In the process so far described, a C-terminal amino acid or a C-terminal dipeptide is lastly condensed to give a target peptide derivative. The alternative process wherein an N-terminal amino acid is lastly condensed to give a target product is also available. Namely, a compound of the formula:

(V)

wherein P$^2$ is a hydrogen atom or an α-amino-protecting group, and R$^5$ and X$^1$ are as defined before, is condensed with a compound of the formula:

(VI)

wherein n, R$^6$ and Y are as defined before, by a DCC method or an azide method to afford an N-terminal protected peptide derivative or α-hydroxycarboxylic acid derivative. A suitable α-amino-protecting group can be selected from the urethane type protective groups described before, and a C-terminal carboxyl group can be protected as an ester. In the case that a C-terminal carboxyl group is protected as, for example, a tert-butyl ester, a Z group or a Boc group is preferable for a N-terminal amino-protecting group. A Z group will be readily removed by catalytic hydrogenation and a Boc group will be readily removed by treatment with a mild acid such as formic acid or TFA under ice-cooling, while under these conditions these C-terminal carboxyl-protecting groups will be intact.

An α-hydroxycarboxylic acid derivative or a dipeptide derivative (in the case of a dipeptide derivative, an N-terminal amino protecting group is removed prior to following treatments) prepared in the above-mentioned manner is treated with a condensation reagent (for example, EDCI.HCl-HOBT.H$_2$O) in the same manner described above and then with an N$^\alpha$-substituted amino acid or an O$^\alpha$-substituted hydroxycarboxylic acid, to afford a desired peptide derivative. A peptide derivative of the formula (I) wherein X$^3$ is a sulfur atom, can be prepared by condensation of a compound of the formula (V) with a compound of the formula (VI) whose C-terminal carboxyl group is protected, followed by conversion of the resulting amide bond to the thioamide bond on treatment with, for example, the Lawesson's reagent, then condensed with a compound of the formula (II) by, for example, a DCC method or an azide method to afford a target peptide derivative elongated toward the N-terminus.

A C-terminal protective group of a peptide derivative prepared by the method so far described, can be deprotected by a suitable method, if necessary. For example, in the case that a carboxyl group is protected as a tert-butyl ester, the protective group can be readily removed by acid decomposition, that is, by treatment with a mild acid such as formic acid or TFA. In the case that a carboxylic acid is protected as a benzyl ester, the protective group can be readily removed by catalytic hydrogenation, that is, by hydrogenation under 1 to 4 atmospheric pressures of hydrogen in the presence of a catalyst such as Pd-C or palladium black in a solvent such as methanol, ethanol, DMF, THF, 1,4-dioxane or acetic acid.

METHOD 2

Method 2 is a process for producing a peptide derivative which possesses an alkoxycarbonyl, aryloxycarbonyl or carbamoyl group at the N-terminus, wherein an N-terminal amino protective group of an amino acid derivative or a peptide derivative prepared by Method 1, is removed, and the resulting deprotected amino group is reacted with an acid chloride such as a chloroformate (R$^{11}$OCOCl) or a carbamoyl chloride (R$^{12}$R$^{13}$NCOCl) in the presence of a base, or reacted with an isocyanate (R$^{12}$NCO) (wherein R$^{11}$, R$^{12}$ and R$^{13}$ are as defined before), furthermore, a C-terminal protective group is optionally removed by alkaline hydrolysis, catalytic hydrogenation or acid decomposition.

An N-terminal protective group of the precursor can be readily removed by a conventional method such as catalytic hydrogenation (a Z group) or by treatment with a mild acid such as TFA (a Boc group). The reaction of the resulting deprotected peptide derivative from which the N-terminal amino protective group is removed by the method described above, with an acid chloride such as a chloroformate (R$^{11}$OCOCl) or a carbamoyl chloride (R$^{12}$R$^{13}$NCOCl) can be performed in a suitable solvent such as chloroform, dichloromethane, THF, 1,4-dioxane, toluene or pyridine in the presence of a base such as TEA, DMAP, N-methylmorpholine or pyridine at 0° C. to the boiling point of the solvent. The reaction with an isocyanate (R$^{12}$NCO) can be performed in a solvent such as chloroform, dichloromethane, THF, 1,4-dioxane or toluene at 0° C. to the boiling point of the solvent.

A C-terminal protective group of peptide derivatives prepared by the above-mentioned method can be removed by alkaline hydrolysis, catalytic hydrogenation or acid decomposition in the same manner described in Method 1, if necessary.

METHOD 3

Method 3 is a process for producing an amino acid or a peptide derivative which possesses a carbamoyl group at the N-terminus, by treatment of an amino acid derivative or a peptide derivative (prepared by Method 1 or 2) having an aryloxycarbonyl group at the N-terminus, with a primary or secondary amine R$^{12}$NHR$^{13}$ wherein R$^{12}$ and R$^{13}$ are as defined before, furthermore optionally removing a C-terminal protective group by alkaline hydrolysis, catalytic hydrogenation or acid decomposition.

That is, a peptide derivative possessing a carbamoyl group at the N-terminus can be prepared by dissolving a peptide derivative possessing an aryloxycarbonyl group at the N-terminus in a solvent such as chloroform, dichloromethane, THF, 1,4-dioxane, toluene or pyridine, followed by addition of the primary or secondary amine described above, optional addition of a tertiary amine such as TEA or DMAP, and allowing them to react at room temperature to the boiling point of the solvent. A C-terminal protective group of the product can be removed, if necessary, by alkaline hydrolysis, catalytic hydrogenation or acid decomposition in the same manner described in Method 1.

METHOD 4

Method 4 is a process for alkoxycarbonylation at the 1-position of the indole ring of a tryptophanyl residue when the peptide derivative prepared in the present invention contains the tryptophanyl residue.

The alkoxycarbonylation of the indole ring at the 1-position can be performed by treatment of a tryptophan-containing dipeptide or tripeptide derivative prepared by optionally combining Methods 1, 2 and 3, or an optionally protected tryptophan derivative as the starting material thereof, with a base (such as sodium hydroxide) and alkyl chloroformate in a solvent such as dichloromethane in the presence of TBAHS.

METHOD 5

Method 5 is a process for hydroxylation or lower alkoxylation at the 1-position of the indole ring when the peptide derivative prepared in the present invention contains a tryptophanyl residue.

The hydroxylation of the indole ring at the 1-position can be performed by treatment of a tryptophan-containing dipeptide or tripeptide derivative prepared by optionally combining Methods 1, 2, and 3, or an optionally protected tryptophan derivative as the starting material thereof, with sodium cyanoborohydride in a solvent such as acetic acid, and treatment of the resulting indoline derivative with hydrogen peroxide in methanol, water or a mixed solvent thereof. The lower alkoxylation of the indole ring at the 1-position can be performed by treatment of the hydroxylated derivative with, for example, diazomethane or diazoethane.

METHOD 6

Method 6 is a process for halogenation at the 2-position of the indole ring of a tryptophanyl residue when the peptide derivative prepared in the present invention contains the tryptophanyl residue.

The halogenation of the indole ring at the 2-position can be performed by treatment of a tryptophan-containing dipeptide or tripeptide derivative prepared by optionally combining methods 1, 2 and 3, or an optionally protected tryptophan derivative as the starting material thereof, with an N-halosuccinimide such as N-bromosuccinimide or N-chlorosuccinimide in a solvent such as acetic acid or carbon tetrachloride, optionally in the presence of 2,2'-azobis(isobutyronitrile) or the like.

METHOD 7

Method 7 is a process for lower alkylthiolation, lower alkylsulfinylation or lower alkylsulfonylation at the 2-position of the indole ring of a tryptophanyl residue when the peptide derivative prepared in the present invention contains the tryptophanyl residue.

The lower alkylthiolation of the indole ring at the 2-position can be performed by treatment of a tryptophan-containing dipeptide or tripeptide derivative prepared by optionally combining methods 1, 2 and 3, or an optionally protected tryptophan derivative as the starting material thereof, with a lower alkylsulfenyl chloride in a solvent such as acetic acid. The lower alkylsulfinylation or lower alkylsulfonylation at the 2-position of the indole ring can be performed by treatment of the sulfide derivative thus obtained, with an oxidizing agent such as hydrogen peroxide or m-chloroperbenzoic acid in a solvent such as acetic acid or dichloromethane.

All reaction intermediates and products so far described can be purified by well-known methods such as recrystallization, reprecipitation, partition procedures, normal- or reverse-phase chromatography and ion-exchange chromatography.

Starting materials used in the methods so far described are commercially available except for the following materials, which are prepared by the known method in the literature.

DL-3-(3-ethoxycarbonylphenyl)alanine and DL-3-(4-methoxycarbonylphenyl)alanine: Synthesis, 53 (1984).

D-3-(3-benzothienyl)alanine: Chem. Pharm. Bull., 24, 3149 (1976).

D-S-methylcysteine, D-S-ethylcysteine, D-S-n-propylcysteine: by Nobuo Izumiya et al in Peptide Synthesis, Maruzen, 1975.

D-norleucinol: synthesized in the same manner described in J. Am. Chem. Soc., 107, 7974 (1985).

D-3-cyclopropylalanine: J. Am. Chem. Soc., 111, 6354 (1989).

D-cyclopropylglycine: J. Am. Chem. Soc., 111, 6354 (1989).

D-cyclopentylglycine: J. Org. Chem., 30, 1320 (1965).

D-3-(3-nitrophenyl)alanine: Pept. Res.), 3, 176 (1990).

DL-1-aminopentanesulfonic acid: European Laid-open Patent Publication No. 33504.

D-1-aminopentylphosphonic acid diethyl ester: synthesized in the same manner described in Liebigs Ann. Chem., 45 (1987).

D-(7-benzyloxy)tryptophan: synthesized in the same manner described in Tetrahedron Letters, 30, 4073 (1989).

(R)-5-(1-aminopentyl)-1H-tetrazole hydrochloride: synthesized in the same manner described in J. Org. Chem., 56, 2395 (1991).

α-N-trifluoroacetyl-2-chloro-D-tryptophan methyl ester and

α-N-trifluoroacetyl-1-methyl-2-chloro-D-tryptophan: synthesized in the same manner described in J. Am. Chem. Soc., 108, 2023 (1986).

The chemical structures, Example Nos. and compound Nos. of the prepared peptide derivatives in the present invention are shown in Tables 1 to 7.

TABLE 1

Structure: (CH₃)₂CHCH₂–A–NH–CH(H)–C(O)–NH–CH(CH₂-[1-(COOMe)-indol-3-yl])–C(O)–NH–CH((CH₂)₃CH₃)–COOH

| Exp. No. | Compd No. | A |
|---|---|---|
| 1 | 1 | Boc |
| 4 | 4 | 2-Cl-C₆H₄-NHCO— |
| 21 | 21 | 2,6-di-Cl-C₆H₃-NHCO— |
| 22 | 22 | 2-F-C₆H₄-NHCO— |
| 23 | 23 | 2-CF₃-C₆H₄-NHCO— |
| 24 | 24 | 2-NO₂-C₆H₄-NHCO— |
| 25 | 25 | 2-NH₂-C₆H₄-NHCO— |
| 26 | 26 | 2-NHCHO-C₆H₄-NHCO— |
| 27 | 27 | C₆H₅-OCO— |

TABLE 1-continued

| Exp. No. | Compd No. | A |
|---|---|---|
| 28 | 28 | cycloheptyl-NCO— |
| 29 | 29 | 4-thianyl-NCO— |
| 30 | 30 | cyclopentyl-NCO— |
| 31 | 31 | cyclohexyl-NCO— |
| 32 | 32 | 3-thiolanyl-NCO— |
| 33 | 33 | (cyclopropyl)₂CH-NCO— |
| 34 | 34 | 2-methylcyclopentyl-NCO— |
| 35 | 35 | 2-methylcyclohexyl-NCO— |
| 36 | 36 | N-cyclopentyl-N-propyl-NCO— |
| 37 | 37 | 1,2,3,4-tetrahydronaphthalen-1-ylmethyl-NCO— |

TABLE 1-continued
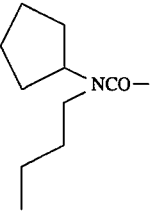
| Exp. No. | Compd No. | A |
|---|---|---|
| 38 | 38 | 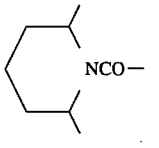 |
| 39 | 39 | 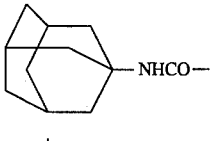 |
| 44 | 44 | 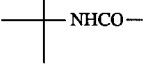 |
| 46 | 46 | 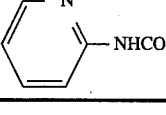 |
| 47 | 47 | 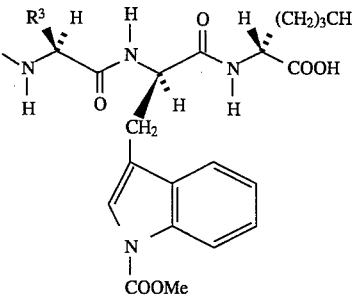 |
TABLE 2
| Exp. No. | Compd No. | A | R³ |
|---|---|---|---|
| 14 | 14 | Boc | —(CH₂)₃CH₃ |
| 15 | 15 | Boc | —CH₂C(CH₃)₃ |
TABLE 2-continued
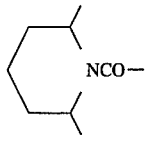
| Exp. No. | Compd No. | A | R³ |
|---|---|---|---|
| 40 | 40 | 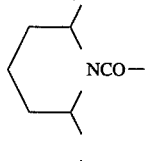 | —CH₂C(CH₃)₃ |
| 41 | 41 | 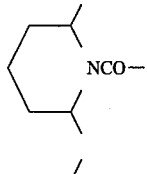 | —CH₂Ph |
| 42 | 42 | 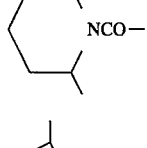 | —CH₂—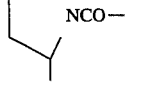 |
| 43 | 43 |  | —CH(CH₃)₂ |
| 62 | 67 | 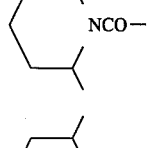 | —CH(CH₃)₂ |
| 63 | 68 | 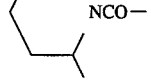 | —CH₂—◁ |
| 64 | 69 | 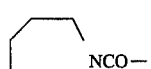 | ◁ |
| 65 | 70 | 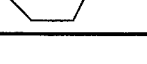 | —⬠ |

TABLE 3

Structure:
(CH₃)₂CHCH₂ and H on left carbon (S config), A-NH- group; central N-CH(R⁵)-C(=O)- with * chiral center; right carbon bearing (CH₂)₃CH₃ and H, -COOH (S config).

| Exp. No. | Compd No. | A | * | R⁵ |
|---|---|---|---|---|
| 3 | 3 | Boc | (R) | -CH₂-(2-(NCOOEt)vinyl-phenyl) |
| 5 | 5 | 2-Cl-C₆H₄-NHCO- | (R) | -CH₂-(2-(NCOOEt)vinyl-phenyl) |
| 16 | 16 | Boc | (R) | -CH₂-(1-naphthyl) |
| 17 | 17 | Boc | (RS) | -CH₂-(2-(NMe)vinyl-phenyl) |
| 18 | 18 | 2-Cl-C₆H₄-NHCO- | (R) | -CH₂-(benzo[b]thiophen-3-yl) |
| 19 | 19 | 2-Cl-C₆H₄-NHCO- | (RS) | -CH₂-C₆H₄-COOEt |
| 20 | 20 | 2-Cl-C₆H₄-NHCO- | (RS) | -CH₂-C₆H₄-COOMe |
| 97 | 112 | (2,6-dimethylheptyl)-NCO- | (R) | -CH₂-(2-(NH)(Cl)vinyl-phenyl) |

TABLE 3-continued

| Exp. No. | Compd No. | A | * | R⁵ |
|---|---|---|---|---|
| 98 | 113 | (cycloheptyl)NCO— | (R) | —CH₂—(2-chloro-indole) |

TABLE 4

| Exp. No. | Compd No. | R⁶ | Y |
|---|---|---|---|
| 2 | 2 | —(CH₂)₂CH₃ | COOH |
| 6 | 6 | —(CH₂)₂SCH₃ | COOH |
| 7 | 7 | —CH₂SCH₃ | COOH |
| 8 | 8 | —CH₂SCH₂CH₃ | COOH |
| 9 | 9 | —CH₂S(CH₂)₂CH₃ | COOH |
| 10 | 10 | —CH₂CH=CH₂ | COOH |
| 11 | 11 | —CH₂CH(CH₃)₂ | COOH |
| 12 | 12 | (R)—*CHCH₂CH₃ / CH₃ | COOH |
| 13 | 13 | —(CH₂)₃CH₃ | CH₂OH |
| 45 | 45 | —CH₂CH₃ | COOH |
| 60 | 65 | —CH₂OH | COOH |
| 66 | 71 | —CH₂OCH₃ | COOH |

TABLE 5

| Exp. No. | Comp No. | A | B | R³ | X¹ | X² | R⁶ | Y |
|---|---|---|---|---|---|---|---|---|
| 48 | 48 | (cyclohexyl)NCO— | —NH— | —CH₂CH(CH₃)₂ | NH | O | —(CH₂)₃CH₃ | COOᵗBu |

TABLE 5-continued

[Structure: A-B-CHR³-C(=O)-X¹-CH(CH₂-indole-N-COOMe)-C(=X²)-NH-CHR⁶-Y]

| Exp. No. | Comp No. | A | B | R³ | X¹ | X² | R⁶ | Y |
|---|---|---|---|---|---|---|---|---|
| 48 | 49 | cyclohexyl-NCO— | —NH— | —CH₂CH(CH₃)₂ | NH | O | —(CH₂)₃CH₃ | COOH |
| 49 | 50 | 2,6-dimethylcyclohexyl-NCO— | —NH— | —CH₂CH(CH₃)₂ | NH | O | —(CH₂)₂CH₃ | COOH |
| 50 | 51 | 2,6-dimethylcyclohexyl-NCO— | —NH— | —CH₂C(CH₃)₃ | NH | O | —(CH₂)₂CH₃ | COOH |
| 51 | 52 | 2,6-dimethylcyclohexyl-NCO— | —NH— | (S)—*CHCH₂CH₃ / CH₃ | NH | O | —(CH₂)₃CH₃ | COOH |
| 52 | 53 | 2,6-dimethylcyclohexyl-NCO— | —NH— | (R)—*CHCH₂CH₃ / CH₃ | NH | O | —(CH₂)₃CH₃ | COOH |
| 53 | 54 | 2,6-dimethylcyclohexyl-NCO— | —NH— | —C(CH₃)₃ | NH | O | —(CH₂)₃CH₃ | COOH |
| 54 | 55 | 2-Cl-phenyl-NHCO— | —O— | —CH₂CH(CH₃)₂ | NH | O | —(CH₂)₃CH₃ | COOH |
| 55 | 56 | Boc | —NH— | —CH₂CH(CH₃)₂ | NH | O | —CH(CH₃)₂ | COOH |
| 56 | 57 | 2,6-dimethylcyclohexyl-NCO— | —NH— | —CH₂C(CH₃)₃ | NH | S | —(CH₂)₃CH₃ | COOⁱBu |

TABLE 5-continued

[Structure: A-B-CH(R³)(H)-C(=O)-X¹-CH(H)(CH₂-indole-N-COOMe)-C(=X²)-NH-CH(H)(R⁶)-Y]

| Exp. No. | Comp No. | A | B | R³ | X¹ | X² | R⁶ | Y |
|---|---|---|---|---|---|---|---|---|
| 56 | 58 | (2,6-dimethylpiperidinyl)-NCO— | —NH— | —CH₂C(CH₃)₃ | NH | S | —(CH₂)₃CH₃ | COOH |
| 57 | 59 | (2,6-dimethylpiperidinyl)-NCO— | —NH— | —CH₂C(CH₃)₃ | O | O | —(CH₂)₃CH₃ | COOH |
| 58 | 60 | (2,6-dimethylpiperidinyl)-NCO— | —NH— | —CH₂C(CH₃)₃ | NH | O | —(CH₂)₃CH₃ | COO$^t$Bu |
| 61 | 66 | 2-thienyl-NHCO— | —NH— | —CH₂C(CH₃)₃ | NH | O | —(CH₂)₃CH₃ | COOH |

TABLE 6

[Structure: A-NH-CH((CH₃)₃CCH₂)(H)-C(=O)-N(H)-CH(R⁵)(H)-C(=O)-NH-CH((CH₂)₃CH₃)(H)-Y]

| Exp. No. | Compd No. | A | R⁵ | Y |
|---|---|---|---|---|
| 59 | 61 | (2,6-dimethylpiperidinyl)-NCO— | —CH₂—(3-hydroxyphenyl) | COOH |
| 59 | 62 | (2,6-dimethylpiperidinyl)-NCO— | —CH₂—(3-acetoxyphenyl) | COOH |
| 59 | 63 | (2,6-dimethylpiperidinyl)-NCO— | —CH₂—(3-methoxyphenyl) | COOH |

TABLE 6-continued (CH₃)₃CCH₂ and (CH₂)₃CH₃ substituted tripeptide structure with A-NH-, R⁵, and Y substituents

| Exp. No. | Compd No. | A | R⁵ | Y |
|---|---|---|---|---|
| 59 | 64 | cyclohexyl-NCO- | -CH₂-C₆H₄-OCOOMe (meta) | COOH |
| 67 | 72 | cyclohexyl-NCO- | -CH₂-C₆H₄-NO₂ (meta) | COOH |
| 67 | 73 | cyclohexyl-NCO- | -CH₂-C₆H₄-NH₂ (meta) | COOH |
| 67 | 74 | cyclohexyl-NCO- | -CH₂-C₆H₄-NHCHO (meta) | COOH |
| 67 | 75 | cyclohexyl-NCO- | -CH₂-C₆H₄-NHCOOMe (meta) | COOH |
| 68 | 76 | cyclohexyl-NCO- | -CH₂-benzothiophene | COO$^t$Bu |
| 68 | 77 | cyclohexyl-NCO- | -CH₂-benzothiophene | COOH |
| 69 | 78 | cyclohexyl-NCO- | -CH₂-(N-OH)indole | COOH |
| 69 | 79 | cyclohexyl-NCO- | -CH₂-(N-OMe)indole | COOH |

TABLE 6-continued
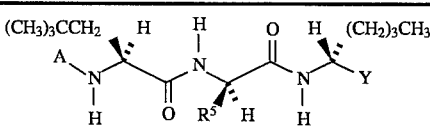
| Exp. No. | Compd No. | A | R⁵ | Y |
|---|---|---|---|---|
| 70 | 80 | 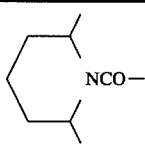 | 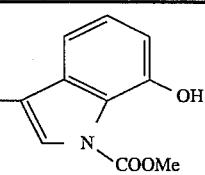 | COOH |
| 70 | 81 | 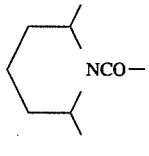 | 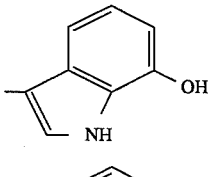 | COOH |
| 70 | 82 | 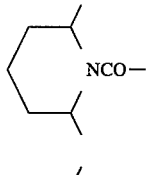 | 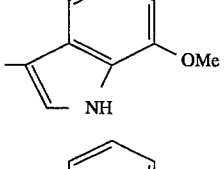 | COOH |
| 70 | 83 | 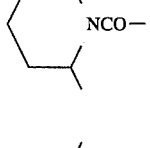 | 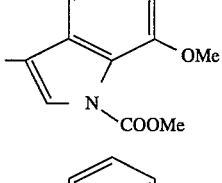 | COOH |
| 74 | 87 | 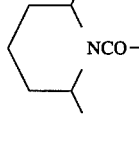 | 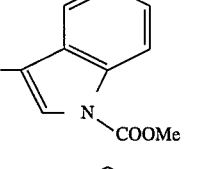 | CH₂OH |
| 74 | 88 | 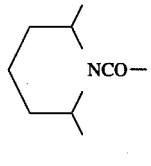 | 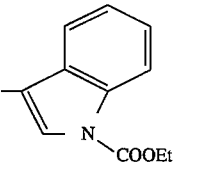 | CH₂OH |
| 87 | 102 | 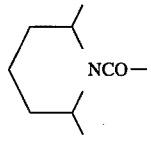 | 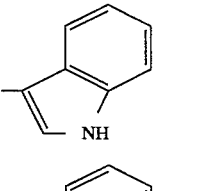 | COOH |
| 88 | 103 | 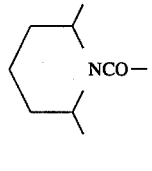 | 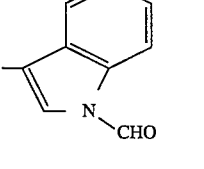 | COOH |

TABLE 6-continued

Structure: (CH₃)₃CCH₂—CH(A-NH)—C(=O)—NH—CH(R⁵)—C(=O)—NH—CH((CH₂)₃CH₃)—Y

| Exp. No. | Compd No. | A | R⁵ | Y |
|---|---|---|---|---|
| 89 | 104 | 2,6-dimethylcyclohexyl-NCO— | —CH₂—(3-indolyl with 7-OCOMe) | COOH |
| 95 | 110 | 2,6-dimethylcyclohexyl-NCO— | —CH₂—(3-indolyl with 2-Br) | COOH |
| 96 | 111 | 2,6-dimethylcyclohexyl-NCO— | —CH₂—(3-indolyl with 2-Cl) | COOH |
| 99 | 114 | 2,6-dimethylcyclohexyl-NCO— | —CH₂—(3-indolyl with 2-Cl, N—CH₃) | COOH |
| 100 | 115 | 2,6-dimethylcyclohexyl-NCO— | —CH₂—(3-indolyl with 2-SCH₃) | COOH |
| 101 | 116 | 2,6-dimethylcyclohexyl-NCO— | —CH₂—(3-indolyl with 2-S(O)CH₃) | COOH |
| 102 | 117 | 2,6-dimethylcyclohexyl-NCO— | —CH₂—(3-indolyl with 2-S(O₂)CH₃) | COOH |

TABLE 7

| Exp. No. | Compd No. | R³ | R⁶ | * | Y |
|---|---|---|---|---|---|
| 71 | 84 | —CH₂C(CH₃)₃ | —(CH₂)₃CH₃ | (R) | COOMe |
| 72 | 85 | —CH₂C(CH₃)₃ | —(CH₂)₃CH₃ | (R) | COOEt |
| 73 | 86 | —CH₂C(CH₃)₃ | —(CH₂)₃CH₃ | (R) | COOⁱPr |
| 75 | 89 |  | —(CH₂)₃CH₃ | (R) | COOᵗBu |
| 75 | 90 |  | —(CH₂)₃CH₃ | (R) | COOH |
| 76 | 91 | 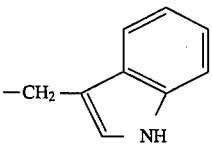 | —CH₃ | (R) | CH₂COOH |
| 77 | 92 | —CH₂C(CH₃)₃ | —H | — | COOH |
| 78 | 93 | —CH₂C(CH₃)₃ | —H | — | CH₂COOH |
| 81 | 96 | —CH₂C(CH₃)₃ | —H | — | SO₃H |
| 79 | 94 | —CH₂C(CH₃)₃ | 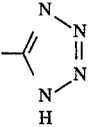 | (R) | COOH |
| 80 | 95 | —CH₂C(CH₃)₃ | —(CH₂)₃CH₃ | (R) | CH₂COOH |
| 82 | 97 | —CH₂C(CH₃)₃ | —H | — | CH₂SO₃H |
| 83 | 98 | —CH₂C(CH₃)₃ | —(CH₂)₃CH₃ | (R) | CH₂SO₃H |
| 84 | 99 | —CH₂C(CH₃)₃ | —(CH₂)₃CH₃ | (RS) | SO₃H |
| 85 | 100 | —CH₂C(CH₃)₃ | —(CH₂)₃CH₃ | (S) | PO₃H₂ |
| 86 | 101 | —CH₂C(CH₃)₃ | —(CH₂)₃CH₃ | (R) | CONHCH₂CH₂OH |
| 90 | 105 | —CH₂C(CH₃)₃ | —(CH₂)₃CH₃ | (R) | tetrazolyl |
| 91 | 106 | —CH(CH₃)₂ | —(CH₂)₃CH₃ | (RS) | SO₃H |
| 92 | 107 | —CH(CH₃)₂ | —(CH₂)₃CH₃ | (R) | CH₂SO₃H |
| 93 | 108 | —CH₂CH(CH₃)₂ | —(CH₂)₃CH₃ | (R) | CH₂SO₃H |
| 94 | 109 | —CH₂CH(CH₃)₂ | —(CH₂)₃CH₃ | (RS) | SO₃H |

Now, the endothelin antagonistic properties of the peptide derivatives of the present invention will be described.

Endothelin Binding Inhibition Test

The cerebellum of porcine was homogenized in a buffer solution of 10 mM MOPS, pH 7.4, at 4° C. by a polytron. To the homogenate, sucrose was added to a concentration of 20%, and the mixture was centrifuged at 1,000×g for 15 minutes, and the supernatant was further centrifuged at 10,000×g for 15 minutes. The supernatant thereof was further centrifuged at 90,000×g for 40 minutes. The membrane precipitate thereby obtained was suspended in a buffer solution of 5 mM HEPES/Tris, pH 7.4, at a concentration of 3.3 mg/ml.

Then, 16 μl of this membrane suspension was added to 340 μl of 50 mM tris/HCl buffer, pH 7.4, containing 10 μl calcium chloride, 10 μM magnesium chloride, 0.1 mM PMSF, 1 μM pepstatin A, 2 μM leupeptin, 1 mM 1,10-phenanthroline and 0.1% bovine serum albumin. To this suspension, 4 μl of (A) endothelin-1 (for nonspecific binding; 0.2 μM as the final concentration), (B) buffer solution A (for total control binding), or (C) a test compound (1.1 μM as the final concentration), was added. Further, to each suspension, 40 μl of $^{125}$I-endothelin-1 (12000–18000 cpm) was added. These mixtures were incubated at 25° C. for 4 hours, then subjected to filtration on a glass filter GF/C and then washed with 5 mM HEPES/Tris, pH 7.4, containing 0.3% bovine serum albumin. Then, the radioactivity trapped by the glass filter was measured, and the $^{125}$I-endothelin-1 binding inhibition D (%) at 1.1 μM of the test compound was determined by the following equation.

$$D(\%) = 100 - \frac{(C)-(A)}{(B)-(A)} \times 100$$

Each test was performed in triplicate.

TABLE 8

| $^{125}$I-endothelin-1 binding inhibition by 1.1 μM of the test compound | |
|---|---|
| Compd No. | Inhibition (%) |
| 1 | 90 |
| 2 | 84 |
| 3 | 75 |
| 4 | 99 |
| 5 | 97 |
| 6 | 64 |
| 7 | 78 |
| 8 | 81 |
| 9 | 54 |
| 10 | 81 |
| 11 | 41 |
| 12 | 77 |
| 13 | 26 |
| 14 | 65 |
| 15 | 89 |
| 16 | 18 |
| 17 | 18 |
| 18 | 94 |
| 19 | 61 |
| 20 | 75 |
| 21 | 94 |
| 22 | 93 |
| 23 | 100 |
| 24 | 97 |
| 25 | 88 |
| 26 | 85 |
| 27 | 83 |
| 28 | 99 |
| 29 | 89 |
| 30 | 73 |
| 31 | 96 |
| 32 | 72 |
| 33 | 99 |
| 34 | 99 |
| 35 | 97 |
| 36 | 95 |
| 37 | 90 |
| 38 | 84 |
| 39 | 98 |
| 40 | 99 |
| 41 | 67 |
| 42 | 97 |
| 43 | 99 |
| 44 | 97 |
| 45 | 71 |
| 46 | 91 |
| 47 | 35 |
| 48 | 92 |
| 49 | 99 |
| 50 | 99 |
| 51 | 99 |

TABLE 8-continued

| $^{125}$I-endothelin-1 binding inhibition by 1.1 μM of the test compound | |
|---|---|
| Compd No. | Inhibition (%) |
| 52 | 100 |
| 53 | 100 |
| 54 | 97 |
| 55 | 100 |
| 56 | 70 |
| 57 | 89 |
| 58 | 98 |
| 59 | 95 |
| 60 | 95 |
| 61 | 64 |
| 62 | 75 |
| 63 | 82 |
| 64 | 77 |
| 66 | 91 |
| 67 | 100 |
| 68 | 100 |
| 69 | 100 |
| 70 | 100 |
| 71 | 60 |
| 72 | 86 |
| 73 | 35 |
| 74 | 44 |
| 75 | 42 |
| 76 | 33 |
| 77 | 69 |
| 78 | 84 |
| 79 | 96 |
| 80 | 94 |
| 81 | 18 |
| 82 | 50 |
| 83 | 57 |
| 84 | 98 |
| 85 | 98 |
| 86 | 94 |
| 87 | 99 |
| 88 | 96 |
| 89 | 96 |
| 90 | 100 |
| 91 | 94 |
| 92 | 59 |
| 93 | 80 |
| 94 | 86 |
| 95 | 100 |
| 96 | 51 |
| 97 | 58 |
| 98 | 98 |
| 99 | 99 |
| 100 | 96 |
| 101 | 98 |
| 102 | 92 |
| 103 | 94 |
| 104 | 74 |
| 105 | 100 |
| 106 | 99 |
| 107 | 100 |
| 108 | 99 |
| 109 | 99 |
| 110 | 98 |
| 111 | 99 |
| 112 | 97 |
| 113 | 93 |
| 114 | 98 |
| 115 | 88 |

As shown in Table 8, the compounds of the present invention were found to be very potent inhibitor of endothelin binding to $ET_B$ receptor. The test compounds are indicated by compound Nos.

On the other hand, each of the representative compounds (Reference Compounds 1, 2 and 3) of the endothelin antagonistic peptides described in EP 0460679A2 showed, at a concentration of 1.1 μM, 69, 77 or 86% of the $^{125}$I-ET-1 binding inhibition to porcine aorta membrane suspension containing a large amount of $ET_A$ receptors, and, on the contrary, only 6.4, 3.8 or 10.1% of the $^{125}I$-ET-1 binding inhibition to $ET_B$ receptors of porcine cerebellum membrane suspension used in the present experiments.

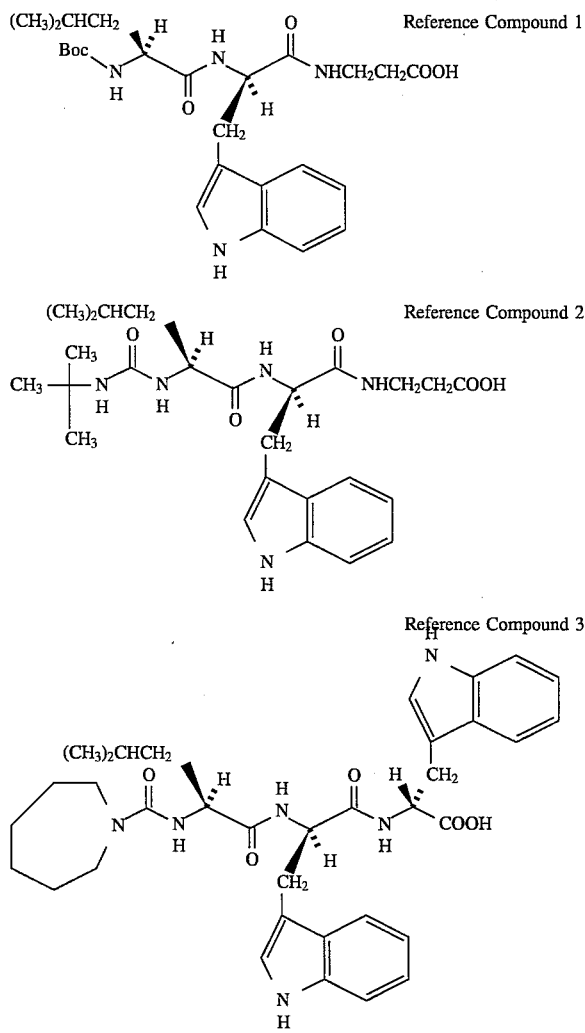

Activities Against Endothelin-induced Contraction of Isolated Rabbit Pulmonary Arteries The pulmonary artery of rabbit was isolated, and a spiral preparation having a width of 1 mm and a length of 10 mm was prepared therefrom. The preparation having the endothelial cells denuded, was placed in a 5 ml organ bath filled with a Krebs-Henseleit solution saturated with a gas mixture of 95% $O_2$ and 5% $CO_2$, and a change in the tension was isometrically measured and recorded.

Endothelin-3 was added into the organ bath in a cumulatively increasing manner, whereby the influence of a compound of the present invention to the concentration-response curve for endothelin-3 was examined. The compound was added into the organ bath 20 minutes prior to the addition of endothelin-3.

Figure 2:
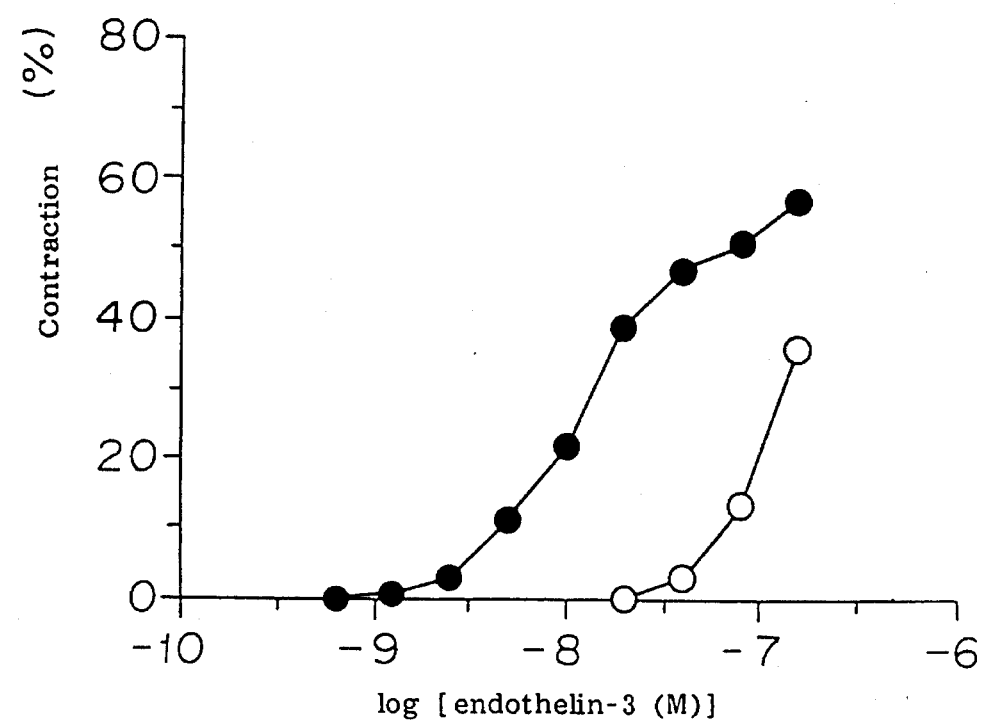
FIG. 2 shows the activities of 10 μM of Compound 39 (o) against endothelin-3-induced contraction of isolated guinea pig bronchial tube as compared with the case in which no drug is present (●).
Figure 3:
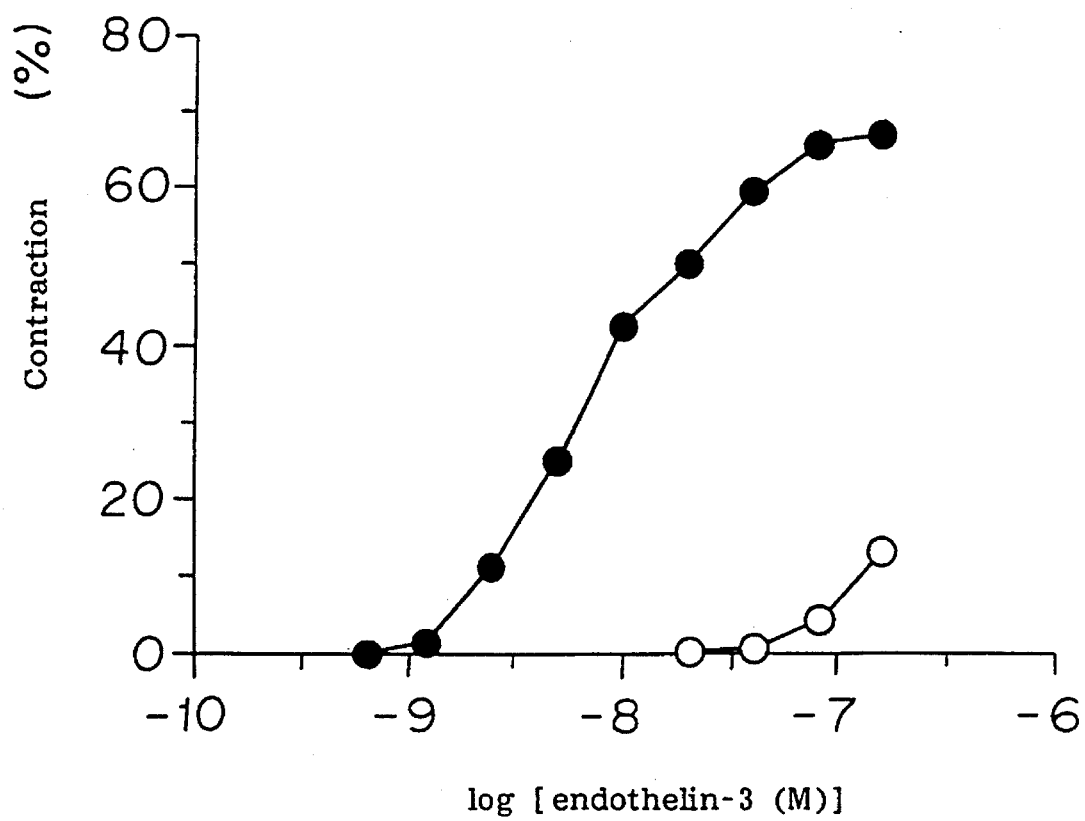
FIG. 3 shows the activities of 10 μM of Compound 40 (o) against endothelin-3-induced contraction of isolated guinea pig bronchial tube as compared with the case in which no drug is present (●).

As shown in FIGS. 1 to 3, Compound 4, Compound 39 and Compound 40 (0.1 to 10 μM) remarkably shifted the concentration-response curves of endothelin-3 to the right. Table 9 shows $pA_2$ values (−log of the concentration of the compound necessary for shifting the concentration-response curve for endothelin-3 twice to the right. Further, the compounds showed no effects to the isolated pulmonary artery when applied alone. As is evident from the above, the compounds showed remarkable antagonistic activities against endothelin-induced concentration of isolated rabbit pulmonary artery.

TABLE 9

Antagonistic activities of the compound of the present invention against endothelin-3-induced contraction of isolated rabbit pulmonary artery

| Compound No. | $PA_2$ value |
|---|---|
| 4 | 6.7 |
| 39 | 6.7 |
| 40 | 7.1 |

Activities Against Endothelin-induced Contraction of Isolated Guinea Pig Bronchus The bronchus of a guinea pig was isolated, and the bronchus was cut into rings having an outer diameter of 2 nun and a width of 4 mm to afford a preparation. The preparation was placed in a 5 ml organ bath filled with a Krebs.Henseleit solution saturated with a gas mixture of 95% $O_2$ and 5% $CO_2$, and a change in the tension was isometrically measured and recorded.

Endothelin-3 was added into the organ bath in a cumulatively increasing manner, and the influence of a compound of the present invention to the concentration-response curve for endothelin was examined. The compound was added into the organ bath 20 minutes prior to the addition of endothelin-3.

As shown in FIGS. 1 to 3, Compound 4, Compound 39 and Compound 40 (10 μM) remarkably shifted to concentration-response curves for endothelin-3 to the right in isolated bronchus. Further, the compounds showed no effects to the isolated bronchus when applied alone. As is evident from the foregoing, the compounds showed remarkable antagonistic activities against endothelin-induced contraction of isolated guinea pig bronchus.

Thus, the compounds of the present invention have excellent endothelin antagonistic activities and are useful as vasodilators for bronchodilators in the field of medicines, and they can be drugs for treating hypertension, pulmonary hypertension, Raynaud's disease, acute renal failure, myocardial infarction, angina pectoris, cerebral infarction, cerebral vasospasm, arteriosclerosis, asthma, gastric ulcer, diabetes, endotoxin shock endotoxin-induced multiple organ failure or disseminated intravascular coagulation, and/or cyclosporin-induced renal failure or hypertension. When used as drugs for treating such diseases, the compounds of the present invention can be used alone or in combination with other drugs for treatment.

The compounds of the present invention may be used in the form of drug formulations suitable for parenteral administration, oral administration or external administration by mixing them with solid or liquid excipient carriers known in this field. The drug formulations include a liquid formulation such as an injection formulation, an inhalant formulation, a syrup formulation or an emulsion, a solid formulation such as tablets, capsules or granules, and an external drug such as an ointment or a suppository. Further, these drug formulations may contain additives which are commonly employed, such as an adjuvant, a stabilizer, a wetting agent, an emulsifier, an absorption-promoting agent or a surfactant, as the case requires. As the additives, distilled water for injection, physiological saline, Ringer's solution, glucose, sugar syrup, gelatin, vegetable oil, cacao butter, ethylene glycol, hydroxypropyl cellulose, lactose, sucrose, corn starch, magnesium stearate and talc may be mentioned.

The dose of a compound of the present invention as an endothelin antagonist varies depending upon the manner of administration, the age and body weight of the patient and the condition of the patient to be treated. However, a typical administration method for an adult is oral administration or parenteral administration. The daily dose in the case of oral administration to an adult patient is from 0.1 to 100 mg/kg body weight, and the daily dose in the case of parenteral administration is from 0.01 to 10 mg/kg body weight.

The following Examples and Referential Examples illustrate the present invention more specifically. It should be understood that the present invention is not limited to these examples alone.

EXAMPLE 1

Synthesis of Compound 1

(1) Preparation of Boc-Leu-DTrp(COOMe)-OH

To a mixture of Boc-Leu-OH.H$_2$O (2.5 g), H-DTrp-OBzl (2.9 g) and HOBT.H$_2$O (1.6 g) in dichloromethane (50 ml) was added EDCI.HCl (2.0 g) under ice cooling. After being stirred at room temperature for 16 h, the mixture was washed with water, 10% aq. citric acid, sat. aq. NaHCO$_3$ and brine successively, dried over MgSO$_4$ and evaporated in vacuo. The residue was triturated with hexane to give Boc-Leu-DTrp-OBzl (4.79 g). To a solution of the dipeptide (753 mg) in dichloromethane (7 ml) were added methyl chloroformate (1 ml), pulverized NaOH (89 mg) and TBAHS (20 mg) under ice cooling. After being stirred of the mixture at room temperature for 30 min, pulverized NaOH (89 mg) was added. This procedure was repeated twice more. The reaction mixture was diluted with dichloromethane, washed with sat. aq. NaHCO$_3$, 10% aq. citric acid, water and brine successively, dried over MgSO$_4$ and evaporated in vacuo. The residue was recrystallized from dichloromethane and petroleum ether to give Boc-Leu-DTrp(COOMe)-OBzl (721 mg) as colorless crystals. The dipeptide (708 mg) was dissolved in methanol (7 ml) - THF (5 ml) and 10% Pd/C (70 mg) was added. The mixture was vigorously stirred at room temperature under an atmospheric pressure of hydrogen for 1 h. The reaction mixture was filtered and the filtrate was evaporated in vacuo to give Boc-Leu-DTrp(COOMe)-OH (580 mg).

FAB-MS(m/e,(C$_{24}$H$_{33}$N$_3$O$_7$+H)$^+$):476

(2) Preparation of Boc-Leu-DTrp(COOMe)-DNle-OBzl

To a mixture of Boc-Leu-DTrp(COOMe)-OH (50 mg), H-DNle-OBzl.TsOH (46 mg), NMM (13 µl) and HOBT.H$_2$O (16 mg) in dichloromethane (1 ml) was added EDCI.HCl (22 mg) under ice cooling. After being stirred at room temperature for 2 h, the mixture was diluted with dichloromethane, washed with water, 10% aq. citric acid, sat. aq. NaHCO$_3$ and brine successively, dried over MgSO$_4$ and evaporated in vacuo. The residue was purified by preparative TLC (Merck, Kieselgel 60 F$_{254}$) with chloroform/methanol/acetic acid= 100/10/1 for development to give Boc-Leu-DTrp(COOMe)-DNle-OBzl (67 mg).

FAB-MS(m/e,(C$_{37}$H$_{50}$N$_4$O$_8$+H)$^+$):679

(3) Preparation of Compound 1

A solution of Boc-Leu-DTrp(COOMe)-DNle-OBzl (25 mg) in methanol (1 ml) was hydrogenated over 10% Pd/C at an atmospheric pressure of hydrogen for 1 h. After removal of the catalyst by filtration, the filtrate was concentrated in vacuo. The residue was purified by preparative TLC (3M, Empore Silica Sheet) with chloroform/methanol/acetic acid=100/10/1 for development and the product was reprecipitated from methanol and water to give Compound 1 (11 mg).

m.p.: 154°–163° C.
IR(KBr,cm$^{-1}$):
3328,2962,2872,1728,1695,1650,1536,1461,1386,1371, 1341,1311,1260,1167,1092,762,747

High Resolution FAB-MS(m/e,(C$_{30}$H$_{44}$N$_4$O$_8$+H)$^+$): Calcd: 589.3237 Found: 589.3260

$^1$H-NMR(300 MHz,DMSO-d$_6$,δ ppm): 0.65(6H,d,J=6.2 Hz),0.85(3H,t,J=7.0 Hz),0.93–1.10 (2H,m),1.10–1.55(5H, m),1.31(9H,s),1.55–1.82(2H,m),2.86 (1H,dd,J=10.6 Hz,15.2 Hz),3.00–3.30(1H,m),3.80–3.90 (1H,m),3.95(3H, s),4.05–4.20(1H,m),4.59–4.70 (1H,m),6.74(1H,d,J=7.1 Hz), 7.23(1H,t,J=7.5 Hz),7.31 (1H,t,J=7.5 Hz),7.49(1H,s), 7.70(1H,d,J=7.5 Hz),8.04 (2H,d,J=7.5 Hz),8.20(1H,d,J=8.3 Hz)

EXAMPLE 2

Synthesis of Compound 2

Compound 2 was prepared using H-DNle-OBzl.TsOH as a starting material in the same manner described Example 1-(2) and (3).

m.p.: 179°–185° C.
IR(KBr,cm$^{-1}$):
3322,2968,1720,1656,1530,1461,1389,1341,1311,1260, 1167,1092,765,747

High Resolution FAB-MS(m/e,(C$_{29}$H$_{42}$N$_4$O$_8$+H)$^+$): Calcd: 575.3080 Found: 575.3101

$^1$H-NMR(300 MHz,DMSO-d$_6$,δ ppm): 0.65(3H,d,J=7.2 Hz),0.66(3H,d,J=7.2 Hz),0–85(3H,t,J=7.2 Hz), 0.95–1.75(7H,m),1.31(9H,s),2.88(1H,dd,J=10.6 Hz,14.9 Hz),3.15(1H,dd,J=4.3 Hz,14.9 Hz),3.85 (1H,m),3.95(3H,s), 4.06(1H,dt,J=5.6 Hz,7.6 Hz),4.61 (1H,ddd,J=4.3 Hz,7.6 Hz,10.6 Hz),6.72(1H,d,J=7.6 Hz),7.23 (1H,t,J=7.6 Hz), 7.31(1H,t,J=7.6 Hz),7.48(1H,s),7.69 (1H,d,J=7.6 Hz), 7.93(1H,d,J=7.6 Hz),8.03(1H,d,J=7.6 Hz),8.19(1H,d,J=8.4 Hz)

EXAMPLE 3

Synthesis of Compound 3

(1) Preparation of Boc-Leu-DTrp(COOEt)-DNle-OBzl

The title compound was prepared using ethyl chloroformate instead of methyl chloroformate in the same manner described in Example 1-(1) and (2).

FAB-MS(m/e,(C$_{38}$H$_{52}$N$_4$O$_8$+H)$^+$):693

(2) Preparation of Compound 3

Compound 3 was prepared using Boc-Leu-DTrp-(COOEt)-DNle-OBzl as a starting material in the same manner described in Example 1-(3).

m.p.: 104°–105° C.
IR(KBr,cm$^{-1}$):
3322,2968,2872,1720,1662,1536,1461,1386,1254,1170,747

High Resolution FAB-MS(m/e,(C$_{31}$H$_{46}$N$_4$O$_8$+H)$^+$): Calcd: 603.3394 Found: 603.3406

$^1$H-NMR(300 MHz,DMSO-d$_6$,δ ppm): 0.65(6H,d,J=6.4 Hz),0.77–1.90(12H,m),1.31(9H,s),1.37 (3H,t,J=7.0 Hz), 2.88(1H,dd,J=10.7 Hz,15.4 Hz),3.15 (1H,dd,J=4.2 Hz,15.4 Hz),3.80–3.91(1H,m),4.05–4.25 (1H,m),4.40(2H,q,J=7.0 Hz),4.60–4.71(1H,m),6.73 (1H,d,J=7.6 Hz),7.23(1H,t,J=7.5

Hz),7.31(1H,t,J=7.5 Hz),7.51(1H,s),7.70(1H,d,J=7.5 Hz), 8.03(1H,d,J=7.5 Hz),8.06(1H,brs),8.19(1H,d,J=8.8 Hz)

EXAMPLE 4

Synthesis of Compound 4

A mixture of Boc-Leu-DTrp(COOMe)-DNle-OBzl (20 mg, prepared in Example 1-(2)) in TFA (0.5 ml) was stirred under ice cooling for 15 min and evaporated in vacuo. To a solution of the residue in chloroform (0.5 ml) were added TEA (6 µl) and 2-chlorophenylisocyanate (4 µl) under ice cooling. After being stirred at the same temperature for 1 h, the mixture was diluted with chloroform, washed with 1N-hydrochloric acid, 5% aq. NaHCO$_3$, and brine successively, dried over MgSO$_4$ and evaporated in vacuo. The residue was purified by preparative TLC (Merck, Kieselgel 60 F$_{254}$) with chloroform/methanol=50/1 for development, and the product was hydrogenated over 10% Pd/C at an atmospheric pressure of hydrogen for 1 h. The reaction mixture was filtered and the filtrate was evaporated in vacuo. The residue was purified by reverse phase MPLC (Merck, LiChroprep RP-18) with methanol/water=5/1 for elution to give Compound 4 (5 mg).

m.p.: 193°–201° C.

IR(KBr,cm$^{-1}$):
3328,2962,2872,1740,1647,1593,1548,1461,1446,1386, 1341,1311,1263,1230,1092,747

High Resolution FAB-MS(m/e,(C$_{32}$H$_{40}$ClN$_5$O$_7$+H)$^+$): Calcd: 642.2695 Found: 642.2661

$^1$H-NMR(300 MHz,DMSO-d$_6$,δ ppm): 0.65(3H,d,J=5.8 Hz),0.67(3H,d,J=5.8 Hz),0–82(3H,t,J=7.1 Hz), 1.00–1.40(7H,m),1.57–1.80(2H,m),2.89 (1H,dd,J=3.2 Hz,11.5 Hz),3.10–3.20(1H,m),3.95(3H,s),4.08–4.22 (2H, m),4.62–4.72(1H,m),6.91(1H,dt,$^J$=1.4 Hz,7.8 Hz), 7.14–7.32(4H,m),7.35(1H,dd,J=1.4 Hz,7.8 Hz),7.54 (1H,s), 7.76(1H,d,J=7.8 Hz),8.05(1H,d,J=7.8 Hz),8.08 (1H,dd,J= 1.4 Hz,7.8 Hz),8.11(1H,s),8.13–8.20 (1H,m),8.50(1H,d,J= 8.8 Hz)

EXAMPLE 5

Synthesis of Compound 5

Compound 5 was prepared using Boc-Leu-DTrp(COOEt)-DNle-OBzl as a starting material in the same manner described in Example 4.

m.p.: 161°–168° C.

IR(KBr,cm$^{-1}$):
3328,2962,2872,1740,1644,1593,1551,1461,1446,1206, 1092,747

High Resolution FAB-MS(m/e,(C$_{33}$H$_{42}$ClN$_5$O$_7$+H)$^+$): Calcd: 656.2852 Found: 656.2851

$^1$H-NMR(300 MHz,DMSO-d$_6$,δ ppm): 0.65(3H,d,J=6.4 Hz),0.66(3H,d,J=6.4 Hz),0.82(3H,t,J=7.2 Hz), 0.88–1.80(9H,m),1.38(3H,t,J=7.0 Hz),2.90 (1H,dd,J=11.8 Hz,14.4 Hz),3.15(1H,dd,J=2.7 Hz,14.4 Hz),4.10–4.25 (2H, m),4.41(2H,q,J=7.0 Hz),4.64–4.75(1H,m),6.86 (1H,s), 6.91(1H,dt,J=1.6 Hz,7.6 Hz),7.12–7.40 (5H,m),7.56(1H,s), 7.75(1H,d,J=7.1 Hz),8.05(1H,d,J=7.1 Hz),8.09(1H,d,J=10.1 Hz),8.17(1H,d,J=7.9 Hz),8.47 (1H,d,J=8.8 Hz)

EXAMPLE 6

Synthesis of Compound 6

To a solution of Boc-Leu-DTrp(COOMe)-OH (104 mg, prepared in Example 1-(1)) in DMF (3.5 ml) were added HOSu (51 mg) and EDCI.HCl (64 mg) under ice cooling. The mixture was stirred at the same temperature for 1.5 h and at room temperature for 5 h. To the mixture was added an aqueous solution of H-DMet-ONa (prepared from DMet (49 mg) and sodium bicarbonate (28 mg) in water (2 ml)) under ice cooling. After being stirred at room temperature for 2 h, the reaction mixture was diluted with ethyl acetate, washed with 10% aq. citric acid and brine successively, dried over MgSO$_4$ and evaporated in vacuo. The residue was purified by reverse phase chromatography (Nacalai Tesque, Cosmosil 75C18-OPN) with methanol/water=7/3–8/2 for elution to give Compound 6 (65 mg).

m.p.: 140°–143° C.

IR(KBr,cm$^{-1}$):
3322,2962,1740,1653,1533,1461,1389,1341,1260,1167, 1092,762,747

High Resolution FAB-MS(m/e,(C$_{29}$H$_{42}$N$_4$O$_8$S+H)$^+$): Calcd: 607.2801 Found: 607.2761

$^1$H-NMR(300 MHz,DMSO-d$_6$,δ ppm): 0.65(6H,d,J=5.9 Hz),1.00–1.25(3H,m),1.32(9H,s),1.85–2.05 (2H,m), 2.04(3H,s),2.52–2.75(2H,m),2.87(1H,dd,J=10.7 Hz,15.4 Hz),3.16(1H,dd,J=6.2 Hz,15.4 Hz),3.78–3.85 (1H,m), 3.95(3H,s),4.28–4.37(1H,m),4.59–4.70 (1H,m),6.79(1H,d, J=7.6 Hz),7.25(1H,t,J=7.6 Hz),7.32 (1H,t,J=7.6 Hz), 7.50(1H,s),7.69(1H,d,J=7.6 Hz),8.04 (1H,d,J=7.6 Hz), 8.11(1H,d,J=8.4 Hz),8.22(1H,d,J=8.3 Hz)

Each Compound 7–12 described in the following Examples 7–12 was prepared using each corresponding amino acid sodium salt as a starting material in the same manner described in Example 6.

EXAMPLE 7

Compound 7 m.p.: 147°–150° C.

IR(KBr,cm$^{-1}$):
334,2962,1740,1650,1553,1461,1386,1341,1311,1260,1167, 1092,767,747

High Resolution FAB-MS(m/e,(C$_{28}$H$_{40}$N$_4$O$_8$S+H)$^+$): Calcd: 593.2645 Found: 593.2628

$^1$H-NMR(300 MHz,DMSO-d$_6$,δ ppm): 0.65(3H,d,J=6.3 Hz),0.66(3H,d,J=5.4 Hz),0.70–1.15 (3H,m),1.31(9H,s), 2.09(3H,s),2.75–2.92(3H,m),3.15 (1H,dd,J=3.5 Hz,14.9 Hz),3.85–3.94(1H,m),3.95(3H,s),4.42 (1H,dt,J=5.0 Hz,7.6 Hz),4.64–4.73(1H,m),6.72(1H,d,J=7.6 Hz),7.24(1H,t,J=7.4 Hz),7.31(1H,t,J=7.4 Hz),7.50 (1H,s),7.72(1H,d,J=7.4 Hz), 8.04(1H,d,J=7.4 Hz),8.20 (1H,d,J=8.5 Hz),8.36(1H,d,J=7.8 Hz)

EXAMPLE 8

Compound 8 m.p.: 170°–173° C.

IR(KBr,cm$^{-1}$):
3346,2968,1743,1650,1611,1530,1461,1389,1341,1260, 1170,1092,762,747

High Resolution FAB-MS(m/e,(C$_{29}$H$_{42}$N$_4$O$_8$S+H)$^+$): Calcd: 607.2802 Found: 607.2792

¹H-NMR(300 MHz,DMSO-d₆,δ ppm): 0.65(3H,d,J=6.4 Hz),0.67(3H,d,J=3.9 Hz),0.70–1.20 (3H,m),1.16(3H,t,J=7.3 Hz),1.31(9H,s),2.53(2H,q,J=7.3 Hz),2.78–2.97(3H,m), 3.14(1H,dd,J=3.6 Hz,14.7 Hz),3.82–3.96(1H,m),3.95(3H,s), 4.36(1H,dt,J=5.4 Hz,7.8 Hz),4.62–4.75(1H,m),6.69(1H,d,J= 7.8 Hz),7.24 (1H,t,J=7.3 Hz),7.31(1H,t,J=7.3 Hz),7.50(1H, s),7.72 (1H,d,J=7.3 Hz),8.03(1H,d,J=7.3 Hz),8.18(1H,d,J= 8.9 Hz),8.31(1H,d,J=7.9 Hz)

EXAMPLE 9

Compound 9 m.p.: 106°–108° C.

IR(KBr,cm⁻¹):
3322,2968,1737,1695,1653,1530,1461,1386,1341,1311, 1260,1167,1092,765,747

High Resolution FAB-MS(m/e,(C₃₀H₄₄N₄O₈S+H)⁺): Calcd: 621.2958 Found: 621.2938

¹H-NMR(300 MHz,DMSO-d₆,δ ppm): 0.65(3H,d,J=6.4 Hz),0.66(3H,d,J=6.4 Hz),0.91(3H,t,J=7.3 Hz), 0.98–1.28(3H,m),1.31(9H,s),1.52(2H,sext,J=7.3 Hz), 2.48–2.53(2H,m),2.75–2.95(3H,m),3.15(1H,dd,J=4.2 Hz,15.4 Hz),3.85–3.94(1H,m),3.95(3H,s),4.32–4.40 (1H, m),4.65–4.72(1H,m),6.70(1H,d,J=7.8 Hz),7.24 (1H,t,J=7.4 Hz),7.31(1H,t,J=7.4 Hz),7.50(1H,s),7.72 (1H,d,J=7.4 Hz), 8.04(1H,d,J=7.4 Hz),8.18(1H,d,J=8.3 Hz),8.33(1H,d,J=7.0 Hz)

EXAMPLE 10

Compound 10 m.p.: 188°–190° C.

IR(KBr,cm⁻¹):
3304,2962,1740,1653,1533,1461,1386,1341,1260,1167, 1092,765,747

High Resolution FAB-MS(m/e,(C₂₉H₄₀N₄O₈+H)⁺): Calcd: 573.2924 Found: 573.2919

¹H-NMR(300 MHz,DMSO-d₆,δ ppm): 0.65(6H,d,J=6.1 Hz),0.94–1.30(3H,m),1.32(9H,s),2.37–3.52 (2H,m), 2.87(1H,dd,J=10.7 Hz,15.4 Hz),3.16(1H,dd,J=4.2 Hz,15.4 Hz),3.82–3.90(1H,m),3.95(3H,s),4.24–4.31 (1H,m), 4.60–4.72(1H,m),5.05(1H,dd,J=1.7 Hz,9.8 Hz),5.12(1H,dd, J=1.7 Hz,17.7 Hz),5.72–5.85(1H,m),6.75 (1H,d,J=7.6 Hz), 7.24(1H,t,J=7.3 Hz),7.32(1H,t,J=7.3 Hz),7.50(1H,s), 7.70(1H,d,J=7.3 Hz),8.04(1H,d,J=7.3 Hz),8.16(1H,d,J=8.7 Hz),8.20(1H,d,J=8.5 Hz)

EXAMPLE 11

Compound 11 m.p.: 99°–126° C.(dec.)

IR(KBr,cm⁻¹):
3304,2962,1740,1656,1553,1461,1389,1260,1167,1092, 1047,765,747

High Resolution FAB-MS(m/e,(C₃₀H₄₄N₄O₈+H)⁺): Calcd: 589.3273 Found: 589.3243

¹H-NMR(300 MHz,DMSO-d₆,δ ppm): 0.66(3H,d,J=6.4 Hz),0.67(3H,d,J=6.4 Hz),0.70–1.73 (12H,m),1.31(9H,s), 2.88(1H,dd,J=10.7 Hz,15.4 Hz),3.15 (1H,dd,J=4.2 Hz,15.4 Hz),3.82–4.00(1H,m),3.95(3H,s),4.00–4.12 (1H,m), 4.51–4.68(1H,m),6.69(1H,d,J=7.6 Hz),7.23 (1H,t,J=7.9 Hz),7.29(1H,t,J=7.9 Hz),7.48(1H,s),7.69 (1H,d,J=7.9 Hz), 7.80(1H,d,J=8.8 Hz),8.03(1H,d,J=7.9 Hz),8.16(1H,d,J=7.8 Hz)

EXAMPLE 12

Compound 12 m.p.: 185°–189° C.

IR(KBr,cm⁻¹):
3310,2968,1740,1656,1539,1461,1386,1260,1170,1092, 1047,765,747

High Resolution FAB-MS(m/e,(C₃₀H₄₄N₄O₈+H)⁺): Calcd: 589.3237 Found: 589.3227

¹H-NMR(300 MHz,DMSO-d₆,δ ppm): 0.65(3H,d,J=6.5 Hz),0.68(3H,d,J=6.5 Hz),0.79(3H,d,J=6.8 Hz),0.84(3H,t,J= 7.3 Hz),0.93–1.60(6H,m),1.31 (9H,s),2.92(1H,dd,J=10.7 Hz,15.4 Hz),3.12(1H,dd,J=4.2 Hz,15.4 Hz),3.85–4.02(1H, m),3.95(3H,s),4.06–4.17 (1H,m),4.56–4.69(1H,m),6.66(1H, d,J=8.6 Hz),7.23 (1H,t,J=7.3 Hz),7.30(1H,t,J=7.3 Hz), 7.50(1H,s),7.53 (1H,d,J=8.5 Hz),7.68(1H,d,J=7.3 Hz), 8.03(1H,d,J=7.3 Hz),8.16(1H,d,J=7.8 Hz)

EXAMPLE 13

Synthesis of Compound 13

To a solution of Boc-Leu-DTrp(COOMe)-OH (25 mg, prepared in Example 1-(1)) in dichloromethane (0.5 ml) were added D-norleucinol hydrochloride (12 mg), NMM (8.5 μl), HOBT.H₂O (8 mg) and EDCI.HCl (15 mg) successively under ice cooling. The mixture was stirred at 0°–5° C. for 10 min and at room temperature for 1 h. The reaction mixture was diluted with ethyl acetate, washed with 4% aq. NaHCO₃, 10% aq. citric acid, water and brine successively, dried over MgSO₄ and evaporated in vacuo. The residue was purified by preparative TLC (Merck, Kieselgel 60 F₂₅₄) with chloroform/methanol=10/1 for development to give Compound 13 (26 mg).

m.p.: 141°–148° C.

IR(KBr,cm⁻¹):
3304,2962,1743,1647,1536,1461,1386,1371,1341,1311, 1260,1170,1092,762,747

High Resolution FAB-MS(m/e,(C₃₀H₄₆N₄O₇+H)⁺): Calcd: 575.3444 Found: 575.3481

¹H-NMR(300 MHz,DMSO-d₆,δ ppm): 0.69–0.95(9H,m), 0.96–1.70(17H,m),2.88(1H,dd,J=10.5 Hz,14.2 Hz), 3.08–3.25(2H,m),3.60–3.76(1H,m),3.76–3.88 (1H,m), 3.95(3H,s),4.42–4.66(3H,m),6.80 (1H,d,J=6.9 Hz),7.24(1H, t,J=7.4 Hz),7.32(1H,t,J=7.4 Hz),7.48(1H,s),7.49(1H,d,J=7.4 Hz),7.67(1H,d,J=7.4 Hz),8.04(1H,d,J=9.1 Hz),8.18(1H,d,J= 8.4 Hz)

EXAMPLE 14

Synthesis of Compound 14

(1) Preparation of Boc-DTrp-DNle-OBzl

To a solution of H-DNle-OBzl.TsOH (1.27 g) in dichloromethane (20 ml) were added NMM (0.53 ml), Boc-DTrp-OH (1.22 g), HOBT.H₂O (734 mg) and EDCI.HCl (926 mg) successively under ice cooling. The mixture was stirred at the same temperature for 1 h and at room s temperature for 2 h. The mixture was diluted with ethyl acetate, washed with sat. aq. NaHCO₃, 10% aq. citric acid, and brine successively, dried over MgSO₄ and evaporated in vacuo. The residue was recrystallized from ethyl acetate and hexane to give Boc-DTrp-DNle-OBzl (1.56 g).

FAB-MS(m/e,(C₂₉H₃₇N₃O₅+H)⁺):508

(2) Preparation of Boc-DTrp(COOMe)-DNle-OBzl

To a solution of the dipeptide obtained in (1) (1.00 g) in dichloromethane (20 ml) were added pulverized NaOH (118 mg), TBAHS (134 mg) and methyl chloroformate (228 μl) at room temperature under argon atmosphere. After being stirred at room temperature for 8 h, the reaction mixture was diluted with dichloromethane, washed with 10% aq. citric acid, sat. aq. $NaHCO_3$, water and brine successively, dried over $MgSO_4$ and evaporated in vacuo to give Boc-DTrp-(COOMe)-DNle-OBzl (1.11 g).

FAB-MS(m/e,$(C_{31}H_{39}N_3O_7+H)^+$):565

(3) Preparation of Compound 14

A mixture of Boc-DTrp(COOMe)-DNle-OBzl (83 mg) in TFA (2 ml) was stirred at room temperature for 1 h and evaporated in vacuo. To a solution of the residue in DMF (0.6 ml) were added NMM (18 μl), Boc-Nle-OH (51 mg) and EDCI.HCl (43 mg) successively under ice cooling. The mixture was stirred at the same temperature for 1 h and at room temperature for 12 h. The mixture was diluted with ethyl acetate, washed with sat. aq. $NaHCO_3$, 10% aq. citric acid, water and brine successively, dried over $MgSO_4$ and evaporated in vacuo. The residue was purified by MPLC (Merck, LiChroprep Si 60) with chloroform/methanol= 500/6 for elution to give Boc-Nle-DTrp(COOMe)-DNle-OBzl (88 mg). A solution of the tripeptide derivative (22.4 mg) in methanol was hydrogenated over 10% Pd/C (10 mg) at an atmospheric pressure of hydrogen for 2 h. After removal of the catalyst by filtration, the filtrate was concentrated in vacuo. The residue was purified by preparative TLC (3M, Empore Silica Sheet) with chloroform/methanol=20/1 for development to give Compound 14 (14 mg).

m.p.: 152°–159° C.

IR(KBr,$cm^{-1}$):
3322,2962,2872,1725,1656,1539,1461,1386,1371,1341, 1311,1260,1167,1092,762,747

High Resolution FAB-MS(m/e,$(C_{30}H_{44}N_4O_8+H)^+$): Calcd: 589.3237 Found: 589.3248

$^1$H-NMR(300 MHz,DMSO-$d_6$,δ ppm): 0.64(3H,d,J=7.2 Hz),0.78–1.82(12H,m),0.85(3H,t,J=6.9 Hz),1.32(9H,s), 2.87(1H,dd,J=10.4 Hz,14.8 Hz),3.10–3.30 (1H,m), 3.76–3.90(1H,m),3.95(3H,s),4.45–4.60 (1H,m), 4.60–4.72(1H,m),6.68(1H,d,J=6.8 Hz),7.24 (1H,t,J=7.4 Hz),7.31(1H,t,J=7.4 Hz),7.51(1H,s),7.71 (1H,d,J=7.4 Hz), 8.02(1H,d,J=7.4 Hz),8.03(1H,d,J=8.1 Hz),8.18(1H,d,J=7.8 Hz)

EXAMPLE 15

Synthesis of Compound 15

Compound 15 was prepared using Boc-γMeLeu instead of Boc-Nle in the same manner described in Example 14-(3).

m.p.: 118°–125° C.

IR(KBr,$cm^{-1}$):
3328,2962,2872,1720,1698,1660,1539,1494,1461,1395, 1371,1341,1257,1197,1170,1092,1053,765,750

High Resolution FAB-MS(m/e,$(C_{31}H_{46}N_4O_8+H)^+$): Calcd: 603.3394 Found: 603.3412

$^1$H-NMR(300 MHz,DMSO-$d_6$,δ ppm): 0.71(3H,t,J=7.7 Hz),0.88(9H,s),1.00–1.98(8H,m),1.31 (9H,s),2.90(1H,dd,J= 10.5 Hz,14.8 Hz),3.11(1H,dd,J=3.9 Hz,14.8 Hz), 3.60–3.85(1H,m),3.94(3H,s),4.35–4.68 (2H,m),6.73(1H,d, J=8.3 Hz),7.24(1H,t,J=7.5 Hz),7.31 (1H,t,J=7.5 Hz), 7.52(1H,s),7.72(1H,d,J=7.5 Hz),8.03 (1H,d,J=7.5 Hz), 8.12(1H,d,J=7.4 Hz),8.23(1H,d,J=7.6 Hz)

EXAMPLE 16

Synthesis of Compound 16

(1) Preparation of Boc-DNal-DNle-OBzl

Boc-DNal-DNle-OBzl was prepared using Boc-DNal-OH instead of Boc-DTrp-OH in the same manner described in Example 14-(1).

FAB-MS(m/e,$(C_{31}H_{38}N_2O_5+H)^+$):519

(2) Preparation of H-DNal-DNle-OBzl

To a solution of Boc-DNal-DNle-OBzl (233 mg) in dichloromethane (2 ml) was added TFA (5 ml) and the mixture was stirred at room temperature for 13 h. The mixture was concentrated in vacuo. The residue was dissolved in dichloromethane, washed with sat. aq. $NaHCO_3$, water and brine successively, dried over $MgSO_4$ and evaporated in vacuo to give the product (185 mg).

FAB-MS(m/e,$(C_{26}H_{30}N_2O_3+H)^+$):419

(3) Preparation of Compound 16

To a solution of H-DNal-DNle-OBzl (180 mg, prepared in (2)) in dichloromethane (5 ml) were added Boc-Leu-OH.$H_2O$ (180 mg), HOBT.$H_2O$ (70 mg) and EDCI.HCl (99 mg) successively under ice cooling. After being stirred at room temperature for 14 h, the mixture was diluted with ethyl acetate, washed with sat. aq. $NaHCO_3$, 10% aq. citric acid, water and brine successively, dried over $MgSO_4$ and evaporated in vacuo. The residue was purified by dry column flash chromatography (Merck, Kieselgel 60) with ethyl acetate/hexane=1/2 for elution to give Boc-Leu-DNal-DNle-OBzl (239 mg). A solution of the tripeptide derivative (87 mg) in 95% ethanol (10 ml) was hydrogenated over 10% Pd/C (21 mg) at an atmospheric pressure of hydrogen for 1 h. After removal of the catalyst by filtration, the filtrate was concentrated in vacuo to give Compound 16 (74 mg).

m.p.: 88°–90° C.

IR(KBr,$cm^{-1}$):
3304,3070,2962,2872,1725,1698,1656,1536,1461,1398, 1371,1251,1167,777

High Resolution FAB-MS(m/e,$(C_{30}H_{43}N_3O_6+H)^+$): Calcd: 542.3230 Found: 542.3223

$^1$H-NMR(300 MHz,$CDCl_3$,δ ppm): 0.77–0.97(9H,m), 1.12–1.89(9H,m),1.39+1.45(9H,s×2),3.48–3.66 (2H,m), 3.92–3.99(1H,m),4.33–4.40(1H,m),4.82–4.90 (1H,m), 5.07(1H,brs),6.81(1H,brd,J=5.4 Hz),6.85 (1H,brs), 7.32–7.38(2H,m),7.46(1H,dd,J=8.0 Hz,7.0 Hz),7.53(1H,dd, J=8.0 Hz,7.0 Hz),7.69–7.75(1H,m),7.82 (1H,d,J=8.0 Hz), 8.16(1H,d,J=8.0 Hz)

EXAMPLE 17

Synthesis of Compound 17

Compound 17 was prepared using DLTrp(Me) instead of DNal in the same manner described in Example 16.

m.p.: 91°–98° C.

IR(KBr,$cm^{-1}$):
3322,2962,1653,1530,1476,1371,1251,1167,738

High Resolution FAB-MS(m/e,$(C_{29}H_{44}N_4O_6+H)^+$): Calcd: 545.3339 Found: 545.3311

$^1$H-NMR(300 MHz,DMSO-$d_6$,70° C.,δ ppm): 0.75(3H,d, J=6.3 Hz),0.78–0.89(6H,m),1.09–1.72(9H,m),1.34+1.36 (9H,s×2),2.81–3.10(2H,m),3.69+3.70(3H,s×2 ),3.88–3.94(1H,m),4.10–4.22(1H,m),4.55–4.61 (1H,m), 6.45+6.60(1H,brs×2),6.98(1H,t,J=8.1 Hz),7.02+7.05 (1H,s× 2),7.10(1H,t,J=8.1 Hz),7.32(1H,d,J=8.1 Hz),7.53–7.78(2H, m),7.54+7.57(1H,d×2,J=8.1 Hz)

EXAMPLE 18

Synthesis of Compound 18

(1) Preparation of H-DBal-DNle-O$^t$Bu

To a solution of Boc-DBal-OH (80 mg) in dichloromethane (10 ml) were added H-DNle-O$^t$Bu (67 mg), HOBT.H$_2$O (41 mg) and EDCI.HCl (58 mg) successively at room temperature. After being stirred at room temperature for 6 h, the mixture was diluted with dichloromethane, washed with sat. aq NaHCO$_3$, 10% aq. citric acid, water and brine successively, dried over MgSO$_4$ and evaporated in vacuo. The residue was purified by silica gel flash chromatography (Merck, Kieselgel 60) with chloroform for elution to give an oily product (123 mg), which was dissolved in formic acid. The mixture was stirred at room temperature for 2 h. The mixture was diluted with ethyl acetate, washed with sat. aq. NaHCO$_3$ and brine, dried over MgSO$_4$ and evaporated in vacuo to give H-DBal-DNle-O$^t$Bu (97 mg).

FAB-MS(m/e, (C$_{21}$H$_{30}$N$_2$O$_3$S+H)$^+$):391

(2) Preparation of (2-chlorophenyl)carbamoyl-Leu-OH (2-Chlorophenyl)carbamoyl-Leu-OH was prepared using H-Leu-OBzl-TsOH as a starting material in the same manner described in Example 4.

FAB-MS(m/e, (C$_{13}$H$_{17}$C$_1$N$_2$O$_3$+H)$^+$):285

(3) Preparation of Compound 18

To a solution of H-DBal-DNle-O$^t$Bu (98 mg, prepared in (1)) in DMF (10 ml) were added (2-chlorophenyl)carbamoyl-Leu-OH (85 mg, prepared in (2)), HOBT.H$_2$O (46 mg) and EDCI.HCl (62 mg) successively under ice cooling. After being stirred at room temperature for 11 h, the reaction mixture was concentrated under reduced pressure. The residue was dissolved in chloroform and the solution was washed with sat. aq. NaHCO$_3$, 10% aq.citric acid and brine successively, dried over MgSO$_4$ and evaporated to give a corresponding tripeptide derivative (148 mg). The tripeptide (102 mg) was dissolved in TFA (2 ml). The solution was stirred at room temperature for 2 h and evaporated in vacuo. The residue was purified by reprecipitation from methanol and water to give Compound 18 (81 mg).

m.p.: 182°–183° C.

IR(KBr,cm$^{-1}$):
3304,3076,2962,1716,1644,1590,1551,1443,750,729

High Resolution FAB-MS(m/e,(C$_{30}$H$_{37}$C$_1$N$_4$O$_5$S+H)$^+$): Calcd: 601.2252 Found: 601.2255

$^1$H-NMR(300 MHz,CDCl$_3$,δ ppm): 0.77–0.82(9H,m), 0.88–1.65(9H,m),3.32(1H,dd,J=7.8 Hz,14.5 Hz),3.55(1H, dd,J=5.5 Hz,14.5 Hz),4.06–4.15(2H,m),4.72–4.80 (1H,m), 6.80(1H,brs),6.88–6.97(2H,m),7.10–7.42 (6H,m),7.56(1H, brs),7.78–7.88(2H,m),7.94–8.00 (1H,m)

EXAMPLE 19

Synthesis of Compound 19

Compound 19 was prepared using Boc-DLPhe(3-COOEt)-OH as a starting material in the same manner described in Example 18.

IR(KBr,cm$^{-1}$):
3322,2962,1725,1647,1542,1287,1203,750

High Resolution FAB-MS(m/e,(C$_{31}$H$_{41}$ClN$_4$O$_7$+H)$^+$): Calcd: 617.2742 Found: 617.2720

$^1$H-NMR(300 MHz,DMSO-d$_6$,δ ppm): 0.69(3H,t,J=6.6 Hz),0.79–0.88(6H,m),1.00–1.80(9H,m),1.30+1.33 (3H,t×2, J=7.0 Hz,J=7.0 Hz),2.78+2.89(1H,dd×2, J=11.7 Hz,13.5 Hz,J=9.0 Hz,13.5 Hz),3.07+3.18 (1H,dd×2,J=5.5 Hz,13.5 Hz,J=3.2 Hz,13.5 Hz),4.11–4.22 (2H,m),4.28+4.29(2H,q×2, J=7.0 Hz,J=7.0 Hz),4.56–4.68 (1H,m),6.90–6.97(1H,m), 7.16–7.24(2H,m),7.31–7.41 (2H,m),7.51+7.58(1H,d×2,J= 7.8 Hz,J=7.8 Hz),7.75+7.79 (1H,d×2,J=7.8 Hz,J=7.8 Hz), 7.86+7.94(1H,s×2),8.06–8.24 (3H,m),8.19+8.52(1H,d×2,J= 9.0 Hz,J=9.0 Hz)

EXAMPLE 20

Synthesis of Compound 20

Compound 20 was prepared using Boc-DLPhe(3-COOMe)-OH as a starting material in the same manner described in Example 18.

IR(KBr,cm$^{-1}$):
3322,2962,1728,1647,1545,1446,1290,1209,750

High Resolution FAB-MS(m/e,(C$_{30}$H$_{39}$ClN$_4$O$_7$+H)$^+$): Calcd: 603.2585 Found: 603.2598

$^1$H-NMR(300 MHz,DMSO-d$_6$,δ ppm): 0.69(3H,t,J=6.9 Hz),0.80–0.93(6H,m),1.00–1.80(9H,m),2.78+2.89 (1H,dd× 2,J=11.7 Hz,13.5 Hz,J=9.0 Hz,13.5 Hz),3.07+3.18 (1H,dd× 2,J=5.5 Hz,13.5 Hz,J=3.2 Hz,13.5 Hz),3.81+3.84 (3H,s×2), 4.10–4.22(2H,m),4.57–4.68 (1H,m),6.90–6.97(1H,m), 7.16–7.24(2H,m),7.31–7.41 (2H,m),7.51+7.58(1H,d×2,J= 7.8 Hz,J=7.8 Hz),7.75+7.79 (1H,d×2,J=7.8 Hz,J=7.8 Hz), 7.87+7.95(1H,s×2),8.08–8.26 (3H,m),8.22+8.52(1H,d×2,J= 8.8 Hz,J=8.8 Hz)

EXAMPLE 21

Synthesis of Compound 21

(1) Preparation of H-DTrp(COOMe)-DNle-O$^t$Bu.HCl

To a suspension of H-DNle-O$^t$Bu.HCl (603 mg) in dichloromethane (10 ml) were added NMM (297 μl), Boc-DTrp-OH (903 mg), HOBT.H$_2$O (413 mg) and EDCI.HCl (569 mg) successively under ice cooling. The mixture was stirred at the same temperature for 2 h and at room temperature for 1 h. The reaction mixture was diluted with ethyl acetate, washed with 10% aq. citric acid, sat. aq. NaHCO$_3$, water and brine successively, dried over MgSO$_4$ and evaporated in vacuo to give Boc-DTrp-DNle-O$^t$Bu (1.22 g). To a solution of the dipeptide derivative in dichloromethane (12 ml) were added methyl chloroformate (1 ml), pulverized NaOH (103 mg) and TBAHS (20 mg). After being stirred of the mixture at room temperature for 30 min, pulverized NaOH (103 mg) was added. This procedure was repeated twice more. The reaction mixture was diluted with dichloromethane, washed with sat. aq. NaHCO$_3$, 10% aq.citric acid, water and brine successively, dried over MgSO$_4$ and evaporated in vacuo. The residue was recrystallized from ethyl acetate and hexane to give Boc-DTrp(COOMe)-DNle-O$^t$Bu (1.15 g). The dipeptide derivative (1.03 g) was dissolved in TFA (10 ml) and the solution was stirred under ice cooling for 10 min. After evaporation of the reaction mixture, the residue was dissolved in ethyl acetate. The solution was washed with sat. aq NaHCO$_3$, water and brine successively, dried over MgSO$_4$ and concentrated under reduced pressure to give H-DTrp(COOMe)-DNle-O$^t$Bu as a free base. To a solution of the free base (750 mg) in methanol was added 3.78N - hydrogen chloride/1,4-dioxane (0.47 ml) under ice cooling. The solution was evaporated vacuo to to give H-DTrp-(COOMe)-DNle-O$^t$Bu.HCl (810 mg). FAB-MS(m/e, (C$_{23}$H$_{33}$N$_3$O$_5$+H)$^+$):432

(2) Preparation of H-Leu-DTrp(COOMe)-DNle-O$^t$Bu

To a solution of H-DTrp(COOMe)-DNle-O$^t$Bu.HCl (60 mg, prepared in (1)) in DMF (2 ml) were added Z-Leu-OH (45 mg), HOBT.H$_2$O (33 mg) and EDCI.HCl (41 mg) under ice cooling. After being stirred at the same temperature for 1 h, the mixture was diluted with ethyl acetate, washed with 10% aq. citric acid, sat. aq NaHCO$_3$ and brine successively, dried over MgSO$_4$ and evaporated in vacuo. The residue was purified by silica gel flash chromatography (Merck, Kieselgel 60) with ethyl acetate/hexane=1/2 for elution to give an oily product (72 mg), which was dissolved in methanol (3 ml). The solution was hydrogenated over 10% Pd/C at an atmospheric pressure of hydrogen for 1 h. After removal of the catalyst by filtration, the filtrate was evaporated in vacuo to give H-Leu-DTrp(COOMe)-DNle-O$^t$Bu (48 mg).

(3) Preparation of Compound 21

To a solution of H-Leu-DTrp(COOMe)-DNle-O$^t$Bu (15 mg, prepared in (2)) in chloroform (1 ml) was added 2,6-dichlorophenylisocyanate (5.6 mg) at 0°–5° C. under argon atmosphere. The mixture was stirred at the same temperature for 1.5 h, and diluted with chloroform. The solution was washed with 1N-hydrochloric acid, sat. aq. NaHCO$_3$ and brine successively, dried over MgSO$_4$ and evaporated in vacuo. The residue was purified by preparative TLC (Merck, Kieselgel 60 F$_{254}$) with chloroform/methanol=30/1 for development to give an oily product (6.7 mg), which was dissolved in TFA (1 ml). After being stirred at room temperature for 1 h, the mixture was concentrated under reduced pressure. The residue was triturated with water to give Compound 21 (4.3 mg).

m.p.: 211°–212° C.

IR(KBr,cm$^{-1}$):
3310,2962,1740,1647,1545,1461,1386,1260,1092,765

High Resolution FAB-MS(m/e,(C$_{32}$H$_{39}$C$_{12}$N$_5$O$_7$+H)$^+$): Calcd: 676.2305 Found: 676.2297

$^1$H-NMR(300 MHz,Acetone-d$_6$,δ ppm): 0.78(3H,d,J=6.1 Hz),0.79(3H,d,J=6.1 Hz),0.80(3H,t,J=8.4 Hz), 1.10–1.76(9H,m),3.08(1H,dd,J=9.6 Hz,15.1 Hz),3.37(1H, dd,J=4.7 Hz,15.1 Hz),4.00(3H,s),4.14–4.31 (2H,m), 4.77–4.91(1H,m),6.32(1H,d,J=7.1 Hz),7.23 (1H,t,J=7.8 Hz),7.28(1H,t,J=7.7 Hz),7.33(1H,t,J=7.7 Hz),7.40(2H,d,J= 7.8 Hz),7.58(1H,s),7.60(1H,s),7.66 (1H,d,J=7.6 Hz), 7.70(1H,d,J=7.3 Hz),7.70(1H,d,J=7.7 Hz),8.14(1H,d,J=7.7 Hz)

Each Compound 22–24 in the following Examples 22–24 was prepared using corresponding isocyanate in the same manner described in Example 21-(3).

EXAMPLE 22

Compound 22 m.p.: 208°–209° C.

IR(KBr,cm$^{-1}$):
3352,2962,2872,1737,1647,1551,1461,1389,1260,1095,750

High Resolution FAB-MS(m/e,(C$_{32}$H$_{40}$FN$_5$O$_7$+H)$^+$): Calcd: 626.2990 Found: 626.2984

$^1$H-NMR(300 MHz,Acetone-d$_6$,δ ppm): 0.78(3H,d,J=6.3 Hz),0.80(3H,d,J=6.3 Hz),0.86(3H,t,J=6.9 Hz), 1.20–1.50(7H,m),1.65–1.90(2H,m),3.12(1H,dd,J=9.6 Hz,15.0 Hz),3.38(1H,dd,J=4.7 Hz,15.0 Hz),4.01 (3H,s), 4.19–4.29(1H,m),4.34–4.46(1H,m),4.79–4.90 (1H,m), 6.46(1H,d,J=7.1 Hz),6.88–6.99(1H,m),7.00–7.14 (2H,m), 7.25(1H,t,J=7.8 Hz),7.32(1H,t,J=7.8 Hz),7.61 (1H,s), 7.67(1H,d,J=8.0 Hz),7.70(1H,d,J=7.8 Hz),7.81 (1H,d,J=8.2 Hz),7.91(1H,d,J=2.1 Hz),8.14(1H,d,J=7.8 Hz), 8.17–8.27(1H,m)

EXAMPLE 23

Compound 23 m.p.: 212°–224° C.

IR(KBr,cm$^{-1}$):
3322,3088,2962,2872,1740,1647,1554,1461,1389,1326, 1260,1122,762

High Resolution FAB-MS(m/e,(C$_{33}$H$_{40}$F$_3$N$_5$O$_7$+H)$^+$): Calcd: 676.2958 Found: 676.2957

$^1$H-NMR(300 MHz,DMSO-d$_6$,δ ppm): 0.64(3H,d,J=6.1 Hz),0.65(3H,d,J=6.1 Hz),0.81(3H,t,J=7.1 Hz), 0.78–1.82(9H,m),2.88(1H,dd,J=11.2 Hz,14.7 Hz), 3.10–3.25(1H,m),3.95(3H,s),4.10–4.28(2H,m),4.62–4.76 (1H,m),7.10–7.24(2H,m),7.26(1H,t,J=7.6 Hz),7.33 (1H,t,J= 7.6 Hz),7.54(1H,s),7.43–7.63(2H,m),7.76 (1H,d,J=7.6 Hz), 7.88(1H,d,J=7.9 Hz),7.88(1H,s),8.05 (1H,d,J=7.6 Hz), 8.22(1H,d,J=7.9 Hz),8.49(1H,d,J=8.4 Hz)

EXAMPLE 24

Compound 24 m.p.: 186°–188° C.

IR(KBr,cm$^{-1}$):
3346,2962,1740,1653,1506,1458,1386,1344,1260,1092,741

High Resolution FAB-MS(m/e,(C$_{32}$H$_{40}$N$_6$O$_9$+H)$^+$): Calcd: 653.2935 Found: 653.2939

$^1$H-NMR(300 MHz,Acetone-d$_6$,δ ppm): 0.79(3H,d,J=6.4 Hz),0.81(3H,d,J=6.4 Hz),0.83(3H,t,J=7.2 Hz), 1.14–1.50(7H,m),1.65–1.90(2H,m),3.11 (1H,dd,J=9.6 Hz,14.8 Hz),3.39(1H,dd,J=4.2 Hz,14.8 Hz),4.01 (3H,s), 4.17–4.29(1H,m),4.37–4.49(1H,m),4.79–4.90 (1H,m), 7.12(1H,dt,J=1.4 Hz,7.2 Hz),7.25(1H,t,J=7.6 Hz),7.31(1H, t,J=7.6 Hz),7.20–7.37(1H,m),7.55–7.67 (2H,m),7.60(1H,s), 7.69(1H,d,J=7.6 Hz),7.78(1H,d,J=9.1 Hz),8.12(1H,d,J=7.6 Hz),8.13(1H,d,J=8.2 Hz),8.54 (1H,dd,J=1.4 Hz,7.2 Hz), 9.56(1H,s)

EXAMPLE 25

Synthesis of Compound 25

A solution of Compound 24 (30 mg, obtained in Example 24) in 95% ethanol (3 ml) was hydrogenated over 10% Pd/C (20 mg) at an atmospheric pressure of hydrogen for 1.5 h. After removal of the catalyst by filtration, the filtrate was evaporated in vacuo to give Compound 25 (26 mg).

m.p.: 188°–190° C.

IR(KBr,cm$^{-1}$):
3370,2962,1740,1650,1551,1461,1386,1260,747

High Resolution FAB-MS(m/e,(C$_{32}$H$_{42}$N$_6$O$_7$+H)$^+$): Calcd: 623.3193 Found: 623.3157

$^1$H-NMR(300 MHz,DMSO-d$_6$,δ ppm): 0.64(3H,d,J=6.5 Hz),0.66(3H,d,J=6.5 Hz),0.83(3H,t,J=7.0 Hz), 0.78–1.40(7H,m),1.56–1.78(2H,m),2.88 (1H,dd,J=11.8 Hz,14.9 Hz),3.15(1H,dd,J=2.8 Hz,14.9 Hz),3.95 (3H,s), 4.09–4.21(2H,m),4.60–4.73(1H,m),6.28 (1H,d,J=8.1 Hz), 6.47(1H,dt,J=1.7 Hz,7.7 Hz),6.64 (1H,dd,J=1.7 Hz,7.7 Hz), 6.74(1H,dt,J=1.7 Hz,7.7 Hz),7.26 (1H,t,J=7.6 Hz),7.27(1H, dd,J=1.7 Hz,7.7 Hz),7.33 (1H,t,J=7.6 Hz),7.54(1H,s), 7.59(1H,s),7.76(1H,d,J=7.6 Hz),8.05(1H,d,J=7.6 Hz), 8.23(1H,d,J=7.3 Hz),8.46 (1H,d,J=8.6 Hz)

EXAMPLE 26

Synthesis of Compound 26

To a solution of Compound 25 (15 mg, obtained in Example 25) were added TEA (21 μl) and formic pivalic anhydride (15 μl) at 0°–5° C. under argon atmosphere. The mixture was stirred at the same temperature for 5 h. Water was added to the reaction mixture. The mixture was acidified with 1N-hydrochloric acid and extracted with ethyl acetate. The ethyl acetate extract was dried over anhydrous sodium sulfate and evaporated in vacuo. The residue was purified by preparative TLC (3M, Empore Silica Sheet) with chloroform/methanol/acetic acid=20/1/1 for development and the product was triturated with methanol and water to give Compound 26 (11 mg).

m.p.: 174°–178° C.

IR(KBr,cm$^{-1}$):
3310,2962,1743,1665,1554,1461,1389,1260,1092,747

High Resolution FAB-MS(m/e,($C_{33}H_{42}N_6O_8$+H)$^+$): Calcd: 651.3143 Found: 651.3134

$^1$H-NMR(300 MHz,DMSO-$d_6$,δ ppm): 0.67(3H,d,J=6.1 Hz),0.74(3H,d,J=6.1 Hz),0.70(3H,t,J=7.2 Hz), 1.00–2.00(9H,m),2.81–2.99(1H,m),3.07–3.20 (1H,m), 3.87(3H,s),4.20–4.48(2H,m),4.60–4.90(1H,m),6.87 (1H,dt, J=1.4 Hz,7.1 Hz),7.00(1H,dt,J=1.4 Hz,7.1 Hz), 7.05–7.34(2H,m),7.16(1H,t,J=7.7 Hz),7.28 (1H,t,J=7.7 Hz), 7.48(1H,s),7.45–7.59(2H,m),7.61 (1H,d,J=7.7 Hz),7.78(1H, brs),8.03(1H,d,J=7.7 Hz),8.47 (1H,brs),8.78(1H,d,J=8.3 Hz),11.77(1H,brs)

EXAMPLE 27

Synthesis of Compound 27

(1) Preparation of PhOCO-Leu-DTrp(COOMe)-DNle-O$^t$Bu

To a solution of H-Leu-DTrp(COOMe)-DNle-O$^t$Bu (320 mg, prepared in Example 21-(2)) in pyridine (2.3 ml) was added phenyl chloroformate at 0°–5° C. under argon atmosphere. The mixture was stirred at the same temperature for 1.5 h and concentrated in vacuo. The residue was dissolved in ethyl acetate and the solution was washed with 10% aq. citric acid, sat. aq. NaHCO$_3$ and brine successively, dried over MgSO$_4$ and evaporated in vacuo. The residue was purified by silica gel flash chromatography (Merck, Kieselgel 60) with ethyl acetate/hexane=2/1 for elution to give the product (337 mg).

FAB-MS(m/e, ($C_{36}H_{48}N_4O_8$+H)$^+$):665

(2) Preparation of Compound 27

A solution of PhOCO-Leu-DTrp(COOMe)-DNle-O$^t$Bu (10 mg, prepared in (1)) in TFA (1 ml) was stirred at room temperature for 1 h. The mixture was evaporated in vacuo and the residue was triturated with water to give Compound 27 (5.8 mg).

m.p.: 198°–199° C.

IR(KBr,cm$^{-1}$):
3316,2962,2872,1740,1653,1536,1461,1386,1260,1209, 1092,762

High Resolution FAB-MS(m/e,($C_{32}H_{40}N_4O_8$+H)$^+$): Calcd: 609.2924 Found: 609.2899

$^1$H-NMR(300 MHz,DMSO-$d_6$,δ ppm): 0.68(3H,d,J=6.3 Hz),0.69(3H,d,J=6.3 Hz),0.81(3H,t,J=7.1 Hz), 1.00–1.75(9H,m),2.88(1H,dd,J=11.0 Hz,14.4 Hz),3.14(1H, dd,J=5.6 Hz,14.4 Hz),3.94(3H,s),3.96–4.20 (2H,m), 4.63–4.75(1H,m),7.01(2H,dd,J=1.3 Hz,8.3 Hz),7.16(1H,dt, J=1.3 Hz,8.3 Hz),7.25(1H,t,J=7.7 Hz),7.27–7.37(3H,m), 7.52(1H,s),7.75(1H,d,J=7.7 Hz),7.83(1H,d,J=7.8 Hz), 8.05(1H,d,J=7.8 Hz),8.14 (1H,d,J=7.7 Hz),8.41(1H,d,J=8.8 Hz)

EXAMPLE 28

Synthesis of Compound 28

To a solution of PhOCO-Leu-DTrp(COOMe)-DNle-O$^t$Bu (33 mg, prepared in Example 27-(1) ) in chloroform were added hexamethyleneimine (56 µl) and TEA (100 µl) at room temperature under argon atmosphere. The mixture was stirred at 55° C. for 2 h and cooled to room temperature. The mixture was diluted with ethyl acetate, washed with 1N-hydrochloric acid, sat. aq. NaHCO$_3$ and brine successively, dried over MgSO$_4$ and evaporated in vacuo. The residue was purified by preparative TLC (Merck, Kieselgel 60 F$_{254}$) with ethyl acetate/hexane=1/1 for development to give an oily product (28 mg), which was dissolved in TFA (1 ml). After being stirred at room temperature for 1 h, the mixture was evaporated in vacuo. The residue was triturated with water to give Compound 28 (22 mg).

m.p.: 94°–97° C.

IR(KBr,cm$^{-1}$):
3352,2938,1743,1635,1536,1461,1386,1260,1221,1092, 765,747

High Resolution FAB-MS(m/e,($C_{32}H_{47}N_5O_7$+H)$^+$): Calcd: 614.3554 Found: 614.3532

$^1$H-NMR(300 MHz,CDCl$_3$,δ ppm): 0.79(3H,d,J=6.1 Hz), 0.80(3H,d,J=6.1 Hz),0.83(3H,t,J=6.8 Hz),1.10–1.93(17H, m),3.10–3.45(6H,m),3.88–3.98 (1H,m),4.02(3H,s), 4.35–4.45(1H,m),4.77–4.85(1H,m),5.21 (1H,brs),6.74(1H, d,J=8.0 Hz),7.25(1H,t,J=7.6 Hz),7.34 (1H,t,J=7.6 Hz), 7.49(1H,s),7.58(1H,d,J=7.6 Hz),7.66 (1H,d,J=8.4 Hz), 8.16(1H,d,J=7.6 Hz)

Each Compound 29–32 in the following Examples 29–32 was prepared using each corresponding amine as a starting material in the same manner described in Example 28.

EXAMPLE 29

Compound 29 m.p.: 106°–110° C.

IR(KBr,cm$^{-1}$):
3328,2962,1743,1635,1539,1461,1386,1257,1092,765,747

High Resolution FAB-MS(m/e,($C_{30}H_{43}N_5O_7$S+H)$^+$): Calcd: 618.2961 Found: 618.2987

$^1$H-NMR(300 MHz,CDCl$_3$,δ ppm): 0.80(3H,d,J=5.5 Hz), 0.81(3H,d,J=5.5 Hz),0.83(3H,t,J=7.1 Hz),1.08–1.90(9H,m), 2.49–2.64(4H,m),3.24(1H,dd,J=7.3 Hz,15.1 Hz),3.31(1H, dd,J=6.1 Hz,15.1 Hz),3.55–3.73 (4H,m),3.88–3.98(1H,m), 4.03(3H,s),4.27–4.37 (1H,m),4.70–4.80(1H,m),5.73(1H, brs),6.68(1H,d,J=8.1 Hz),7.26(1H,t,J=7.8 Hz),7.35(1H,t,J= 7.8 Hz),7.49 (1H,s),7.50(1H,d,J=6.6 Hz),7.57(1H,d,J=7.8 Hz),8.16 (1H,d,J=7.8 Hz)

EXAMPLE 30

Compound 30 m.p.: 104°–109° C.

IR(KBr,cm$^{-1}$):
3322,2962,1743,1644,1536,1461,1386,1260,1092,765,747

High Resolution FAB-MS(m/e,($C_{30}H_{43}N_5O_7$+H)$^+$): Calcd: 586.3241 Found: 586.3264

$^1$H-NMR(300 MHz,CDCl$_3$,δ ppm): 0.79(3H,d,J=6.0 Hz), 0.81(3H,d,J=6.0 Hz),0.83(3H,t,J=7.1 Hz),1.10–1.98(13H, m),3.13–3.40(6H,m),3.87–3.98 (1H,m),4.02(3H,s), 4.39–4.48(1H,m),4.78–4.85(1H,m),5.14 (1H,d,J=5.9 Hz), 6.69(1H,d,J=8.0 Hz),7.25(1H,t,J=7.4 Hz),7.34(1H,t,J=7.4 Hz),7.49(1H,s),7.59(1H,d, J=7.4 Hz),7.74(1H,d,J=7.9 Hz), 8.16(1H,d,J=7.4 Hz)

EXAMPLE 31

Compound 31 m.p.: 96°–101° C.

IR(KBr,cm$^{-1}$):
3322,2956,2866,1743,1638,1539,1461,1386,1260,1092, 765,747

High Resolution FAB-MS(m/e,($C_{31}H_{45}N_5O_7$+H)$^+$): Calcd: 600.3397, Found: 600.3385

$^1$H-NMR(300 MHz,CDCl$_3$,δ ppm): 0–77(3H,d,J=6.3 Hz),0.79(3H,d,J=6.3 Hz),0.83(3H,t, J=7.1 Hz), 1.10–1.92(15H,m),3.15–3.37(6H,m),3.86–3.98 (1H,m), 4.02(3H,s),4.31–4.40(1H,m),4.73–4.80(1H,m), 5.52(1H, brs),6.80(1H,d,J=6.4 Hz),7.25(1H,t,J=7.6 Hz), 7.34(1H,t,J= 7.6 Hz),7.50(1H,s)7.58(1H,d,J=7.6 Hz), 7.62(1H,d,J=7.2 Hz),8.16(1H,d,J=7.6 Hz)

EXAMPLE 32

Compound 32 m.p.: 104°–108° C.

IR(KBr,cm$^{-1}$):
3328,2962,1743,1647,1539,1461,1386,1260,1092,765, 747

High Resolution FAB-MS(m/e,($C_{29}H_{41}N_5O_7S$+H)$^+$): Calcd: 604.2805, Found: 604.2799

$^1$H-NMR(300 MHz,CDCl$_3$,δ ppm): 0.75–0.86(9H,m), 1.05–1.92(9H,m),2.90–3.00(2H,m), 3.28(2H,d,J=7.4 Hz), 3.39–3.48(1H,m),3.62–3.70(1H,m), 3.85–3.95(1H,m), 4.03(3H,s),4.17(1H,d,J=9.1 Hz),4.43 (1H,d,J=9.1 Hz), 4.48–4.56(1H,m),4.73–4.82(1H,m),5.93 (1H,brs),6.57(1H, d,J=8.5 Hz),7.26(1H,t,J=7.8 Hz),7.35 (1H,t,J=7.8 Hz), 7.49(1H,s),7.58(1H,d,J=7.8 Hz),7.59 (1H,d,J=11.9 Hz), 8.16(1H,d,J=7.8 Hz)

EXAMPLE 33

Synthesis of Compound 33

(1) Preparation of PhOCO-Leu-OBzl

To a solution of H-Leu-OBzl·TsOH (1.01 g) in pyridine (9 ml) was added phenyl chloroformate (386 μl) at 0°–5° C. under argon atmosphere. The mixture was stirred at the same temperature for 2 h and concentrated in vacuo. The residue was dissolved in ethyl acetate and the solution was washed with 1N-hydrochloric acid, water and brine successively, dried over MgSO$_4$ and evaporated in vacuo. The residue was purified by silica gel chromatography (Merck, Kieselgel 60) with ethyl acetate/hexane=1/10 for elution to give the product (828 mg).

FAB-MS(m/e, ($C_{20}H_{23}NO_4$+H)$^+$):342

(2) Preparation of $^i$Pr$_2$NCO-Leu-OBzl

To a solution of PhOCO-Leu-OBzl (70 mg, prepared in (1)) in chloroform (2 ml) were added diisopropylamine (575 μl) and TEA (286 μl) at room temperature under argon atmosphere. The mixture was stirred at 55° C. for 17 h and cooled to room temperature. The mixture was diluted with ethyl acetate, washed with N-hydrochloric acid, sat. aq. NaHCO$_3$ and brine successively, dried over MgSO$_4$ and evaporated in vacuo.

The residue was purified by preparative TLC (Merck, Kieselgel 60 F$_{254}$) with ethyl acetate/hexane=1/4 for development to give the product (32 mg).

FAB-MS(m/e, ($C_{20}H_{32}N_2O_3$+H)$^+$):349

(3) Preparation of Compound 33

A mixture of $^i$Pr$_2$NCO-Leu-OBzl (32 mg, obtained in (2)) and 10% Pd/C (10 mg) in methanol (1 ml) was stirred at room temperature under an atmospheric pressure of hydrogen for 16 h. The catalyst was filtered off and the filtrate was concentrated under reduced pressure. The residue was dissolved in dichloromethane (1.5 ml). To the solution were added H-DTrp(COOMe)-DNle-O$^t$Bu·HCl (40 mg, prepared in Example 21-(1)), NMM (10 μl), HOBT·H$_2$O (13 mg) and EDCI·HCl (18 mg) under ice cooling.

After being stirred at room temperature for 1.5 h, the mixture was diluted with ethyl acetate, washed with sat. aq. NaHCO$_3$, 10% aq. citric acid, water and brine successively, dried over MgSO$_4$ and evaporated in vacuo. The residue was purified by preparative TLC (Merck, Kieselgel 60 F$_{254}$) with ethyl acetate/hexane=1/1 for development to give the product (52 mg), which was dissolved in TFA (1 ml). After being stirred at room temperature for 1 h, the mixture was evaporated in vacuo. The residue was triturated with water to give Compound 33 (18 mg).

m.p.: 94°–96° C.

IR(KBr,cm$^{-1}$):
3322,2962,2872,1743,1650,1524,1461,1386,1341,1311, 1260,1221,1149,1092,765,747

High Resolution FAB-MS(m/e,($C_{32}H_{49}O_7N_5$+H)$^+$): Calcd: 616,3718, Found: 616,3699

$^1$H-NMR(300 MHz,DMSO-d$_6$,δ ppm): 0.66(3H,d,J=6.0 Hz),0.67(3H,d,J=6.0 Hz),0.85(3H,t, J=7.0 Hz),1.08+ 1.10(12H,d×2,J=6.8 Hz),1.10–1.40 (7H,m),1.15–1.30(2H, m),2.86(1H,dd,J=11.0 Hz,14.8 Hz), 3.18(1H,dd,J=3.5 Hz,14.8 Hz),3.70(2H,sept,J=6.8 Hz), 3.95(3H,s), 3.95–4.07(1H,m),4.10–4.20(1H,m),4.60–4.70 (1H,m), 5.56(1H,d,J=7.3 Hz),7.25(1H,t,J=7.6 Hz), 7.32(1H,t,J=7.6 Hz),7.49(1H,s),7.70(1H,d,J=7.6 Hz), 8.04(1H,d,J=7.6 Hz), 8.15(1H,d,J=8.1 Hz),8.18(1H,d, J=9.3 Hz)

Each Compound 34 and 35 in the following Examples 34 and 35 was prepared using corresponding amine in the same manner described in Example 33-(2) and (3).

EXAMPLE 34

Compound 34 m.p.: 85°–94° C.

IR(KBr,cm$^{-1}$):
3328,2962,2872,1743,1638,1533,1461,1383,1344,1311, 1260,1224,1200,1092,765,747

High Resolution FAB-MS(m/e,($C_{32}H_{47}N_5O_7$+H)$^+$): Calcd: 614.3554, Found: 614.3569

$^1$H-NMR(300 MHz,DMSO-d$_6$,δ ppm): 0.66(3H,d,J=6.0 Hz),0.68(3H,d,J=6.0 Hz),0.86(3H,t, J=7.0 Hz),1.06(3H,d,J= 6.1 Hz),1.09(3H,d,J=6.1 Hz), 1.10–1.40(7H,m), 1.40–1.60(2H,m),1.65–1.78(2H,m), 1.80–1.94(2H,m), 2.86(1H,dd,J=4.0 Hz,10.7 Hz),3.12–3.30 (1H,m),3.78(2H, sext,6.1 Hz),3.96(3H,s),4.08–4.20 (2H,m),4.50–4.68(1H, m),5.65(1H,d,J=6.8 Hz), 7.27(1H,t,J=7.4 Hz),7.32(1H,t,J= 7.4 Hz),7.49(1H,s), 7.68(1H,d,J=7.4 Hz),8.05(1H,d,J=7.4 Hz),8.20–8.31 (2H,m)

EXAMPLE 35

Compound 35 m.p.: 100°–110° C.

IR(KBr,cm$^{-1}$):
3376,2962,2866,1743,1632,1539,1461,1386,1341,1311, 1260,1188,1152,747

High Resolution FAB-MS(m/e,$(C_{32}H_{47}N_5O_7+H)^+$): Calcd: 614,3554, Found: 614,3540

$^1$H-NMR(300MHz,DMSO-d$_6$,δ ppm): 0.62–0.75(6H,m), 0.86(3H,t,J=7.0 Hz),0.95+0.97 (3H,d×2,J=6.8 Hz), 1.03–1.58(13H,m),1.65–1.78(2H,m), 2.77–2.91(1H,m), 3.15–3.50(2H,m),3.63–3.77(1H,m), 3.86–4.00(1H,m), 4.01(3H,s),4.04–4.30(2H,m),4.53–4.64 (1H,m), 6.15–6.25(1H,m),7.25(1H,t,J=7.3 Hz), 7.32(1H,t,J=7.3 Hz), 7.47+7.48(1H,s×2),7.66+7.67 (1H,d×2,J=7.3 Hz),8.05(1H, d,J=7.3 Hz),8.15–8.28 (2H,m)

EXAMPLE 36

Synthesis of Compound 36

(1) Preparation of (c-Pent)nPrNCO-Leu-OBzl

To a mixture of H-Leu-OBzl·TsOH (1.0 g) and CDI (469 mg) in chloroform (10 ml) was added TEA (0.43 ml) at room temperature and the mixture was stirred at the same temperature for 1 h. Cyclopentylpropylamine (0.47 ml) was added and the reaction mixture was stirred at room temperature for 6 h. The mixture was diluted with ethyl acetate, washed with 1N-hydrochloric acid and brine, dried over MgSO$_4$ and evaporated in vacuo. The residue was purified by silica gel chromatography (Merck, Kieselgel 60) with ethyl acetate/hexane=3/7 for elution to give the product (850 mg).

FAB-MS(m/e, $(C_{22}H_{34}NO_3+H)^+$):375

(2) Preparation of Compound 36

Compound 36 was prepared using (c-Pent)nPrNCO-Leu-OBzl (prepared in (1)) as a starting material in the same manner described in Example 33-(3).

m.p.: 68°–73° C.

IR(KBr,cm$^{-1}$): 3382,2962,2872,1743,1632,1533,1461,1386,1344,1311, 1260,1227,1092,765,747

High Resolution FAB-MS(m/e,$(C_{34}H_{51}N_5O_7+H)^+$):642

$^1$H-NMR(300 MHz,CDCl$_3$,δ ppm): 0.81(3H,d,J=5.8 Hz), 0.82(3H,d,J=6.7 Hz),0.83(3H,t, J=6.7 Hz),0.87(3H,t,J=7.3 Hz),1.12–1.95(19H,m), 2.91(1H,dt,J=7.9 Hz,15.8 Hz), 3.00(1H,dt,J=7.9 Hz, 15.8 Hz),3.27(1H,dd,J=4.5 Hz,15.0 Hz),3.33(1H,dd, J=6.0 Hz,15.0 Hz),3.84–3.98(1H,m), 4.02(3H,s), 4.14(1H,quint,J=7.9 Hz),4.34(1H,ddd,J=4.6 Hz,6.4 Hz, 8.2 Hz),4.75(1H,d,J=6.4 Hz),4.78–4.86(1H,m), 6.60 (1H,d,J=7.9 Hz),7.26(1H,t,J=7.6 Hz),7.35(1H,t, J=7.6 Hz),7.48(1H,s),7.59(1H,d,J=7.6 Hz),7.61 (1H,d,J=8.2 Hz), 8.16(1H,d,J=7.6 Hz)

Each Compound 37–39 in the following Examples 37–39 was prepared using each corresponding amine as a starting material in the same manner described Example 36.

EXAMPLE 37

Compound 37 m.p.: 98°–107° C.

IR(KBr,cm$^{-1}$): 3388,2914,2860,1743,1653,1551,1461,1386,1260,1092, 765,747

High Resolution FAB-MS(m/e,$(C_{35}H_{45}N_5O_7+H)^+$): Calcd: 648.3398, Found: 648.3346

$^1$H-NMR(300 MHz,DMSO-d$_6$,δ ppm): 0.65(3H,d,J=5.6 Hz),0.69(3H,d,J=5.6 Hz),0.86(3H,t, J=7.0 Hz), 1.07–1.45(7H,m),1.65–1.83(2H,m),2.60–2.80 (2H,m), 2.86(1H,dd,J=11.0 Hz,14.4 Hz,3.15–3.30(1H,m), 3.30–3.60(2H,m),3.94(3H,s),3.94–4.05(1H,m),4.06–4.20 (1H,m),4.39(1H,d,J=16.4 Hz),4.50(1H,d,J=16.4 Hz), 4.52–4.66(1H,m),6.44(1H,d,J=7.1 Hz),7.00–7.19(4H,m), 7.23(1H,t,J=7.5 Hz),7.31(1H,t,J=7.5 Hz),7.49(1H,s), 7.68(1H,d,J=7.5 Hz),8.04(1H,d,J=7.5 Hz),8.19(1H,d, J=7.6 Hz),8.30(1H,d,J=8.7 Hz)

EXAMPLE 38

Compound 38 m.p.: 79°–82° C.

IR(KBr,cm$^{-1}$): 3316,2692,2872,1743,1629,1533,1461,1386,1341,1311, 1260,1227,1092,765,747

High Resolution FAB-MS(m/e,$(C_{35}H_{53}N_5O_7+H)^+$): Calcd: 656.4024, Found: 656.4029

$^1$H-NMR(300 MHz,CDCl$_3$, δ ppm): 0.81(3H,d,J=6.3 Hz), 0.82(3H,d,J=6.3 Hz),0.83(3H,t, J=6.3 Hz),0.91(3H,t,J=7.4 Hz),1.10–1.95(21H,m),2.93 (1H,dt,J=7.5 Hz,15.0 Hz), 3.00(1H,dt,J=7.5 Hz,15.0 Hz), 3.27(1H,dd,J=6.6 Hz,15.0Mz),3.31(1H,dd,J=6.0 Hz, 15.0 Hz),3.91(1H,q,J= 6.7 Hz),4.02(3H,s),4.14(1H, quint,J=8.2 Hz),4.34(1H,ddd, J=5.4 Hz,6.4 Hz,8.7 Hz), 4.72(1H,d,J=6.4 Hz),4.82(1H,ddd, J=6.0 Hz,6.6 Hz, 7.6 Hz),6.56(1H,d,J=7.6 Hz),7.26(1H,t,J= 7.6 Hz), 7.35(1H,t,J=7.6 Hz),7.48(1H,s),7.59(1H,d,J=6.7 Hz), 7.64(1H,d,J=7.6 Hz),8.16(1H,d,J=7.6 Hz)

EXAMPLE 39

Compound 39 m.p.: 95°–110° C.

IR(KBr,cm$^{-1}$): 3334,2962,2872,1743,1662,1536,1461,1386,1344,1311, 1260,1149,1128,1092,765,747

High Resolution FAB-MS(m/e,$(C_{33}H_{49}N_5O_7+H)^+$): Calcd: 628.3718, Found: 628.3699

$^1$H-NMR(300 MHz,DMSO-d$_6$,δ ppm): 0.66(3H,d,J=6.0 Hz),0.70(3H,d,J=6.0 Hz),0.86(3H,t, J=7.1 Hz),1.01(3H,d,J= 7.2 Hz),1.04(3H,d,J=7.2 Hz), 1.05–1.55(11H,m), 1.60–1.80(4H,m),2.84(1H,dd, J=11.5 Hz,15.0 Hz), 3.15–3.25(1H,m),3.95(3H,s),4.01–4.18 (4H,m), 4.54–4.65(1H,m),6.04(1H,d,J=6.9 Hz),7.25 (1H,t,J=7.5 Hz),7.32(1H,t,J=7.5 Hz),7.48(1H,s),7.67 (1H,d,J=7.5 Hz), 8.05(1H,d,J=7.5 Hz),8.20(1H,d, J=7.6 Hz),8.24(1H,d,J=8.8 Hz)

Each Compound 40–43 in the following Examples 40–43 was prepared using each corresponding amino acid benzyl ester tosylate as a starting material in the same manner described in Example 39.

EXAMPLE 40

Compound 40 m.p.: 103°–107° C.

IR(KBr,cm$^{-1}$): 3376,2956,2872,1743,1656,1530,1461,1386,1341,1260, 1227,1137,1092,765,747

FAB-MS(m/e,$(C_{34}H_{51}N_5O_7+H)^+$):642

$^1$H-NMR(300 MHz,CDCl$_3$,δ ppm): 0.82(3H,t,J=7.3 Hz), 0.85(9H,s),1.14(6H,d,J=7.1 Hz), 1.20–1.90(14H,m), 3.26(1H,dd,J=5.5 Hz,14.6 Hz),3.35 (1H,dd,J=6.3 Hz,14.6 Hz),3.85–3.95(2H,m),4.02(3H,s), 4.09–4.21(1H,m), 4.28(1H,ddd,J=5.3 Hz,6.2 Hz,8.3 Hz), 4.76(1H,ddd,J=5.5

Hz,6.3 Hz,8.3 Hz),4.93(1H,d, J=6.2 Hz),6.48(1H,d,J=8.3 Hz),7.27(1H,t,J=7.6 Hz), 7.35(1H,t,J=7.6 Hz),7.48(1H,s), 7.58(1H,d,J=7.6 Hz), 7.72(1H,d,J=7.3 Hz),8.16(1H,d,J=7.6 Hz)

EXAMPLE 41

Compound 41 m.p.: 101°–104.5° C.

IR(KBr,cm$^{-1}$):
3286,2944,2872,1743,1653,1560,1530,1461,1386,1341, 1311,1260,1143,1092,756

High Resolution FAB-MS(m/e,$(C_{36}H_{47}N_5O_7+H)^+$): Calcd: 662.3554, Found: 662.3530

$^1$H-NMR(300 MHz,CDCl$_3$,δ ppm): 0.70–1.92(12H,m), 0.77(3H,t,J=7.4 Hz),1.01(3H,d, J=7.1 Hz),1.04(3H,d,J=7.1 Hz),2.90(1H,dd,J=5.1 Hz, 14.5 Hz),2.94(1H,dd,6.5 Hz,12.6 Hz),3.06(1H,dd, J=8.1 Hz,12.6 Hz),3.32(1H,dd,J=5.1 Hz,14.5 Hz),3.74–3.93 (1H,m),3.93–4.12(2H,m),4.03(3H, s),4.27(1H,ddd, J=4.6 Hz,6.5 Hz,8.1 Hz),4.69(1H,dt,J=5.1 Hz,7.6 Hz), 5.05(1H,brs),6.32(1H,d,J=6.7 Hz), 7.06–7.45(9H,m), 7.60(1H,brs),8.14(1H,d,J=7.9 Hz)

EXAMPLE 42

Compound 42 m.p.: 102°–110° C.

IR(KBr,cm$^{-1}$):
3406,2932,2860,1743,1665,1536,1461,1386,1341,1260, 1203,1149,1128,1092,765,747

High Resolution FAB-MS(m/e,$(C_{36}H_{53}N_5O_7+H)^+$): Calcd: 668.4024, Found: 668.4004

$^1$H-NMR(300 MHz,CDCl$_3$,δ ppm): 0.70–1.92(25H,m), 0.81(3H,t,J=7.1 Hz),1.14(3H,d, J=7.0 Hz),1.15(3H,d,J=7.0 Hz),3.23(1H,dd,J=5.3 Hz, 15.1 Hz),3.36(1H,dd,J=7.0 Hz,15.1 Hz),3.85–4.20(3H,m), 4.02(3H,s),4.22–4.38(1H, m),4.73–4.90(1H,m),5.02 (1H,brs),6.63(1H,d,J=6.2 Hz), 7.26(1H,t,J=7.3 Hz), 7.35(1H,t,J=7.3 Hz),7.49(1H,s), 7.59(1H,d,J=7.3 Hz), 7.65(1H,d,J=7.0 Hz),8.16(1H,d,J=7.3 Hz)

EXAMPLE 43

Compound 43 m.p.: 96°–104° C.

IR(KBr,cm$^{-1}$):
3328,2962,2872,1743,1656,1530,1461,1386,1341,1311, 1260,1227,1092,765,747

High Resolution FAB-MS(m/e,$(C_{32}H_{47}N_5O_7+H)^+$): Calcd: 614.3554, Found: 614.3558

$^1$H-NMR(300 MHz,CDCl$_3$,δ ppm): 0.79(3H,d,J=6.7 Hz), 0.82(3H,t,J=7.0 Hz),0.90(3H,d, J=6.7 Hz),1.00–1.40(6H, m),1.17(3H,d,J=7.0 Hz),1.18 (3H,d,J=7.0 Hz), 1.42–2.10(7H,m),3.26(1H,dd,J=6.0 Hz, 14.3 Hz),3.31(1H, dd,J=6.0 Hz,14.3 Hz),3.73(1H,dd, J=7.2 Hz,7.5 Hz), 3.94–4.05(1H,m),4.01(3H,s),4.06–4.22 (1H,m),4.34(1H,dt, J=5.8Hz,8.0 Hz),4.86(1H,dt, J=6.0 Hz,7.8 Hz),5.09(1H,d,J= 7.2 Hz),6.74(1H,d, J=7.8 Hz),7.26(1H,t,J=7.3 Hz),7.34(1H, t,J=7.3 Hz), 7.49(1H,s),7.50(1H,d,J=5.8 Hz),7.61(1H,d,J= 7.3 Hz), 8.15(1H,d,J=7.3 Hz)

EXAMPLE 44

Synthesis of Compound 44

Compound 44 was prepared using 1-adamantanamine instead of diisopropylamine in the same manner described in Example 33-(2).

m.p.: 129°–137° C.

IR(KBr,cm$^{-1}$):
3316,2962,2872,1743,1635,1539,1461,1386,1260,1092, 747

High Resolution FAB-MS(m/e,$(C_{36}H_{51}N_5O_7+H)^+$): Calcd: 666.3867, Found: 666.3879

$^1$H-NMR(300 MHz,DMSO-d$_6$,δ ppm): 0.61(3H,d,J=3.9 Hz),0.63(3H,d,J=4.4 Hz),0.87(3H,t, J=6.8 Hz), 0.90–2.00(24H,m),2.85(1H,dd,J=11.2 Hz, 14.4 Hz), 3.11–3.25(1H,m),3.83–3.95(1H,m),3.96(3H,s), 4.10–4.20(1H,m),4.56–4.67(1H,m),5.63(1H,s),5.75 (1H,d, J=7.0 Hz),7.25(1H,t,J=7.5 Hz),7.32(1H,t, J=7.5 Hz), 7.49(1H,s),7.70(1H,d,J=7.5 Hz),8.04 (1H,d,J=7.5 Hz), 8.18(1H,d,J=7.8 Hz),8.31(1H,d, J=8.7 Hz)

EXAMPLE 45

Synthesis of Compound 45

Compound 45 was prepared using D-1-aminobutyric acid benzyl ester as a starting material in the same manner described in Example 1-(2) and (3).

m.p.: 216°–218° C.

IR(KBr,cm$^{-1}$):
3448,2968,1743,1647,1599,1536,1461,1389,1341,1314, 1260,1170,1095,1050,765,747

High Resolution FAB-MS(m/e,$(C_{28}H_{40}N_4O_8+H)^+$): Calcd: 561.2925, Found: 561.2911

$^1$H-NMR(300 MHz,CD$_3$OD,δ ppm): 0.77(3H,d,J=6.4 Hz),0.78(3H,d,J=6.4 Hz),0.87(3H,t, J=7.4 Hz), 1.23–1.35(2H,m),1.37(9H,s),1.68–1.93 (3H,m),3.07(1H,dd, J=5.1 Hz,10.7 Hz),3.14–3.17(1H,m), 3.95–4.02(1H,m), 4.00(3H,s),4.18(1H,dd,J=5.1 Hz, 6.5 Hz),4.65–4.75(1H,m), 7.24(1H,t,J=7.7 Hz),7.29 (1H,t,J=7.7 Hz),7.51(1H,s), 7.68(1H,d,J=7.7 Hz), 8.10(1H,d,J=7.7 Hz)

EXAMPLE 46

Synthesis of Compound 46

Compound 46 was prepared using t-butylisocyanate in the same manner described in Example 21-(3).

m.p.: 116°–121° C.

IR(KBr,cm$^{-1}$):
3400,2962,1743,1650,1557,1461,1389,1260,1092,765, 747

High Resolution FAB-MS(m/e,$(C_{30}H_{45}N_5O_7+H)^+$): Calcd: 588.3397, Found: 588.3369

$^1$H-NMR(300 MHz,DMSO-d$_6$,δ ppm): 0.61(6H,d,J=5.1 Hz),0.87(3H,t,J=7.0 Hz),1.15(9H,s), 0.82–1.89(9H,m), 2.86(1H,dd,J=11.3 Hz,14.4 Hz),3.11–3.21 (1H,m),3.96(3H, s),4.09–4.21(2H,m),4.58–4.70 (1H,m),5.73(1H,d,J=9.8 Hz), 5.73(1H,s),7.25(1H,t, J=7.5 Hz),7.32(1H,t,J=7.5 Hz), 7.50(1H,s),7.72(1H,d, J=7.5 Hz),8.04(1H,d,J=7.8 Hz), 8.21(1H,d,J=7.5 Hz),8.31(1H,d,J=8.8 Hz)

EXAMPLE 47

Synthesis of Compound 47

Compound 47 was prepared using 2-aminopyridine instead of hexamethyleneimine in the same manner described in Example 28.

m.p.: 109°–111° C.

IR(KBr,cm$^{-1}$):
3364,3076,2968,2872,1716,1656,1575,1461,1389,1260, 1203,1092,765,723

High Resolution FAB-MS(m/e,($C_{31}H_{40}N_6O_7$+H)$^+$): Calcd: 609.3036, Found: 609.3030

$^1$H-NMR(300 MHz,DMSO-d$_6$,δ ppm): 0.64(3H,d,J=6.1 Hz),0.67(3H,d,J=6.1 Hz),0.82(3H,t, J=7.2 Hz), 1.05–1.38(7H,m),1.56–1.80(2H,m),2.89 (1H,dd,J=11.2 Hz,14.6 Hz),3.13(1H,dd,J=1.3 Hz,14.6 Hz), 3.96(3H,s), 4.13–4.32(2H,m),4.63–4.76(1H,m),6.95 (1H,dd,J=5.5 Hz,7.0 Hz),7.26(1H,t,J=7.7 Hz),7.33 (1H,t,J=7–7 Hz), 7.38(1H,d,J=8.7 Hz),7.54(1H,s),7.65–7.75 (1H,m),7.78(1H, d,J=7.7 Hz),7.86–8.02(1H,m),8.05 (1H,d,J=7.8 Hz), 8.14(1H,dd,J=1.3 Hz,5.5 Hz),8.27 (1H,d,J=7.7 Hz),8.50(1H, d,J=8.8 Hz),9.34(1H,brs)

EXAMPLE 48

Synthesis of Compounds 48 and 49

Compound 48 (ester form) and Compound 49 (deprotected form) were prepared using heptamethyleneimine instead of hexamethyleneimine in the same manner described in Example 28.

Compound 48

(colorless amorphous)

IR(KBr,cm$^{-1}$):
3304,2932,2866,1743,1632,1533,1461,1386,1257,1152, 1092,765,747

High Resolution FAB-MS(m/e,($C_{37}H_{57}N_5O_7$+H)$^+$): Calcd: 684.4337, Found: 684.4336

$^1$H-NMR(300 MHz,CDCl$_3$, δ ppm): 0.82(3H,t,J=7.1 Hz), 0.84(3H,d,J=6.3 Hz),0.85(3H,d, J=6.3 Hz),1.06–1.80(19H, m),1.41(9H,s),3.19(1H,dd, J=5.9 Hz,14.7 Hz),3.33(1H,dd, J=6.1 Hz,14.7 Hz),3.13–3.50 (4H,m),4.01(3H,s), 3.96–4.10(1H,m),4.27–4.37 (1H,m),4.59(1H,d,J=6.8 Hz), 4.80–4.90(1H,m),6.53 (1H,d,J=8.8 Hz),6.99(1H,d,J=7.7 Hz),7.25(1H,t, J=7.3 Hz),7.33(1H,t,J=7.3 Hz),7.47(1H,s), 7.62 (1H,d,J=7.3 Hz),8.17(1H,d,J=7.3 Hz)

Compound 49 m.p.: 99°–104° C.

IR(KBr,cm$^{-1}$):
3316,2932,2872,1743,1632,1533,1461,1386,1260,1092, 765,747

High Resolution FAB-MS(m/e,($C_{33}H_{49}N_5O_7$+H)$^+$): Calcd: 628.3710, Found: 628.3693

$^1$H-NMR(300 MHz,CDCl$_3$, δ ppm): 0.80(3H,d,J=5.9 Hz), 0.81(3H,d,J=5.9 Hz),0.83(3H,t, J=6.0 Hz),1.09–1.95(19H, m),3.05–3.46(6H,m),3.88–3.98 (1H,m),4.02(3H,s), 4.31–4.41(1H,m),4.77–4.86(1H,m), 4.98(1H,d,J=7.0 Hz), 6.63(1H,d,J=7.4 Hz),7.25(1H,t, J=7.5 Hz),7.34(1H,t,J=7.5 Hz),7.48(1H,s),7.58(1H,d, J=7.5 Hz),7.68(1H,d,J=7.8 Hz), 8.16(1H,d,J=7.5 Hz)

EXAMPLE 49

Synthesis of Compound 50

Compound 50 was prepared using H-DNva-O$^t$Bu as a starting material in the same manner described in Example 39.

m.p.: 112°–116° C.

IR(KBr,cm$^{-1}$):
3382,2962,2872,1743,1656,1620,1530,1461,1386,1260

High Resolution FAB-MS(m/e,($C_{32}H_{47}N_5O_7$+H)$^+$): Calcd: 614.3554, Found: 614.3539

$^1$H-NMR(300 MHz,CDCl$_3$,δ ppm): 0.81(6H,d,J=5.4 Hz), 0.84(3H,t,J=7.3 Hz),1.14(3H,d, J=6.5 Hz),1.15(3H,d,J=6.6 Hz),1.01–1.89(13H,m),3.29 (2H,d,J=5.7 Hz),3.92–4.02(2H, m),4.01(3H,s),4.09–4.16 (1H,m),4.28–4.35(1H,m),4.83(1H, dt,J=6.3 Hz,5.7 Hz), 4.96(1H,d,J=4.8 Hz),6.67–6.72(1H, brs),7.25(1H,t, J=7.8 Hz),7.34(1H,t,J=7.8 Hz),7.48(1H,s), 7.58(1H,d, J=7.8 Hz),7.65(1H,d,J=6.3 Hz),8.16(1H,d,J=7.8 Hz)

EXAMPLE 50

Synthesis of Compound 51

Compound 51 was prepared using H-DNva-O$^t$Bu as a starting material in the same manner described in Example 40.

m.p.: 115°–119° C.

IR(KBr,cm$^{-1}$):
3358,2962,2872,1746,1659,1620,1533,1461,1386,1260

High Resolution FAB-MS(m/e,($C_{33}H_{49}N_5O_7$+H)$^+$): Calcd: 628.3732, Found: 628.3683

$^1$H-NMR(300 MHz,CDCl$_3$,δ ppm): 0.84(9H,s),0.84(3H, t,J=7.2 Hz),1.14(6H,d,J=7.1 Hz), 1.01–1.89(12H,m), 3.28(1H,dd,J=5.1 Hz,14.1 Hz),3.32 (1H,dd,J=6.0 Hz,14.1 Hz),3.87–4.01(2H,m),4.01(3H,s), 4.10–4.20(1H,m), 4.32(1H,dt,J=8.1 Hz,4.5 Hz),4.76 (1H,ddd,J=5.1 Hz,6.9 Hz,8.1 Hz),4.98(1H,d,J=5.4 Hz), 6.57–6.60(1H,brs), 7.24(1H,t,J=7.8 Hz),7.34(1H,t, J=7.8 Hz),7.48(1H,s), 7.58(1H,d,J=7.8 Hz),7.69(1H,d, J=8.1 Hz),8.16(1H,d,J=7.8 Hz)

EXAMPLE 51

Synthesis of Compound 52

Compound 52 was prepared using H-Ile-OBzl·TsOH as a starting material in the same manner described in Example 39.

m.p.: 85°–95° C.

IR(KBr,cm$^{-1}$):
3328,2968,2872,1743,1671,1539,1461,1386,1344,1311, 1260,1203,1149,1092,765,747

High Resolution FAB-MS(m/e,($C_{33}H_{49}N_5O_7$+H)$^+$): Calcd: 628.3710, Found: 628.3689

$^1$H-NMR(300 MHz,DMSO-d$_6$, δ ppm): 0.42(3H,d,J=6.8 Hz),0.64(3H,t,J=7.3 Hz),0.81–0.98 (1H,m),0.86(3H,t,J=7.1 Hz),1.04(3H,d,J=4.8 Hz), 1.06(3H,d,J=4.8 Hz), 1.20–1.80(14H,m),2.84(1H,dd, J=11.4 Hz,14.9 Hz), 3.24(1H,dd,J=2.6 Hz,14.9 Hz), 3.78(1H,t,J=7.8 Hz), 3.96(3H,s),4.07–4.20(3H,m), 4.58–4.68(1H,m),5.94(1H,d, J=7.8 Hz),7.25(1H,t, J=7.6 Hz),7.32(1H,t,J=7.6 Hz), 7.52(1H,s),7.66(1H,d, J=7.6 Hz),8.04(1H,d,J=7.6 Hz), 8.27(1H,d,J=7.8 Hz), 8.31(1H,d,J=8.7 Hz)

Each Compound 53 and 54 in the following Example 52 and 53 was prepared using each corresponding amino acid benzyl ester tosylate as a starting material in the same manner described in Example 51.

EXAMPLE 52

Compound 53 m.p.: 85°–94° C.

IR(KBr,cm$^{-1}$):
3328,2968,2872,1743,1671,1530,1461,1386,1344,1311, 1260,1200,1149,1092,765,747

High Resolution FAB-MS(m/e,($C_{33}H_{49}N_5O_7$+H)$^+$): Calcd: 628.3710, Found: 628.3698

$^1$H-NMR(300 MHz,DMSO-d$_6$,δ ppm): 0.51(3H,d,J=6.5 Hz),0.60(3H,t,J=7.1 Hz),0.80–0.92 (1H,m),0.86(3H,t,J=7.0 Hz),1.04(3H,d,J=6.2 Hz), 1.06(3H,d,J=6.2 Hz), 1.20–1.80(14H,m),2.83(1H,dd, J=11.7 Hz,14.7 Hz), 3.23(1H,dd,J=2.8 Hz,14.7 Hz), 3.88(1H,t,J=7.7 Hz), 3.96(3H,s),4.02–4.18(3H,m), 4.59–4.69(1H,m),5.78(1H,d, J=7.7 Hz),7.25(1H,t, J=7.6 Hz),7.32(1H,t,J=7.6 Hz), 7.53(1H,s),7.69(1H,d, J=7.6 Hz),8.04(1H,d,J=7.6 Hz), 8.27(1H,d,J=7.52 Hz), 8.32(1H,d,J=9.1 Hz)

EXAMPLE 53

Compound 54 m.p.: 108°–111° C.

IR(KBr,cm$^{-1}$):
3340,2962,2872,1743,1650,1632,1518,1461,1386,1260, 1146,1092,765,747

High Resolution FAB-MS(m/e,($C_{33}H_{49}N_5O_7$+H)$^+$): Calcd: 628.3711, Found: 628.3705

$^1$H-NMR(400 MHz,CDCl$_3$, δ ppm): 0.81(3H,t,J=6.8 Hz), 0.91(9H,s),1.19(6H,d,J=6.8 Hz), 1.12–1.36(4H,m), 1.43–1.87(8H,m),3.25(1H,dd,J=5.9 Hz, 15.6 Hz),3.34(1H, dd,J=6.8 Hz,15.6 Hz),3.87–4.00(1H,m), 4.01(3H,s), 4.01–4.06(1H,m),4.13–4.18(1H,m),4.35–4.40 (1H,m), 4.81–4.87(1H,m),5.12(1H,d,J=7.8 Hz),6.76–6.82 (1H,brs), 7.27(1H,t,J=7.8 Hz),7.35(1H,t,J=7.8 Hz), 7.39–7.42(1H, brs),7.50(1H,s),7.63(1H,d,J=7.8 Hz), 8.17(1H,d,J=7.8 Hz)

EXAMPLE 54

Synthesis of Compound 55

Compound 55 was prepared using 2-(2-chlorophenyl)carbamoyloxy- 4-methylpentanoic acid, which was prepared using 2-hydroxy-5-methylpentanoic acid instead of H-Leu-OBzl in the same manner described in Example 18-(2), as a starting material in the same manner described in Example 33-(3).

m.p.: 161°–163° C.

IR(KBr,cm$^{-1}$):
3310,2962,1740,1659,1533,1461,1449,1386,1260,1212, 1089,747

High Resolution FAB-MS(m/e,($C_{32}H_{39}ClN_4O_8$+H)$^+$): Calcd: 643.2535, Found: 643.2511

$^1$H-NMR(300 MHz,CDCl$_3$,δ ppm): 0.82(3H,t,J=7.0 Hz), 0.91(6H,d,J=4.5 Hz),1.13–1.31 (4H,m),1.56–1.84(5H,m), 3.16(1H,dd,J=14.5 Hz,7.2 Hz), 3.29(1H,dd,J=14.5 Hz,6.7 Hz),3.96(3H,s),4.41–4.48 (1H,m),4.78–4.86(1H,m), 5.04–5.09(1H,m),6.60(1H,d, J=7.6 Hz),6.78(1H,d,J=7.7 Hz),7.02(1H,t,J=7.7 Hz), 7.18–7.30(4H,m),7.35(1H,d,J=7.7 Hz),7.48(1H,s), 7.62(1H,d,J=6.3 Hz),7.99(1H,d,J=8.0 Hz), 8.08(1H,d, J=7.7 Hz)

EXAMPLE 55

Synthesis of Compound 56

Compound 56 was prepared using H-DVal-OBzl·TsOH instead of H-DNle-OBzl·TsOH in the same manner described in Example 1-(2) and (3).

m.p.: 203°–207° C.

IR(KBr,cm$^{-1}$):
3328,2968,1722,1695,1530,1461,1389,1260,1170,1092, 765

High Resolution FAB-MS(m/e,($C_{29}H_{42}N_4O_8$+H)$^+$): Calcd: 575.3081, Found: 575.3066

$^1$H-NMR(300 MHz,DMSO-d$_6$,δ ppm): 0.65(3H,d,J=6.4 Hz),0.67(3H,d,J=6.4 Hz),0.85(3H,d, J=6.9 Hz),0.86(3H,d, J=6.9 Hz),0.90–1.48(3H,m), 1.31(9H,s),2.00–2.14(1H,m), 2.91(1H,dd,J=10.3 Hz, 14.7 Hz),3.12(1H,dd,J=3.0 Hz,14.7 Hz),3.85–4.00(1H,m), 3.95(3H,s),4.04(1H,dd,J=5.2 Hz,7.9 Hz),4.60–4.71 (1H,m),6.68(1H,d,J=8.1 Hz),7.23(1H,t,J=7.5 Hz), 7.31(1H,t,J=7.5 Hz),7.50(1H,s),7.69(1H,d,J=7.5 Hz), 7.80(1H,d,J=7.9 Hz),8.04(1H,d,J=7.5 Hz),8.16(1H,d, J=8.0 Hz)

EXAMPLE 56

Synthesis of Compound 57 and 58

(1) Preparation of Boc-DTrp(COOMe)Ø(CS-NH)-DNle-O$^t$Bu

Boc-DTrP(COOMe)-DNle-O$^t$Bu (300 mg, prepared in Example 21-(1)) and Lawesson's Reagent (140 mg) were suspended in toluene. The mixture was stirred at 100 ° C. under argon atmosphere for 5 h and concentrated under reduced pressure. The residue was purified by silica gel chromatography (Merck, Kieselgel 60) with chloroform/ diethyl ether=99/1 for elution to give the product (172 mg).

FAB-MS(m/e, ($C_{28}H_{41}N_3O_6S$+H)$^+$):547

(2) Preparation of Compound 57

A solution of Boc-DTrp(COOMe)Ø(CS-NH)-DNle-O$^t$Bu (100 mg, obtained in (1)) in formic acid (3 ml) was stirred at room temperature for 2 h and concentrated under reduced pressure. The residue was dissolved in DMF (2 ml), and NMM (100 µl) was added. To the mixture were added 2,6-dimethylpiperidinocarbonyl-γ MeLeu-OH (52 mg), HOBT·H$_2$O (34 mg) and EDCl·HCl (42 mg) under ice cooling. The mixture was stirred at the same temperature for 30 mim and at room temperature for 14 h. The reaction mixture was diluted with ethyl acetate, washed with sat. aq NaHCO$_3$, 1N-hydrochloric acid and water successively, dried over MgSO$_4$ and evaporated in vacuo. The residue was purified by preparative TLC (Merck, Kieselgel 60 F$_{254}$) with hexane/ethyl acetate=3/2 for development to give Compound 57 (28 mg).

m.p.: 75°–78° C.

IR(KBr,cm$^{-1}$):
3256,2956,2872,1743,1626,1518,1461,1374,1341,1311, 1257,1227,1158,1089,1041,765,747

High Resolution FAB-MS(m/e,($C_{38}H_{59}N_5O_6S$+H)$^+$): Calcd: 714.4264, Found: 714.4252

1$^1$H-NMR(300 MHz,CDCl$_3$,δ ppm): 0.82(3H,t,J=7.2 Hz),0.90(9H,s),0.95–1.92(14H,m), 1.19(3H,d,J=7.1 Hz), 1.20(3H,d,J=7.1 Hz),1.37(9H,s), 3.29(1H,dd,J=7.2 Hz,14.4

Hz),3.47(1H,dd,J=5.5 Hz, 14.4 Hz),4.00(3H,s), 4.05–4.13(1H,m),4.11–4.22(1H,m), 4.19–4.26(1H,m), 4.65(1H,d,J=7.4 Hz),4.72–4.79(1H,m), 4.97(1H,ddd,J=5.5 Hz,7.2 Hz,8.0 Hz),7.06(1H,d, J=8.0 Hz),7.26(1H,t,J=7.4 Hz),7.33(1H,t,J=7.4 Hz), 7.49(1H,s),7.72(1H,d,J=7.4 Hz), 8.15(2H,d,J=7.4 Hz)

(3) Preparation of Compound 58

Compound 57 (13 mg, prepared in (2)) was dissolved in formic acid (1 ml) under ice cooling, and the mixture was stirred at the same temperature for 1.5 h and at room temperature for 6 h. The mixture was diluted with ethyl acetate, washed with brine and water, dried over $MgSO_4$ and evaporated in vacuo. The residue was purified by silica gel chromatography (Wakogel C-200) with chloroform/methanol=97/3 for elution to give Compound 58 (7.3 mg).

m.p.: 74°–82° C.

IR(KBr,$cm^{-1}$):
3310,2956,2866,1743,1620,1572,1524,1461,1386,1341, 1260,1230,1128,1092,765,747

High Resolution FAB-MS(m/e,$(C_{34}H_{51}N_5O_6S+H)^+$): Calcd: 658.3638, Found: 658.3658

$^1$H-NMR(300 MHz,$CDCl_3$,δ ppm): 0.78(9H,s),0.86(3H, t,J=6.8 Hz),0.92–2.05(14H,m), 1.14(6H,d,J=7.1 Hz), 3.33(1H,dd,J=7.9 Hz,14.7 Hz), 3.54(1H,dd,J=5.3 Hz,14.7 Hz),3.92–4.06(2H,m),3.99 (3H,s),4.09–4.16(1H,m), 4.94–5.07(2H,m),5.17(1H,ddd, J=5.3 Hz,6.3 Hz,7.9 Hz), 6.99(1H,d,J=6.3 Hz),7.22(1H,t, J=7.8 Hz),7.31(1H,t,J= 7.8Hz),7.51(1H,s),7.64(1H,d, J=7.8 Hz),8.11(1H,d,J=7.8 Hz),8.89(1H,d,J=7.5 Hz)

EXAMPLE 57

Synthesis of Compound 59

(1) Preparation of 2-hydroxy-3-(3-indolyl)propionyl-DNle-O$^t$Bu

To a solution of DL-3-indolelactic acid (103 mg), H-DNle-O$^t$Bu·HCl (100 mg) and NMM (58 μl) in dichloromethane (5.0 ml) were added HOBT·$H_2O$ (81 mg) and EDCI·HCl (102 mg) under ice cooling. After being stirred at room temperature over night, the mixture was diluted with dichloromethane (20 ml), washed with sat. aq $NaHCO_3$, 10% aq. citric acid and brine successively, dried over $MgSO_4$ and evaporated in vacuo. The residue was purified by MPLC (Merck, LiChroprep Si 60) with hexane/ethyl acetate=3/2 for elution to give the product (80 mg).

FAB-MS(m/e, $(C_{21}H_{30}N_2O_4+H)^+$):375

(2) Preparation of 2,6-dimethylpiperidinocarbonyl-γ MeLeu-Ø(COO)-DTrp-DNle-O$^t$Bu To a solution of 2-hydroxy-3-(3-indolyl)propionyl-DNle-O$^t$Bu (62 mg, prepared in (1)) and 2,6-dimethylpiperidinocarbonyl-γMeLeu-OH (72 mg) in THF (1.5 ml) were added EDCI·HCl (48 mg) and DMAP (10 mg) under ice cooling. The mixture was stirred at room temperature for 3 d, and concentrated under reduced pressure. To the residue was added water (20 ml), and the mixture was extracted with ethyl acetate (10 ml× 3). The combined organic layers were washed with 1N-hydrochloric acid (10 ml), sat. aq. $NaHCO_3$ and brine successively, dried over $MgSO_4$ and evaporated in vacuo.

The residue was purified by MPLC (Merck, LiChroprep Si 60) with hexane/ethyl acetate=2/1 for elution to give the product (91 mg).

FAB-MS(m/e, $(C_{36}H_{56}N_4O_6+H)^+$):641

(3) Preparation of 2,6-dimethylpiperidinocarbonyl-γ MeLeu-Ø(COO)-DTrp(COOMe)-DNle-O$^t$Bu To a solution of 2,6-dimethylpiperidinocarbonyl-γ MeLeu-Ø(COO)-DTrp-DNle-O$^t$Bu (76 mg, prepared in (2)) in dichloromethane were added methyl chloroformate (14 μl), pulverized NaOH (12 mg) and TBAHS (1 mg) under ice cooling. After being stirred at room temperature for 6 h, the mixture was diluted with dichloromethane (30 ml).

The solution was washed with water (20 ml), dried over $MgSO_4$ and evaporated in vacuo. The residue was purified by preparative TLC (Merck, Kieselgel 60 $F_{254}$) with hexane/ethyl acetate=2/1 for development to give the compound (41 mg).

FAB-MS(m/e, $(C_{38}H_{58}N_4O_8+H)^+$):699

(4) Preparation of Compound 59

A solution of 2,6-dimethylpiperidinocarbonyl-γ MeLeu-Ø(COO)-DTrp(COOMe)-DNle-O$^t$Bu (36 mg, prepared in (3)) in TFA (3 ml) was stirred at room temperature for 1 h, and concentrated under reduced pressure. The residue was triturated with water to give Compound 59 (32 mg).

m.p.: 74°–79° C.

IR(KBr,$cm^{-1}$):
3406,2962,1746,1671,1629,1539,1461,1386,1260,1200, 1164,1092,765,747

FAB-MS(m/e,$(C_{34}H_{50}N_4O_8+H)^+$):643

$^1$H-NMR(300 MHz,$CDCl_3$, δ ppm): 0.83(3H,t,J=7.2 Hz), 0.89(9H,s),1.00–1.90(14H,m), 1.17(3H,d,J=7.5 Hz), 1.20(3H,d,J=7.5 Hz),3.31(1H,dd, J=7.5 Hz,14.9 Hz), 3.40(1H,dd,J=3.8 Hz,14.9 Hz),3.70–4.10 (2H,m),4.02(3H, s),4.07–4.19(1H,m),4.30–4.40 (1H,m),5.48(1H,dd,J=3.8 Hz,7.5 Hz),7.25(1H,t, J=7.5 Hz),7.34(1H,t,J=7.5 Hz), 7.48(1H,s),7.59(1H,d, J=7.5 Hz),7.20–8.00(2H,brs), 8.16(1H,d,J=7.5 Hz)

EXAMPLE 58

Synthesis of Compound 60

Compound 60 was prepared in the same manner described in Example 50.

$^1$H-NMR(300 MHz,$CDCl_3$, δ ppm): 0.82(3H,t,J=7.2 Hz), 0.89(9H,s),1.15(3H,d,J=7.1 Hz), 1.05–1.75(14H,m), 1.16(3H,d,J=7.1 Hz),1.41(9H,s), 3.17(1H,dd,J=6.2 Hz,15.0 Hz),3.37(1H,dd,J=5.9 Hz, 15.0 Hz),3.93–4.10(2H,m), 4.00(3H,s),4.10–4.23(1H,m), 4.24–4.36(1H,m),4.65(1H,d, J=7.1 Hz),4.81(1H,ddd, J=5.9 Hz,6.2 Hz,8.5 Hz),6.48(1H, d,J=8.5 Hz),7.03(1H,d, J=7.6 Hz),7.24(1H,t,J=7.6 Hz), 7.33(1H,t,J=7.6 Hz), 7.47(1H,s),7.62(1H,d,J=7.6 Hz), 8.16(1H,d,J=7.8 Hz)

EXAMPLE 59

Synthesis of Compounds 61, 62, 63 and 64

(1) Preparation of 2,6-dimethylpiperidinocarbonyl-γ MeLeu-DLmTyr-DNle-OBzl

The title compound was prepared from 2,6-dimethylpiperidinocarbonyl-γ MeLeu-OH, Boc-DLmTyr-OH and H-DNle-OBzl according to the same procedure described in Example 14.

FAB-MS(m/e, $(C_{37}H_{54}N_4O_6+H)^+$):651

(2) Preparation of Compound 61

Compound 61 was prepared by deprotection of 2,6-dimethylpiperidinocarbonyl-γMeLeu-DLmTyr-DNle-OBzl in a similar manner to that of Example 1-(3).

IR(KBr,cm$^{-1}$):
3328,2956,2872,1602,1533,1464,1404,1341,1251

FAB-MS(m/e,($C_{30}H_{48}N_4O_6$+H)$^+$):561

$^1$H-NMR(300 MHz,CDCl$_3$,δ ppm): 0.81(3H,t,J=6.1 Hz), 0.84(9H,s),1.13(6H,d,J=7.0 Hz), 1.03–1.85(14H,m), 2.80–2.99(1H,m),2.99–3.13(1H,m), 3.95–4.30(4H,m), 4.53–4.71(1H,m),6.63(1H,d,J=7.6 Hz), 6.68(1H,d,J=7.6 Hz),6.79(1H,brs),7.05(1H,t,J=7.6 Hz), 7.46(1H,brs)

(3) Preparation of Compound 62

2,6-dimethylpiperidinocarbonyl-γMeLeu-DLmTyr-DNle-OBzl (prepared in (1)) was acetylated by acetic anhydride and DMAP in THF. The product was deprotected in a similar manner to that of Example 1-(3) to afford Compound 63.

FAB-MS(m/e, ($C_{32}H_{50}N_4O_7$+H)$^+$):603

(4) Preparation of Compound 63

2,6-dimethylpiperidinocarbonyl-γMeLeu-DLmTyr-DNle-OBzl (prepared in (1)) was methylated by etherial diazomethane. The product was deprotected in a similar manner to that of Example 1-(3) to afford Compound 64.

FAB-MS(m/e, ($C_{31}H_{50}N_4O_6$+H)$^+$):575

(5) Preparation of Compound 64

2,6-dimethylpiperidinocarbonyl-γMeLeu-DLmTyr-DNle-OBzl (prepared in (1)) was methoxycarbonylated by methyl chloroformate and DMAP in THF. The product was deprotected in a similar manner to that of Example 1-(3) to afford Compound 63.

FAB-MS(m/e, ($C_{32}H_{50}N_4O_8$+H)$^+$):619

EXAMPLE 60

Synthesis of Compound 65

Compound 65 was prepared using DSer as a starting material in the same manner described in Example 6.

IR(KBr,cm$^{-1}$):
3328,2962,1743,1659,1563,1461,1386,1260,1167,1092, 1050,762

High Resolution FAB-MS(m/e,($C_{27}H_{38}N_4O_9$+H)$^+$): Calcd: 563.2717, Found: 563.2694

$^1$H-NMR(300 MHz,DMSO-d$_6$,δ ppm):
0.67(3H,d,J=6.6 Hz),0.69(3H,d,J=6.6 Hz),0.98–1.38 (3H, m),1.31(9H,s),2.93(1H,dd,J=9.7 Hz,14.6 Hz), 3.13(1H,dd, J=4.2 Hz,14.6 Hz),3.26–3.36(1H,m),3.51–3.60 (1H,m), 3.73–3.85(1H,m),3.89–4.01(1H,m),3.94 (3H,s), 4.55–4.68(1H,m),6.68(1H,d,J=8.0 Hz),7.22 (1H,t,J=7.5 Hz),7.30(1H,t,J=7.5 Hz),7.48(1H,s), 7.69(1H,d,J=7.5 Hz), 7.69(1H,d,J=7.5 Hz),8.03(1H,d, J=7.5 Hz),8.19(1H,d,J=7.5 Hz)

EXAMPLE 61

Synthesis of Compound 66

(1) Preparation of N-(2-thienylcarbamoyl)-γMeLeu-OBzl

To a solution of 2-thiophenecarboxylic acid (30 mg) and diphenylphosphoryl azide (50.5 μl) in toluene (10 ml) was added TEA (32.6 μl) under ice cooling. The mixture was stirred at the same temperature for 1 h, at room temperature for 10 h and refluxed for 6 h . The mixture was cooled to room temperature. To the mixture was added a solution of γMeLeu-OBzl·TsOH (61 mg) and TEA (21 μl) in DMF (1 ml). After being stirred at room temperature for 15 h, the reaction mixture was diluted with ethyl acetate, washed with sat. aq. NaHCO$_3$, 1N-hydrochloric acid and brine successively, dried over MgSO$_4$ and evaporated in vacuo. The residue was purified by preparative TLC (Merck, Kieselgel 60 F$_{254}$) with hexane/ethyl acetate=4/1 for development to give the product.

FAB-MS(m/e,($C_{19}H_{24}N_2O_3S$+H)$^+$):361

(2) Preparation of Compound 66

N-(2-Thienylcarbamoyl)-γMeLeu-OBzl (27.0 mg, prepared in (1)) was hydrolyzed with aqueous sodium hydroxide in methanol to afford N-(2-thienylcarbamoyl)-γMeLeu-OH (22.0 mg), which was condensed with H-DTrp(COOMe)-DNle-O$^t$Bu·HCl (35.0 mg, prepared in Example 21-(1)) in a similar manner to that of Example 33-(3) to afford Compound 66 (5.4 mg).

High Resolution FAB-MS(m/e,($C_{31}H_{41}N_5O_7S$+H)$^+$): Calcd: 628.2805, Found: 628.2822

Each compound 67.70 in the following Examples 62–65 was prepared using each corresponding amine and amino acid benzyl ester tosylate in the same manner described in Example 36.

EXAMPLE 62

Compound 67 m.p.: 98°–102° C.

IR(KBr,cm$^{-1}$):
3316,2962,2872,1743,1632,1521,1461,1386,1260,1092, 765,747

High Resolution FAB-MS(m/e,($C_{31}H_{45}N_5O_7$+H)$^+$): Calcd: 600.3397, Found: 600.3371

$^1$H-NMR(300 MHz,CDCl$_3$,δ ppm): 0.50(3H,d,J=6.7 Hz), 0.57(3H,d,J=6.7 Hz),0.86(3H,t, J=6.8 Hz),1.10(6H,d,J=5.6 Hz),0.92–2.10(11H,m), 2.84(1H,dd,J=11.2 Hz,14.4 Hz), 3.21(1H,dd,3.1 Hz, 14.4 Hz),3.67–3.90(3H,m),3.96(3H,s), 4.08–4.20(1H,m), 4.57–4.72(1H,m),5.47(1H,d,J=7.8 Hz), 7.25(1H,t, J=7.6 Hz),7.32(1H,t,J=7.6 Hz),7.52(1H,s), 7.69(1H,d, J=7.6 Hz),8.03(1H,d,J=7.6 Hz),8.31(1H,d,J=8.1 Hz), 8.35(1H,d,J=9.0 Hz)

EXAMPLE 63

Compound 68

IR(KBr,cm$^{-1}$):
2954,2859,1737,1616,1525,1442,1340,1309,1226,1199, 1126,765,748

High Resolution FAB-MS(m/e,($C_{33}H_{47}N_5O_7$+H)$^+$): Calcd: 626.3554, Found: 626.3572

$^1$H-NMR(300 MHz,DMSO-d$_6$,δ ppm): −0.80–0.95(2H, m),0.01–0.39(3H,m),0.86(3H,t, J=7.0 Hz),1.03(3H,d,J=7.4 Hz),1.05(3H,d,J=7.4 Hz), 0.98–1.82(14H,m),2.85(1H,dd,J= 10.9 Hz,14.7 Hz), 3.22(1H,dd,3.1 Hz,14.7 Hz),3.95(3H,s), 3.90–4.20 (4H,m),4.53–4.65(1H,m),6.05(1H,d,J=6.8Hz), 7.24 (1H,t,J=7.4 Hz),7.31(1H,t,J=7.4 Hz),7.49(1H,s), 7.68(1H,d,J=7.4 Hz),8.02(1H,d,J=7.4 Hz),8.24(1H,d, J=6.9 Hz),8.25(1H,d,J=8.8 Hz)

EXAMPLE 64

Compound 69 m.p.: 103°–113° C.

IR(KBr,cm$^{-1}$):
2958,2937,1737,1654,1618,1527,1477,1444,1382,1340, 1309,1259,1226,1201,1145,1126,765

High Resolution FAB-MS(m/e,$(C_{32}H_{45}N_5O_7+H)^+$): Calcd: 612.3397, Found: 612.3384

$^1$H-NMR(300 MHz,DMSO-d$_6$,δ ppm): 0.02–0.39(4H,m), 0.79–0.97(1H,m),0.84(3H,t,J=7.0 Hz), 1.04(3H,d,J=6.7 Hz),1.06(3H,d,J=6.7 Hz),1.12–1.78 (12H,m),2.85(1H,dd,J=10.9 Hz,14.7 Hz),3.21–3.37 (2H,m),3.96(3H,s), 4.02–4.21(3H,m),4.50–4.62(1H,m), 6.27(1H,d,J=5.6 Hz), 7.26(1H,t,J=7.4 Hz),7.33(1H,t, J=7.4 Hz),7.52(1H,s), 7.65(1H,d,J=7.4 Hz),8.05(1H,d, J=7.4 Hz),8.20(1H,d,J=6.8 Hz),8.21(1H,d,J=9.3 Hz)

EXAMPLE 65

Compound 70

IR(KBr,cm$^{-1}$):
2954,2861,1737,1650,1531,1444,1413,1342,1299,1224, 1091,765,746

High Resolution FAB-MS(m/e,$(C_{33}H_{47}N_5O_7+H)^+$): Calcd: 626.3554, Found: 626.3538

$^1$H-NMR(300 MHz,DMSO-d$_6$,δ ppm): 0.76–0.96(3H,m), 0.96–2.30(23H,m),2.73–2.90(1H,m), 3.00–3.61(5H,m), 3.61–3.75(1H,m),3.96(3H,s),4.03–4.20 (1H,m), 4.49–4.63(1H,m),5.97(1H,d,J=4.9 Hz),7.16–7.38 (2H,m), 7.53(1H,s),7.65(1H,d,J=7.2 Hz),8.05(1H,d, J=7.2 Hz), 8.24(1H,d,J=6.5 Hz),8.32(1H,d,J=7.7 Hz)

EXAMPLE 66

Synthesis of Compound 71

Compound 71 was prepared using DSer(Me) as a starting material in the same manner described in Example 6.

m.p.: 103°–106° C.

IR(KBr,cm$^{-1}$):
3328,2962,1743,1527,1461,1386,1344,1260,1167,1092, 1047,1023,765

High Resolution FAB-MS(m/e,$(C_{28}H_{40}N_4O_9+H)^+$): Calcd: 577.2874, Found: 577.2885

$^1$H-NMR(300 MHz,DMSO-d$_6$,δ ppm): 0.65(3H,d,J=6.3 Hz),0.67(3H,d,J=6.3 Hz),1.31(9H,s), 0.90–1.60(3H,m), 2.80–3.20(2H,m),3.27(3H,s),3.43–3.75 (2H,m), 3.83–4.02(1H,m),3.95(3H,s),4.39–4.51 (1H,m), 4.65–4.81(1H,m),6.67(1H,d,J=7.1 Hz),7.23 (1H,dt,J=1.3 Hz,7.6 Hz),7.31(1H,dt,J=1.3 Hz,7.6 Hz), 7.51(1H,s), 7.73(1H,dd,J=1.3 Hz,7.6 Hz),8.03(1H,dd, J=1.3 Hz,7.6 Hz), 8.17(1H,d,J=8.3 Hz),8.37(1H,d, J=8.3 Hz)

EXAMPLE 67

Synthesis of Compounds 72, 73, 74 and 75

(1) Preparation of 2,6-dimethylpiperidinocarbonyl-γ MeLeu-DPhe(m-NO$_2$)-DNle-O$^t$Bu The title compound was prepared from 2,6-dimethylpiperidinocarbonyl-γ MeLeu-OH, Boc-DPhe(m-NO$_2$)-OH and H-DNle-O$^t$Bu·HCl according to the same manner described in Example 14.

FAB-MS(m/e, $(C_{34}H_{55}N_5O_7+H)^+$):646

(2) Preparation of Compound 72

A solution of 2,6-dimethylpiperidinocarbonyl-γ MeLeu-DPhe(m-NO$_2$)-DNle-O$^t$Bu (34 mg, prepared in (1)) in 4N-hydrogen chloride/1,4-dioxane (3 ml) was stirred at room temperature for 2 h. The mixture was evaporated in vacuo and the residue was triturated with diethyl ether to give Compound 72 (24 mg).

IR(KBr,cm$^{-1}$):
3376,2956,2872,1725,1668,1536,1473,1452,1356,1248, 1200,1140

High Resolution FAB-MS(m/e,$(C_{30}H_{47}N_5O_7+H)^+$): Calcd: 590.3554, Found: 590.3580

$^1$H-NMR(300 MHz,CDCl$_3$,δ ppm): 0.80–1.8(17H,m), 0.87(9H,s),1.15(6H,d,J=7.0 Hz), 3.12–3.42(2H,m), 4.0–4.85(6H,m),6.88(1H,d,J=7.7 Hz), 7.06(1H,d,J=7.7 Hz), 7.46(1H,t,J=7.8 Hz),7.61–7.64 (1H,m),8.04–8.11(2H,m)

(3) Preparation of 2,6-dimethylpiperidinocarbonyl-γ MeLeu-DPhe(m-NH$_2$)-DNle-O$^t$Bu A solution of 2,6-dimethylpiperidinocarbonyl-γ MeLeu-DPhe(m-NO$_2$)-DNle-O$^t$Bu (285 mg, prepared in (1)) in 95% ethanol (10 ml) was hydrogenated over 10% Pd/C at an atmospheric pressure of hydrogen for 3 h. After removal of the catalyst by filtration, the filtrate was evaporated in vacuo to give the product (274 mg).

FAB-MS(m/e, $C_{34}H_{57}N_5O_5+H)^+$):616

(4) Preparation of Compound 73 hydrochloride

Deprotection of 2,6-dimethylpiperidinocarbonyl-γ MeLeu-DPhe(m-NH$_2$)-DNle-O$^t$Bu (31 mg, prepared in (3)) in a similar manner to that of Example 67-(2) gave Compound 73 hydrochloride (28 mg).

m.p.: 144°–148° C.

IR(KBr,cm$^{-1}$):
3400,2954,1774,1720,1655,1531,1466,1389,1246,1205, 1140,689

High Resolution FAB-MS(m/e,$(C_{30}H_{49}N_5O_8+H)^+$): Calcd: 560.3812, Found: 560.3842

$^1$H-NMR(300 MHz,DMSO-d$_6$,δ ppm): 0.80(9H,s), 0.86(3H,t,J=7.0 Hz),1.04(3H,d,J=7.2 Hz), 1.07(3H,d,J=7.2 Hz),1.12–1.81(14H,m),2.75(1H,dd, J=10.5 Hz,13.6 Hz), 3.18(1H,dd,J=3.5 Hz,13.6 Hz), 4.01–4.25(4H,m), 4.36–4.49(1H,m),6.14(1H,d,J=6.6 Hz), 7.14–7.34(4H,m), 8.14(1H,d,J=8.8 Hz),8.23(1H,d, J=7.6 Hz),10.5(3H,brs)

(5) Preparation of Compound 74

To a solution of 2,6-dimethylpiperidinocarbonyl-γ MeLeu-DPhe(m-NH$_2$)-DNle-O$^t$Bu (31 mg, prepared in (3)) in dichloromethane (1 ml) were added DMAP (10 mg) and formic pivalic anhydride (20 μl), and the mixture was stirred at room temperature for 20 h. The mixture was diluted with dichloromethane (30 ml), washed with 1N-aqueous sodium hydroxide (20 ml), 1N-hydrochloric acid (20 ml) and brine (20 ml) successively, dried over MgSO$_4$ and evaporated in vacuo. The residue was purified by preparative TLC (Merck, Kieselgel 60 F$_{254}$) with hexane/ethyl acetate=1/2 for development to give $^t$Bu ester of Compound 74 (23 mg). The product (20 mg) was deprotected in a similar manner to that of Example 67-(2) to give Compound 74 (16 mg).

m.p.: 123°–125° C.

IR(KBr,cm$^{-1}$):
3300,2953,2800,1774,1670,1614,1535,1446,1396,1369, 1248,1142,789,690

High Resolution FAB-MS(m/e,$(C_{31}H_{49}N_5O_6+H)^+$): Calcd: 588.3761, Found: 588.3759

$^1$H-NMR(300 MHz,DMSO-d$_6$,δ ppm): 0.79(9H,s), 0.86(3H,t,J=7.0 Hz),0.96–1.80(23H,m), 2.62–2.75(1H,m), 3.05–3.17(1H,m),3.83–4.49(3H,m), 6.05(1H,brs),6.95(1H, d,J=7.6 Hz),7.06–7.23(2H,m), 7.42(1H,s),8.15(1H,d,J=7.3 Hz),8.22(1H,d,J=1.7 Hz), 10.07(1H,brs)

(6) Preparation of Compound 75

To a solution of 2,6-dimethylpiperidinocarbonyl-γ MeLeu-DPhe(m-NH$_2$)-DNle-O$^t$Bu (31 mg, prepared in (3)) in dichloromethane (1 ml) were added DMAP (10 mg) and methyl chloroformate (12 µl), and the mixture was stirred at room temperature for 12 h. The mixture was diluted with dichloromethane (30 ml), washed with 1N-aqueous sodium hydroxide (20 ml), 1N-hydrochloric acid (20 ml) and brine (20 ml) successively, dried over MgSO$_4$ and evaporated in vacuo. The residue was purified by preparative TLC (Merck, Kieselgel 60 F$_{254}$) with hexane/ethyl acetate=1/1 for development to give $^t$Bu ester of Compound 75 (26 mg). The product (23 mg) was deprotected in a similar manner to that of Example 67-(2) to give Compound 75 (16 mg).

m.p.: 116°–118° C.

IR(KBr,cm$^{-1}$):
3300,2954,2858,1774,1716,1668,1614,1547,1448,1232, 1074,773

High Resolution FAB-MS(m/e,(C$_{32}$H$_{51}$N$_5$O$_7$+H)$^+$): Calcd: 618.3867, Found: 618.3865

$^1$H-NMR(300 MHz,DMSO-d$_6$,δ ppm): 0.79(9H,s), 0.86(3H,t,J=7.0 Hz),1.04(3H,d,J=6.3 Hz), 1.06(3H,d,J=6.3 Hz),0.98–1.78(14H,m),2.64(1H,dd, J=11.1Hz,13.4 Hz), 3.08(1H,dd,J=3.3 Hz,13.4 Hz),3.63 (3H,s),3.99–4.43(5H, m),6.05(1H,d,J=7.4 Hz),6.86 (1H,d,J=7.8 Hz),7.08(1H,t,J= 7.8 Hz),7.24(1H,d, J=7.8 Hz),7.30(1H,s),8.06–8.18(2H,m), 9.49(1H,s)

EXAMPLE 68

Synthesis of Compounds 76 and 77

Compounds 76 and 77 were prepared using 2,6-dimethylpiperidinocarbonyl-γMeLeu-OH as a starting material in the same manner described in Example 18.

Compound 76

High Resolution FAB-MS(m/e,(C$_{36}$H$_{56}$N$_4$O$_5$S+H)$^+$): Calcd: 657.4050, Found: 657.4042

$^1$H-NMR(300 MHz,CDCl$_3$,δ ppm): 0.84(3H,t,J=7.4 Hz), 0.89(9H,s),1.10–1.75(14H,m), 1.168(3H,d,J=7.1 Hz), 1.173(3H,d,J=7.1 Hz),1.41(9H,s), 3.37(1H,dd,J=6.4 Hz,14.6 Hz),3.48(1H,dd,J=6.6 Hz, 14.6 Hz),3.96–4.08(2H, m),4.13–4.23(1H,m),4.29 (1H,ddd,J=5.7 Hz,7.8 Hz,7.8 Hz), 4.66(1H,d,J=6.8 Hz), 4.83(1H,ddd,J=6.4 Hz,6.6 Hz,8.5 Hz), 6.53(1H,d, J=8.5 Hz),6.95(1H,d,J=7.8 Hz),7.26(1H,s), 7.30–7.40 (2H,m),7.81–7.88(2H,m)

Compound 77

IR(KBr,cm$^{-1}$):
2775,1712,1666,1531,1429,1203,1138,800,762,721

High Resolution FAB-MS(m/e,(C$_{32}$H$_{48}$N$_4$O$_5$S+H)$^+$): Calcd: 601.3423, Found: 601.3406

$^1$H-NMR(300 MHz,CD$_3$OD,δ ppm): 0.84(9H,s), 0.8–1.9(17H,m),1.16(6H,d,J=7.1 Hz),3.2–3.5 (2H,m), 4.08–4.38(4H,m),4.8–4.9(1H,m),7.28–7.41 (2H,m), 7.31(1H,s),7.83–7.90(2H,m)

EXAMPLE 69

Synthesis of Compound 78 and 79

(1) Preparation of 2,6-dimethylpiperidinocarbonyl-γ MeLeu-DTrp(OH)-DNle-O$^t$Bu

To a solution of 2,6-dimethylpiperidinocarbonyl-γ MeLeu-DTrp-DNle-O$^t$Bu (128 mg) in acetic acid (1.0 ml) was added sodium cyanoborohydride (126 mg). The mixture was stirred at room temperature for 17 h, and water (10 ml) was added to the mixture. The mixture was extracted with ethyl acetate (10 ml×3 ). The combined organic layers were washed with sat. aq. NaHCO$_3$ (3 ml), dried over MgSO$_4$ and evaporated in vacuo. The residue was purified by MPLC (Merck, LiChroprep Si 60) with hexane/ethyl acetate=1/1 for elution to give a colorless powder (58.2 mg). To a solution of the product (32.1 mg) and sodium tungstate dihydrate (3.3 mg) in methanol (1.0 ml) and water (0.3 ml) was added 30% hydrogen peroxide (51 µl). After being stirred at room temperature for 1 h, the mixture was evaporated in vacuo. The residue was purified by silica gel chromatography (Wakogel, C-200) with hexane/ethyl acetate=1/1 for elution to give the product (13.7 mg).
FAB-MS(m/e, (C$_{36}$H$_{57}$N$_5$O$_6$+H)$^+$):656

(2) Preparation of Compound 78

A solution of 2,6-dimethylpiperidinocarbonyl-γ MeLeu-DTrP(OH)-DNle-O$^t$Bu (11 mg, prepared in (1)) in formic acid (0.4 ml) was stirred at room temperature for 13 h. The mixture was concentrated under reduced pressure, and the residue was purified by preparative TLC (3M, Empore Silica Sheet) with chloroform/methanol/acetic acid=20/1/1 for development to give the product (3.4 mg).

m.p.: 165° C.(dec.)

High Resolution FAB-MS(m/e,(C$_{32}$H$_{49}$N$_5$O$_6$+H)$^+$): Calcd: 600.3761, Found: 600.3774

$^1$H-NMR(300 MHz,DMSO-d$_6$,δ ppm): 0.80(9H,s), 1.05(6H,d,J=6.8 Hz),0.80–1.80(17H,m), 2.84(1H,dd,J=9.7 Hz,14.4 Hz),3.10–3.20(1H,m),4.00–4.25 (4H,m), 4.35–4.45(1H,m),6.10(1H,d,J=7.1 Hz), 6.95(1H,t,J=7.5 Hz),7.09(1H,t,J=7.5 Hz),7.17(1H,s), 7.28(1H,d,J=7.5 Hz), 7.57(1H,d,J=7.5 Hz),8.00–8.20 (2H,m)

(3) Preparation of Compound 79

A solution of 2,6-dimethylpiperidinocarbonyl-γ MeLeu-DTrp(OH)-DNle-O$^t$Bu (11 mg, prepared in (1)) in methanol (3 ml) was treated with etherial diazomethane. The mixture was evaporated in vacuo, and the residue was purified by silica gel chromatography (Wakogel, C-200) with hexane/ ethyl acetate=3/2 for elution to give a pale yellow powder (8.2 mg). The product (7.9 mg) was dissolved in formic acid (0.4 ml) and the mixture was stirred at room temperature for 14 h. The reaction mixture was evaporated in vacuo and the residue was purified by preparative TLC (3M, Empore Silica Sheet) with chloroform/methanol=5/1 for development to give the product (4.1 mg).

m.p.: 115°–120° C.

High Resolution FAB-MS(m/e,(C$_{33}$H$_{51}$N$_5$O$_6$+H)$^+$): Calcd: 614.3917, Found: 614.3881

$^1$H-NMR(300 MHz,DMSO-d$_6$,δ ppm): 0.79(9H,s), 1.05(6H,d,J=6.6 Hz),0.80–1.80(17H,m), 2.88(1H,dd,J=9.1 Hz,14.6 Hz),3.13(1H,dd,J=4.2 Hz, 14.6 Hz),3.85–3.95(1H, m),4.10–4.25(3H,m),4.40–4.50 (1H,m),3.98(3H,s),6.11(1H, d,J=7.9 Hz),7.01(1H,t, J=7.5 Hz),7.15(1H,t,J=7.5 Hz), 7.29(1H,s),7.35(1H,d, J=7.5 Hz),7.59(1H,d,J=7.5 Hz), 7.80–7.90(1H,m),7.90–8.05 (1H,m)

EXAMPLE 70

Synthesis of Compound 80,81,82 and 83

(1) Preparation of 2,6-dimethylpiperidinocarbonyl-γ MeLeu-DTrp(7-OBzl)-DNle-O$^t$Bu To a solution of 2,6-Dimethylpiperidinocarbonyl-γ MeLeu-OH (64 mg), H-DTrp(7-OBzl)-OMe (61 mg) and HOBT·H$_2$O (35 mg) in dichloromethane (2 ml) was added EDCI·HCl (44 mg) under ice cooling. The mixture was stirred at the same temperature for 3 h and at room temperature over night. The mixture was diluted with ethyl acetate (30 ml), washed with sat. aq. NaHCO$_3$, 1N-hydrochloric acid and brine successively, dried over MgSO$_4$ and evaporated in vacuo. The residue was purified by silica gel chromatography (Merck, Kieselgel 60) with hexane/ethyl acetate=1/1 for elution to give 2,6-dimethylpiperidinocarbonyl-γMeLeu-DTrp(7-OBzl)-OMe (75 mg). The compound (73 mg) was dissolved in methanol (2.0 ml) and 1N-aqueous sodium hydroxide solution (1.0 ml) was added under ice cooling. The mixture was stirred at the same temperature for 6 h and water (30 ml) was added. The mixture was acidified with 1N-hydrochloric acid and extracted with dichloromethane (30 ml×3). The combined organic layers were dried over MgSO$_4$ and evaporated to give 2,6-dimethylpiperidinocarbonyl-γMeLeu-DTrp(7-OBzl)-OH (56 mg). To a mixture of 2,6-dimethylpiperidinocarbonyl-γ MeLeu-DTrp(7-OBzl)-OH (55 mg), H-DNle-O$^t$Bu·HCl (26 mg) and HOBT·H$_2$O (18 mg) in DMF (2 ml) were added NMM (13 μl) and EDCI·HCl (23 mg) under ice cooling. The mixture was stirred at the same temperature for 2 h and at room temperature for 3 h. Water (50 ml) was added to the mixture and the mixture was extracted with ethyl acetate (20 ml×3). The combined organic layers were washed with 10% aq. citric acid (20 ml), sat. aq. NaHCO$_3$ (20 ml) and brine (20 ml) successively, dried over MgSO$_4$ and evaporated in vacuo to give the product (72 mg).

FAB-MS(m/e, (C$_{48}$H$_{63}$N$_5$O$_6$+H)$^+$):746

(2) Preparation of Compound 80

To a solution of 2,6-dimethylpiperidinocarbonyl-γ MeLeu-DTrP(7-OBzl)-DNle-O$^t$Bu (9.8 mg, prepared in (1)) in dichloromethane (0.5 ml) were added methyl chloroformate (10 μl), pulverized sodium hydroxide (5 mg) and TBAHS (2 mg), and the mixture was stirred at room temperature for 3 h. The mixture was diluted with dichloromethane, washed with water, dried over MgSO$_4$ and evaporated in vacuo. The residue was purified by preparative TLC (Merck, Kieselgel 60 F$_{254}$) with hexane/ethyl acetate= 1/1 for development to give 2,6-dimethylpiperidinocarbonyl-γMeLeu-DTrp( 1-COOMe-7-OBzl)-DNle-O$^t$Bu (5.4 mg). A solution of 2,6-dimethylpiperidinocarbonyl-γMeLeu-DTrp( 1-COOMe-7-OBzl)-DNle-O$^t$Bu (5.1 mg, obtained above) in methanol (1 ml) was hydrogenated over 10% Pd/C (5 mg) at an atmospheric pressure of hydrogen for 1 h. After removal of the catalyst by filtration, the filtrate was evaporated in vacuo. The residue was purified by preparative TLC (Merck, Kieselgel 60 F$_{254}$) with hexane/ethyl acetate= 2/1 for elution. The product was dissolved in formic acid (1.0 ml) and the mixture was stirred at room temperature for 7 h. The reaction mixture was evaporated to give Compound 80 (1.1 mg).

High Resolution FAB-MS(m/e,(C$_{34}$H$_{51}$N$_5$O$_8$+H)$^+$): Calcd: 658.3816, Found: 658.3829

$^1$H-NMR(300 MHz,CDCl$_3$,δ ppm): 0.85(3H,t,J=7.0 Hz), 0.88(9H,s),1.14(3H,d,J=7.0 Hz), 1.15(3H,d,J=7.0 Hz), 1.07–2.13(14H,m),3.19(1H,dd, J=5.3 Hz,14.8 Hz),3.31(1H, dd,J=6.6 Hz,14.8 Hz),3.82–4.00 (2H,m),4.05(3H,s), 4.07–4.18(1H,m),4.23–4.33 (1H,m),4.73–4.83(1H,m), 4.87(1H,d,J=6.2 Hz),6.45 (1H,d,J=8.6 Hz),6.89(1H,d,J=7.3 Hz),7.03(1H,d, J=7.3 Hz),7.18(1H,t,J=7.3 Hz),7.36(1H,s), 7.78(1H,d, J=7.4 Hz),10.59(1H,s)

(3) Preparation of Compound 81

A solution of 2,6-dimethylpiperidinocarbonyl-γ MeLeu-DTrp(7-OBzl)-DNle-O$^t$Bu (60.6 mg, obtained in (1)) in methanol (5 ml) was hydrogenated over 10% Pd/C (20 mg) at an atmospheric pressure of hydrogen for 1 h.

After removal of the catalyst by filtration, the filtrate was evaporated in vacuo to give 2,6-dimethylpiperidinocarbonyl-γMeLeu-DTrp(7-OH)-DNle-O $^t$Bu(50.2 mg). A mixture of 2,6-dimethylpiperidinocarbonyl-γ MeLeu-DTrp(7-OH)-DNle-O$^t$Bu (14.4 mg, obtained above) in formic acid (1.0 ml) was stirred at room temperature for 9 h. The mixture was evaporated and the residue was purified by preparative TLC (Merck, Kieselgel 60 F$_{254}$) with chloroform/methanol/acetic acid =30/1/1 for development to give Compound 81 (7.3 mg).

High Resolution FAB-MS(m/e,(C$_{32}$H$_{49}$N$_5$O$_6$+H)$^+$): Calcd: 600.3761, Found: 600.3779

$^1$H-NMR(300 MHz,CDCl$_3$,δ ppm): 0.79(3H,brs), 0.90(9H,s),1.00–1.84(20H,m),3.03–3.20 (1H,m), 3.27–3.46(1H,m),3.90–4.30(4H,m),4.70–4.90 (1H,m), 5.11(1H,brs),6.55–7.20(7H,m),9.44(1H,brs)

(4) Preparation of Compound 82

A solution of 2,6-dimethylpiperidinocarbonyl-γ MeLeu-DTrp(7-OH)-DNle-O$^t$Bu (33.9 mg, prepared in (3)) in diethyl ether (3 ml) and methanol (1 ml) was treated with etherial diazomethane. The reaction mixture was evaporated and the residue was purified by silica gel chromatography (Merck, Kieselgel 60) with hexane/ethyl acetate=1/1 for elution to give 2,6-dimethylpiperidinocarbonyl-γ MeLeu-DTrp(7-OMe)-DNle-O$^t$Bu (27.5 mg). A mixture of 2,6-dimethylpiperidinocarbonyl-γMeLeu-DTrp( 7-OMe)-DNle-O$^t$Bu (4.8 mg) in formic acid (1.0 ml) was stirred at room temperature for 7 h. The mixture was evaporated and the residue was purified by preparative TLC (Merck, Kieselgel 60 F$_{254}$) with chloroform/methanol/ acetic acid=30/1/1 for development to give Compound 82 (3.4 mg).

High Resolution FAB-MS(m/e,(C$_{33}$H$_{51}$N$_5$O$_6$+H)$^+$): Calcd: 614.3918, Found: 614.3904

$^1$H-NMR(300 MHz,CDCl$_3$, δ ppm): 0.83(3H,t,J=7.2 Hz), 0.88(9H,s),1.12(6H,d,J=6.8 Hz), 1.00–1.92(14H,m), 3.20(1H,dd,J=5.7 Hz,14.7 Hz),3.45 (1H,dd,J=5.7 Hz,14.7 Hz),3.80–4.00(2H,m),3.94(3H,s), 4.05–4.20(1H,m), 4.20–4.32(1H,m),4.68–4.78(1H,m), 4.99(1H,brs),6.56(1H, brs),6.63(1H,d,J=7.8 Hz), 7.00(1H,t,J=7.8 Hz),7.07(1H,s), 7.21(1H,d,J=7.8 Hz), 7.55(1H,brs),8.54(1H,brs)

(5) Preparation of Compound 83

To a solution of 2,6-dimethylpiperidinocarbonyl-γ MeLeu-DTrp(7-OMe)-DNle-O$^t$Bu (17.9 mg, prepared in (3)) in dichloromethane (1.0 ml) were added methyl chloroformate (20 μl), pulverized sodium hydroxide (20 mg) and TBAHS (5 mg), and the mixture was stirred at room temperature for 3 h. The mixture was diluted with dichloromethane, washed with water, dried over MgSO$_4$ and evaporated in vacuo. The residue was purified by preparative TLC (Merck, Kieselgel 60 F$_{254}$) with hexane/ethyl acetate= 1/1 for development to give 2,6-dimethylpiperidinocarbonyl-γMeLeu-DTrp(1-COOMe- 7-OMe)-DNle-O$^t$Bu (12.4 mg). A mixture of 2,6-dimethylpiperidinocarbonyl-γMeLeu-DTrp(7-OMe)-DNle-O $^t$Bu (9.2 mg) in TFA (1 ml) was stirred at room temperature for 1 h and evaporated in vacuo. The residue was purified by preparative TLC (Merck, Kieselgel 60 F$_{254}$) with chloroform/methanol/acetic acid =30/ 1/1 for development to give Compound 83 (8.1 mg).

High Resolution FAB-MS(m/e,(C$_{35}$H$_{53}$N$_5$O$_8$+H)$^+$): Calcd: 672.3972, Found: 672.4007

$^1$H-NMR(300 MHz,CDCl$_3$,δ ppm): 0.84(3H,t,J=7.0 Hz), 0.84(9H,s),1.15(6H,d,J=6.8 Hz), 1.09–1.94(14H,m), 3.25(2H,d,J=6.4 Hz),3.89–4.04 (2H,m),3.95(3H,s),3.97(3H, s),4.11–4.22(1H,m), 4.23–4.33(1H,m),4.66–4.77(1H,m), 5.06(1H,d,J=6.1 Hz), 6.66(1H,d,J=6.5 Hz),6.86(1H,t,J=4.7 Hz),7.19(2H,d, J=4.7 Hz),7.44(1H,s),7.63(1H,d,J=7.8 Hz)

EXAMPLE 71

Synthesis of Compound 84

To a solution of Compound 40 (27 mg, prepared in Example 40) in methanol (0.5 ml) was added a solution of sodium bicarbonate (3.5 mg) in water (0.1 ml). The mixture was evaporated in vacuo and the residue was dissolved in DMF (0.5 ml). Iodomethane (0.2 ml) was added to the mixture, and the mixture was stirred at room temperature for 20 h. The mixture was evaporated in vacuo and the residue was purified by preparative TLC (Merck, Kieselgel 60 $F_{254}$) with hexane/ethyl acetate= 1 for development to give the product (11 mg).

m.p.: 80°–88° C.

IR(KBr,cm$^{-1}$):
3412,2956,1746,1656,1623,1560,1521,1461,1386,1341, 1260,1092

High Resolution FAB-MS(m/e,$(C_{35}H_{53}N_5O_7+H)^+$): Calcd: 656.4023, Found: 656.3996

$^1$H-NMR(300 MHz,CDCl$_3$,δ ppm): 0.82(3H,t,J=7.2 Hz), 0.89(9H,s),1.05–1.85(14H,m), 1.15(3H,d,J=7.1 Hz), 1.16(3H,d,J=6.8 Hz),3.17(1H,dd, J=5.7 Hz,15.0 Hz), 3.39(1H,dd,J=6.2 Hz,15.0 Hz),3.65 (3H,s),3.90–4.06(2H, m),4.06–4.20(1H,m),4.36–4.47 (1H,m),4.64(1H,d,J=6.8 Hz),4.78–4.90(1H,m),6.38 (1H,d,J=9.2 Hz),7.27(1H,brs), 7.25(1H,t,J=7.3 Hz), 7.34(1H,t,J=7.3 Hz),7.47(1H,s), 7.61(1H,d,J=7.3 Hz), 8.17(1H,d,J=7.3 Hz)

EXAMPLE 72

Synthesis of Compound 85

Compound 85 was prepared using iodoethane instead of iodomethane in the same manner described in Example 71.

m.p.: 80°–85° C.

IR(KBr,cm$^{-1}$):
3412,2950,1746,1653,1626,1533,1461,1386,1257,1194, 1089,465

High Resolution FAB-MS(m/e,$(C_{36}H_{55}N_5O_7+H)^+$): Calcd: 670.4180, Found: 670.4161

$^1$H-NMR(300 MHz,CDCl$_3$, δ ppm): 0.82(3H,t,J=7.2 Hz), 0.89(9H,s),1.05–1.85(14H,m), 1.15(3H,d,J=7.1 Hz), 1.16(3H,d,J=7.1 Hz),1.22(3H,t, J=7.3 Hz),3.17(1H,dd,J=5.8 Hz,14.7 Hz),3.38(1H,dd, J=6.1 Hz,14.7 Hz),3.90–4.05(2H, m),4.00(3H,s), 4.09(2H,dq,J=1.3 Hz,7.2 Hz),4.05–4.20(1H, m),4.35–4.45 (1H,m),4.66(1H,d,J=7.3Hz),4.75–4.88(1H, m),6.49 (1H,d,J=8.6 Hz),7.18(1H,d,J=7.3 Hz),),7.24(1H,t, J=7.3 Hz),7.33(1H,t,J=7.3 Hz),7.48(1H,s),7.61(1H,d, J=7.3 Hz),8.17(1H,d,J=8.0 Hz)

EXAMPLE 73

Synthesis of Compound 86

Compound 86 was prepared using 2-iodopropane instead of iodomethane in the same manner described in Example 71.

m.p.: 75°–80° C.

IR(KBr,cm$^{-1}$):
3400,2950,2872,1745,1656,1623,1527,1461,1386,1341, 1311,1260,1197,1146,1107,1092,765

High Resolution FAB-MS(m/e,$(C_{37}H_{57}N_5O_7+H)^+$): Calcd: 684.4337, Found: 684.4334

$^1$H-NMR(300 MHz,CDCl$_3$,δ ppm): 0.82(3H,t,J=7.2 Hz), 0.88(9H,s),1.05–1.85(14H,m), 1.15(3H,d,J=6.8 Hz), 1.16(3H,d,J=7.1 Hz),1.19(3H,d, J=6.3 Hz),1.21(3H,d,J=6.3 Hz),3.17(1H,dd,J=5.9 Hz, 14.9 Hz),3.37(1H,dd,6.4 Hz,14.9 Hz),3.90–4.05(2H,m), 4.00(3H,s),4.05–4.20(1H,m), 4.31–4.42(1H,m),4.67 (1H,d,J=6.8 Hz),4.75–4.86(1H,m), 4.94(1H,sept, J=6.3 Hz),6.49(1H,d,J=8.4 Hz),7.12(1H,d,J= 7.6 Hz), 7.24(1H,t,J=7.8 Hz),7.33(1H,t,J=7.8 Hz),7.48(1H, s), 7.62(1H,d,J=7.8 Hz),8.17(1H,d,J=7.8 Hz)

EXAMPLE 74

Synthesis of Compounds 87 and 88

To a solution of Compound 84 (94 mg, prepared in Example 71) in dry THF (1 ml) were added lithium chloride (12.3 mg), sodium borohydride (11 mg) and dry ethanol (2 ml), and the mixture was stirred at room temperature over night. The mixture was cooled with ice-water, adjusted to pH 4 by the gradual addition of 10% aq. citric acid, and concentrated in vacuo. Water (20 ml) was added to the residue, and the mixture was extracted with dichloromethane (10 ml×3). Combined organic layers were washed with brine, dried over MgSO$_4$ and evaporated in vacuo. The residue was purified by preparative TLC (Merck, Kieselgel 60 $F_{254}$ ) with ethyl acetate for development to give Compound 87 (21 mg) and Compound 88 ( 11 mg).

Compound 87

IR(KBr,cm$^{-1}$):
3400,2950,2866,1743,1653,1620,1536,1461,1386,1260, 1092,765

High Resolution FAB-MS(m/e,$(C_{34}H_{53}N_5O_6+H)^+$): Calcd: 628.4074, Found: 628.4075

$^1$H-NMR(300 MHz,CDCl$_3$,δ ppm): 0.86(3H,t,J=7.1 Hz), 0.87(9H,s),1.15(3H,d,J=6.9 Hz), 1.16(3H,d,J=6.9 Hz), 1.05–1.85(14H,m),3.22(1H,dd, J=4.9 Hz,14.8 Hz),3.45(1H, dd,J=6.1 Hz,14.8 Hz),3.45–3.65 (2H,m),3.68–3.79(1H,m), 3.79–3.98(2H,m),4.01 (3H,s),4.04–4.17(1H,m),4.65(1H,d, J=6.1 Hz),4.75–4.86 (1H,m),5.95(1H,d,J=8.8 Hz),7.16(1H, d,J=8.1 Hz),7.26 (1H,dt,J=1.3 Hz,7.8 Hz),7.36(1H,dt,J=1.3 Hz,7.8 Hz), 7.48(1H,s),7.59(1H,dd,J=1.3 Hz,7.8 Hz), 8.19(1H,dd, J=1.3 Hz,7.8 Hz)

Compound 88

IR(KBr,cm$^{-1}$):
3304,2950,2866,1743,1653,1611,1539,1461,1386,1254, 1089,1044,756

High Resolution FAB-MS(m/e,$(C_{35}H_{55}N_5O_6+H)^+$): Calcd: 642.4231, Found: 642.4227

$^1$H-NMR(300 MHz,CDCl$_3$, δ ppm): 0.85(3H,t,J=7.0 Hz), 0.87(9H,s),1.15(3H,d,J=7.1 Hz), 1.16(3H,d,J=7.1 Hz), 1.05–1.83(14H,m),1.46(3H,t, J=7.0 Hz),3.23(1H,dd,J=5.3 Hz,14.8 Hz),3.44(1H,dd, J=6.2 Hz,14.8 Hz),3.45–3.65(2H, m),3.68–3.78(1H,m), 3.78–3.98(2H,m),4.05–4.16(1H,m), 4.40–4.53(2H,m), 4.64(1H,d,J=6.1 Hz),4.73–4.85(1H,m), 5.95(1H,d, J=8.8 Hz),7.15(1H,d,J=8.1 Hz),7.25(1H,dt,J=1.2 Hz, 7.5 Hz),7.35(1H,dt,J=1.2 Hz,7.5 Hz),7.50(1H,s), 7.59(1H,dd,J=1.2 Hz,7.5 Hz),8.19(1H,dd,J=1.2 Hz,7.5 Hz)

EXAMPLE 75

Synthesis of Compounds 89 and 90

Compound 89 (ester form) and Compound 90 (deprotected form) were prepared using 2,6-dimethylpiperidine and H-Cpeg-OBzl·HCl instead of cyclopentylpropylamine and H-Leu-OBzl·TsOH in the same manner described in Example 36.

Compound 89

High Resolution FAB-MS(m/e,($C_{38}H_{57}N_5O_7$+H)$^+$): Calcd: 696.4337, Found: 696.4319

$^1$H-NMR(300 MHz,CDCl$_3$,δ ppm): 0.82(3H,t,J=7.1 Hz), 0.96–1.81(20H,m),1.17(6H,d, J=7.4 Hz),1.41(9H,s), 2.09–2.20(1H,m),3.21(1H,dd, J=5.7 Hz,14.7 Hz),3.33(1H, dd,J=6.5 Hz,14.7 Hz),3.64–3.75 (1H,m),3.90–4.05(1H,m), 4.12–4.24(1H,m),4.01 (3H,s),4.25–4.35(1H,m),4.82(1H,d, J=6.9 Hz),4.80–4.93 (1H,m),6.33(1H,d,J=9.1 Hz),7.16(1H, d,J=7.8Hz),7.25 (1H,dt,J=1.4 Hz,7.7 Hz),7.33(1H,dt,J=1.4 Hz,7.7 Hz), 7.47(1H,s),7.63(1H,dd,J=1.4 Hz,7.7 Hz), 8.16(1H,dd, J=1.4 Hz,7.7 Hz)

Compound 90

High Resolution FAB-MS(m/e,($C_{34}H_{49}N_5O_7$+H)$^+$): Calcd: 640.3710, Found: 640.3607

$^1$H-NMR(300 MHz,DMSO-d$_6$,δ ppm): 0.86(3H,t,J=6.9 Hz),1.03(3H,d,J=6.8 Hz),1.05(3H,d, J=6.8 Hz), 0.92–1.80(20H,m),1.80–1.91(1H,m),2.81 (1H,dd,J=11.6 Hz,14.6 Hz);3.30(1H,dd,J=2.6 Hz,14.6 Hz), 3.50–3.84(2H, m),3.96(3H,s),4.03–4.20(2H,m),4.50–4.62 (1H,m),6.05(1H, d,J=6.8 Hz),7.25(1H,dt,J=1.3 Hz, 7.3 Hz),7.32(1H,dt,J=1.3 Hz,7.3 Hz),7.53(1H,s),7.64 (1H,dd,J=1.3 Hz,7.3 Hz), 8.05(1H,dd,J=1.3 Hz,7.3 Hz), 8.23(1H,d,J=7.6 Hz),8.33(1H, d,J=8.8 Hz)

EXAMPLE 76

Synthesis of Compound 91

Compound 91 was prepared using H-DβAbu-O$^t$Bu instead of H-DNle-O$^t$Bu in the same manner described in Example 64.

m.p.: 122°–126° C.

High Resolution FAB-MS(m/e, ($C_{30}H_{41}N_5O_7$+H)$^+$): Calcd: 584.3085, Found: 584.3079

$^1$H-NMR(300 MHz,DMSO-d$_6$,δ ppm): 0.03–0.42(4H,m), 0.83–1.00(1H,m),1.07(3H,d,J=6.8 Hz), 1.09(3H,d,J=7.0 Hz),1.13(3H,d,J=6.6 Hz),1.33–1.82 (6H,m),2.15(1H,dd,J= 8.9 Hz,15.0 Hz),2.33–2.41(1H,m), 2.75–2.90(1H,m), 3.17–3.24(4H,m),3.96(3H,s),4.05–4.23 (1H,m), 4.34–4.46(1H,m),6.37(1H,d,J=5.6 Hz), 7.26(1H,t,J=7.1 Hz),7.34(1H,t,J=7.1 Hz),7.50(1H,s), 7.63(1H,d,J=7.1 Hz), 7.92(1H,d,J=7.1 Hz),8.05(1H,d, J=8.1 Hz),8.60(1H,d,J=8.6 Hz)

EXAMPLE 77

Synthesis of Compound 92

(1) Preparation of 2,6-dimethylpiperidinocarbonyl-γ MeLeu-DTrp(COOMe)-OH

To a solution of Boc-DTrp-OBzl (12.19 g) in dichloromethane (60 ml) were added methyl chloroformate (4.8 ml), pulverized sodium hydroxide (4.1 g) and TBAHS (9.2 g), and the mixture was stirred at room temperature for 4 h. The reaction mixture was washed with water, dried over MgSO$_4$ and evaporated in vacuo. The residue was crystallized from dichloromethane and hexane to give Boc-DTrp-(COOMe)-OBzl (12.57 g). Boc-DTrp(COOMe)-OBzl (4.52 g) was dissolved in 4N-hydrogen chloride/ 1,4-dioxane (50 ml) and the mixture was stirred at room temperature for 45 min. Ethyl ether (50 ml) was added to the mixture to complete the precipitation. The precipitate was collected by filtration and dried in vacuo to give H-DTrp(COOMe)-OBzl·HCl (3.71 g). To a suspension of H-DTrp(COOMe)-OBzl·HCl (1.94 g) in dichloromethane (50 ml) were added NMM (0.55 ml), 2,6-dimethylpiperidinocarbonyl-γMeLeu-OH (1.42 g), HOBT·H$_2$O (0.84 g) and EDCI·HCl (1.05 g) under ice cooling. The mixture was stirred at the same temperature for 2 h and at room temperature over night. The reaction mixture was washed with sat. aq NaHCO$_3$ (50 ml), 10% aq. citric acid (50 ml) and brine (50 ml) successively, dried over MgSO$_4$ and evaporated. The residue was purified by MPLC (Merck, LiChroprep Si 60) with hexane/ethyl acetate=2/1 for elution to give 2,6-dimethylpiperidinocarbonyl-γMeLeu-DTrp(COOMe)-OBzl (1.17 g). A solution of 2,6-dimethylpiperidinocarbonyl-γ MeLeu-DTrp(COOMe)-OBzl (1.10 g) in methanol (30 ml) was hydrogenated over 10% Pd/C (50 mg) at an atmospheric pressure of hydrogen for 1.5 h. After removal of the catalyst by filtration, the filtrate was evaporated in vacuo to give the product (0.93 g).

(2) Preparation of Compound 92

To a solution of 2,6-dimethylpiperidinocarbonyl-γ MeLeu-DTrp(COOMe)-OH (53 mg, prepared in (1)) and HOSu (17 mg) in DMF (1.0 ml) was added EDCI·HCl (29 mg) under ice cooling, and the mixture was stirred at the same temperature for 3.5 h. To the mixture was added a solution of glycine (11 mg) and NMM (16 μl) in water (1.0 ml). The mixture was stirred at the same temperature for 2 h and at room temperature over night. To the mixture was added 1N-hydrochloric acid (20 ml), and the mixture was extracted with dichloromethane (10 ml×3). The combined organic layers were washed with brine (10 ml), dried over MgSO$_4$ and evaporated in vacuo.

The residue was purified by preparative TLC (Merck, Kieselgel 60 F$_{254}$) with chloroform/methanol/acetic acid =20/1/1 for development to give Compound 92 (23 mg).

m.p.: 124°–127° C.

IR(KBr,cm$^{-1}$): 2960,1738,1659,1612,1531,1458,1444,1383,1259,1090, 766,748

High Resolution FAB-MS(m/e,($C_{30}H_{43}N_5O_7$+H)$^+$): Calcd: 586.3241, Found: 586.3232

$^1$H-NMR(300 MHz,CDCl$_3$,δ ppm): 0.74(9H,s),1.16(3H, d,J=0.8 Hz),1.19(3H,d,J=6.8 Hz), 1.31–1.82(8H,m), 3.14(1H,dd,J=10.0 Hz,14.8 Hz),3.49 (1H,dd,4.4 Hz,14.8 Hz),3.74(1H,dd,J=6.3 Hz,16.7 Hz), 3.90–4.14(3H,m), 3.97(3H,s),4.22(1H,dd,J=6.3 Hz, 16.7 Hz),4.77–4.93(2H, m),7.13–7.36(3H,m),7.51(1H,s), 7.57(1H,d,J=7.7 Hz), 7.87(1H,t,J=6.3 Hz),8.13(1H,d, J=7.7 Hz)

Each Compound 93–95 in the following Examples 78–80 was prepared using each corresponding amino acid instead of glycine in the same manner described in Example 77.

EXAMPLE 78

Compound 93 m.p.: 113°–116° C.

IR(KBr,cm$^{-1}$): 3300,2958,1738,1653,1539,1456,1385,1259,1092,766, 748

High Resolution FAB-MS(m/e,($C_{31}H_{45}N_5O_7$+H)$^+$): Calcd: 600.3397, Found: 600.3408

$^1$H-NMR(300 MHz,CDCl$_3$, δ ppm): 0.73(9H,s),1.17(3H, d,J=6.9 Hz),1.21(3H,d,J=6.9 Hz), 1.10–2.10(8H,m), 2.49–2.70(2H,m),3.14(1H,dd,J=9.1 Hz, 14.7 Hz),3.38(1H, dd,4.8 Hz,14.7 Hz),3.08–3.48(2H,m), 3.73–3.89(1H,m), 4.01(3H,s),3.94–4.18(2H,m),4.21–4.84 (2H,m),7.13(1H,d, J=9.3 Hz),7.24(1H,t,J=7.7 Hz), 7.31(1H,t,J=7.7 Hz), 7.46(1H,t,J=5.3 Hz),7.52(1H,s), 7.62(1H,d,J=7.7 Hz), 8.13(1H,d,J=7.7 Hz)

EXAMPLE 79

Compound 94 m.p.: 137°–141° C.

IR(KBr,cm$^{-1}$):
3400,2956,2576,1734,1653,1522,1456,1385,1259,1092, 744

High Resolution FAB-MS(m/e,($C_{39}H_{50}N_6O_7$+H)$^+$): Calcd: 715.3819, Found: 715.3815

$^1$H-NMR(300 MHz,DMSO-$d_6$,δ ppm): 0.74(9H,s), 1.03(3H,d,J=6.7 Hz),1.05(3H,d,J=6.7 Hz), 1.00–1.78(8H, m),2.75–2.92(1H,m),3.07–3.32(3H,m), 3.94(3H,s), 4.02–4.26(3H,m),4.42–4.60(2H,m),6.05 (1H,d,J=7.9 Hz), 7.00(1H,t,J=7.8 Hz),7.06(1H,t, J=7.8 Hz),7.20(1H,d,J=2.4 Hz),7.23(1H,t,J=7.8 Hz), 7.31(1H,t,J=7.8 Hz),7.33(1H,d,J= 7.8 Hz),7.51(1H,d, J=7.8 Hz),7.49(1H,s),7.65(1H,d,J=7.8 Hz),8.04(1H,d, J=7.8 Hz),8.19(1H,d,J=10.5 Hz),8.37(1H,d, J=7.6 Hz), 10.83(1H,d,J=2.4 Hz)

EXAMPLE 80

Compound 95 m.p.: 103°–108° C.

IR(KBr,cm$^{-1}$):
3300,2958,2939,1738,1653,1533,1456,1444,1383,1259, 1092,766,748

High Resolution FAB-MS(m/e,($C_{35}H_{53}N_5O_7$+H)$^+$): Calcd: 656.4023, Found: 656.4044

$^1$H-NMR(300 MHz,CDCl$_3$,δ ppm): 0.82(3H,t,J=7.0 Hz), 0.83(9H,s),1.18(3H,d,J=6.8 Hz), 1.19(3H,d,J=6.8 Hz), 1.08–1.82(14H,m),2.40(1H,dd, J=5.2 Hz,15.4 Hz),2.53(1H, dd,J=6.7 Hz,15.4 Hz),3.22 (1H,dd,J=6.8 Hz,14.9 Hz), 3.29(1H,dd,J=6.8 Hz,14.9 Hz), 3.86–4.24(4H,m),4.02(3H, s),4.67–4.79(1H,m), 6.48(1H,d,J=6.9 Hz),7.16(1H,brs), 7.21–7.40(2H,m), 7.32(1H,t,J=7.8 Hz),7.48(1H,s),7.60(1H, d,J=7.8 Hz), 8.16(1H,d,J=7.8 Hz)

EXAMPLE 81

Synthesis of Compound 96

To a solution of 2,6-dimethylpiperidinocarbonyl-γ MeLeu-DTrp(COOMe)-OH (53 mg, prepared in Example 77-(1)) and HOSu (17 mg) in DMF (1.0 ml) was added EDCI·HCl (29 mg) under ice cooling, and the mixture was stirred at the same temperature for 3.5 h. To the mixture was added a solution of aminomethanesulfonic acid (17 mg) and NMM (16 μl) in water (1.0 ml). The mixture was stirred at the same temperature for 2 h and at room temperature overnight. The mixture was purified by reverse phase MPLC (Merck,LiChroprep RP-18) with methanol/water(containing 0.1% TFA)=3/2 for elution to give the product (26 mg).

m.p.: 135°–140° C.

IR(KBr,cm$^{-1}$):
1782,1737,1666,1547,1458,1385,1259,1207,1169,1092, 1041,768

High Resolution FAB-MS(m/e,($C_{29}H_{43}N_5O_8S$+H)$^+$): Calcd: 622.2911, Found: 622.2953

$^1$H-NMR(300 MHz,DMSO-$d_6$,δ ppm): 0.73(9H,s), 1.02(3H,d,J=6.9 Hz),1.03(3H,d,J=6.9 Hz), 0.98–1.73(8H, m),2.88(1H,dd,J=10.2 Hz,15.1 Hz),3.09 (1H,dd,4.3 Hz,15.1 Hz),3.93(3H,s),3.82–4.40(5H,m), 4.59–4.69(1H,m), 5.93(1H,brs),7.22(1H,t,J=7.7 Hz), 7.30(1H,t,J=7.7 Hz), 7.52(1H,s),7.74(1H,d,J=7.7 Hz), 8.03(1H,d,J=7.7 Hz), 8.03(1H,d,J=8.0 Hz),8.44(1H,t, J=6.1 Hz)

Each Compound 97–99 in the following Examples 82–84 was prepared using each corresponding aminosulfonic acid instead of aminomethanesulfonic acid in the same manner described in Example 81.

EXAMPLE 82

Compound 97 m.p.: 115°–120° C.

IR(KBr,cm$^{-1}$):
1780,1738,1666,1549,1456,1385,1259,1209,1168,1041, 768,748

High Resolution FAB-MS(m/e,($C_{30}H_{45}N_5O_8S$+H)$^+$): Calcd: 674.2626, Found: 674.2632

$^1$H-NMR(300 MHz,DMSO-$d_6$,δ ppm): 0.73(9H,s), 1.03(3H,d,J=6.2 Hz),1.06(3H,d,J=6.2 Hz), 1.18–1.80(8H, m),2.42–2.66(2H,m),2.88(1H,dd,J=4.4 Hz, 10.6 Hz), 3.13–3.43(3H,m),3.94(3H,s),4.00–4.21(2H,m), 4.30–4.80(2H,m),6.10(1H,brs),7.23(1H,t,J=7.6 Hz), 7.32(3H,t,J=7.6 Hz),7.47(1H,s),7.84(1H,d,J=7.6 Hz), 8.04(1H,d,J=7.6 Hz),8.08(1H,t,J=5.5 Hz),8.28(1H,d, J=7.9 Hz)

EXAMPLE 83

Compound 98 m.p.: 141°–144° C.

IR(KBr,cm$^{-1}$):
3400,2958,1778,1738,1660,1539,1456,1383,1259,1153, 1092,1036,768

High Resolution FAB-MS(m/e,($C_{34}H_{53}N_5O_8S$+H)$^+$): Calcd: 692.3693, Found: 692.3713

$^1$H-NMR(300 MHz,DMSO-$d_6$,δ ppm): 0.73(9H,s), 0.83(3H,t,J=6.7 Hz),1.04(3H,d,J=6.7 Hz), 1.05(3H,d,J=6.7 Hz),0.97–2.00(14H,m),2.42–2.53 (2H,m),2.87(1H,dd,J= 10.6 Hz,15.0 Hz),3.21(1H,dd, J=3.2 Hz,15.0 Hz),3.94(3H, s),3.90–4.37(5H,m),6.10 (1H,d,J=6.6 Hz),7.24(1H,t,J=7.4 Hz),7.31(1H,t, J=7.4 Hz),7.51(1H,s),7.66(1H,d,J=7.4 Hz), 7.75(1H,d, J=8.5 Hz),8.04(1H,d,J=7.4 Hz),8.21(1H,d,J=7.7 Hz)

EXAMPLE 84

Compound 99

IR(KBr,cm$^{-1}$):
2954,2866,1778,1738,1666,1539,1477,1456,1383,1257, 1169,1092,1041,768,748,627

High Resolution FAB-MS(m/e,($C_{33}H_{51}N_5O_8S$+H)$^+$): Calcd: 678.3537, Found: 678.3507

$^1$H-NMR(300 MHz,DMSO-$d_6$,δ ppm): 0.72+0.75(9H,s), 0.80–1.96(23H,m),2.80–2.93(1H,m), 3.05–3.18(1H,m), 3.93(3H,s),3.99–4.71(5H,m),5.88+ 6.01(1H,brs),7.21(1H,t, J=8.0 Hz),7.30(1H,t,J=8.0 Hz), 7.72+7.75(1H,d×2,J=8.0 Hz) , 7.56(1H,s),7.83–8.12 (3H,m)

EXAMPLE 85

Synthesis of Compound 100

To a solution of 2,6-dimethylpiperidinocarbonyl-γ-MeLeu-DTrp(COOMe)-OH (106 mg, prepared in Example 77-(1)), diethyl (R)-1-aminopentylphosphonate (67 mg) and HOBT·H$_2$O (51 mg) in dichloromethane (10 ml) was added EDCI·HCl (73 mg) under ice cooling, and the mixture was stirred at room temperature for 16 h. The mixture was diluted with ethyl acetate, washed with 10% aq. citric acid, water, sat. aq. NaHCO$_3$ and brine successively, dried over MgSO$_4$ and evaporated in vacuo.

The residue was purified by silica gel chromatography (Merck,Kieselgel 60) with hexane/ethyl acetate=1/1 for elution to give the diethyl ester of Compound 100 (61 mg). To a solution of the diethyl ester (41 mg) in dichloromethane (0.8 ml) was added bromotrimethylsilane (0.8 ml) under ice cooling. The mixture was stirred at room temperature for 4 h, and concentrated in vacuo. The residue was dissolved in 90% acetone/water (5 ml). The mixture was stirred at 45 min and evaporated in vacuo. The residue was triturated with water to give Compound 100 (25 mg).

m.p.: 205°–210° C.

IR(KBr,cm$^{-1}$): 2954,2949,1736,1649,1524,1458,1383,1259,1092,768

High Resolution FAB-MS(m/e,(C$_{33}$H$_{52}$N$_5$O$_8$P+H)$^+$): Calcd: 678.3632, Found: 678.3674

$^1$H-NMR(300 MHz,CD$_3$OD,δ ppm): 0.82(9H,s),0.92(3H,t,J=6.8 Hz),1.13(3H,d,J=6.8Hz), 1.14(3H,d,J=6.8 Hz), 1.20–2.00(14H,m),3.0–3.1(1H,m), 3.3–3.4(1H,m),4.01(3H,s),4.05–4.30(4H,m),4.7–4.8 (1H,m),7.25(1H,t,J=7.3 Hz), 7.31(1H,t,J=7.3 Hz), 7.53(1H,s),7.67(1H,d,J=7.3 Hz), 8.12(1H,d,J=7.3 Hz)

EXAMPLE 86

Synthesis of Compound 101

To a solution of Compound 40 (32 mg, prepared in Example 40), 2-aminoethanol (4 mg) and HOBT·H$_2$O (10 mg) was added EDCI·HCl (13 mg) under ice cooling. The mixture was stirred at the same temperature for 1 h and at room temperature over night. The mixture was diluted with ethyl acetate (20 ml), washed with sat. aq. NaHCO$_3$ (20 ml), 10% aq. citric acid (20 ml) and brine successively,dried over MgSO$_4$ and evaporated in vacuo. The residue was purified by preparative TLC (Merck, Kieselgel 60 F$_{254}$) with chloroform/methanol=30/1 for development to give the product (23.5 mg).

m.p.: 106°–109° C.

IR(KBr,cm$^{-1}$): 1736,1655,1610,1524,1458,1383,1257,1088,1257,1088, 766

High Resolution FAB-MS(m/e,(C$_{36}$H$_{56}$N$_6$O$_7$+H)$^+$): Calcd: 685.4289, Found: 685.4280

$^1$H-NMR(300 MHz,CDCl$_3$, δ ppm): 0.78(9H,s),0.84(3H,t,J=7.1 Hz),1.13(6H,d,J=7.1 Hz), 1.04–1.79(13H,m), 2.00–2.15(1H,m),3.22–3.43(4H,m), 3.55–3.80(3H,m), 3.82–4.17(2H,m),4.04(3H,s),4.44–4.56 (2H,m), 4.59–4.71(1H,m),4.68(1H,d,J=4.7 Hz), 6.31(1H,d,J=6.8 Hz),6.75(1H,t,J=4.3 Hz),7.28(1H,t, J=7.8 Hz),7.38(1H,t,J=7.8 Hz),7.52(1H,s),7.59(1H,d, J=7.8 Hz),7.73(1H,d,J=9.0 Hz),8.20(1H,d,J=7.8 Hz)

EXAMPLE 87

Synthesis of Compound 102

Compound 102 was prepared by deprotection of 2,6-dimethylpiperidinocarbonyl-γMeLeu-DTrp-DNle-O$^t$Bu with formic acid.

m.p.: 149°–153° C.

IR(KBr,cm$^{-1}$): 3309,2947,1653,1522,1387,743

High Resolution FAB-MS(m/e,(C$_{32}$H$_{49}$N$_5$O$_5$+H)$^+$): Calcd: 584.3812, Found: 584.3788

$^1$H-NMR(300 MHz,CD$_3$OD, δ ppm): 0.8–1.9(17H,m), 0.85(9H,s),1.13(3H,d,J=7.1 Hz), 1.15(3H,d,J=7.1 Hz), 3.2–3.4(2H,m),4.0–4.4(4H,m), 4.7–4.8(1H,m),6.97(1H,t,J= 7.9 Hz),7.05(1H,t, J=7.9 Hz),7.08(1H,s),7.29(1H,d,J=7.9 Hz),7.59(1H,d, J=7.9 Hz)

EXAMPLE 88

Synthesis of Compound 103

Dry hydrogen chloride gas was bubbled into a solution of Compound 102 (70 mg) in formic acid (3 ml), and the mixture was stirred at room temperature for 2.5 h. The mixture was evaporated in vacuo and the residue was purified by preparative TLC (Merck,Kieselgel 60 F$_{254}$) with chloroform/methanol=10/1 for elution to give the product (45 mg).

m.p.: 132°–135° C.

IR(KBr,cm$^{-1}$): 2954,1716,1653,1608,1522,1458,1387,795,750

High Resolution FAB-MS(m/e,(C$_{33}$H$_{49}$N$_5$O$_6$+H)$^+$): Calcd: 612.3761, Found: 612.3746

$^1$H-NMR(300 MHz,DMSO-d$_6$,δ ppm): 0.75(9H,s), 0.78–0.89(3H,m),1.01(3H,d,J=6.8Hz), 1.02(3H,d,J=6.8 Hz),1.05–1.8(14H,m),2.85–3.00(1H,m), 3.2–3.5(2H,m), 3.95–4.20(4H,m),4.5–4.6(1H,m),6.03–6.09 (1H,m), 7.26–7.36(2H,m),7.51–7.62(1H,m),7.69 (1H,d,J=7.6 Hz), 7.95–8.25(2.5H,m),9.18(0.5H,brs)

EXAMPLE 89

Synthesis of Compound 104

To a solution of Compound 81 (7.3 mg, prepared in Example 70) in dichloromethane (0.5 ml) were added acetyl chloride (1.3 μl) and DMAP (3.7 mg) under ice cooling. The mixture was stirred at the same temperature for 4 h and at room temperature for 2 h. Ethyl acetate (20 ml) was added to the mixture, and the mixture was washed with 1N-hydrochloric acid (20 ml) and brine (20 ml), dried over MgSO$_4$ and evaporated in vacuo.

The residue was purified by preparative TLC (Merck, Kieselgel 60 F$_{254}$) with chloroform/methanol/acetic acid =20/1/1 for elution to give the product (2.2 mg).

High Resolution FAB-MS(m/e,(C$_{34}$H$_{51}$N$_5$O$_7$+H)$^+$): Calcd: 642.3867, Found: 642.3851

$^1$H-NMR(300 MHz,CDCl$_3$,δ ppm): 0.83(3H,t,J=7.0 Hz), 0.88(9H,s),1.14(6H,d,J=5.8 Hz), 1.07–1.87(13H,m), 2.12–2.42(1H,m),2.38(3H,s),3.18 (1H,dd,J=6.0 Hz,14.4 Hz),3.40(1H,dd,J=6.0 Hz,14.4 Hz), 3.93–4.30(4H,m), 4.68–4.80(1H,m),4.95(1H,d,J=6.0 Hz), 6.70(1H,d,J=6.5 Hz),6.96(1H,d,J=7.6 Hz),7.06(1H,t, J=7.6 Hz),7.06(1H,s), 7.31(1H,d,J=6.5 Hz),7.49(1H,d, J=7.6 Hz),8.62(1H,s)

EXAMPLE 90

Synthesis of Compound 105

To a solution of 2,6-dimethylpiperidinocarbonyl-γ MeLeu-DTrp(COOMe)-OH (20 mg) and NMM (4.2 μl) in dry THF (2.0 ml) was added isopropyl chloroformate (5.3 μl) at −25° C. over 5 min. To the mixture was added a solution of (R)-5-(1-aminopentyl)-1H-tetrazole hydrochloride (10.9 mg) and NMM (6.3 μl) in dry THF (2.0 ml) at −20° C. The mixture was stirred at −20° C.—15° C. for 2 h and at 10° C. for 10 h, then concentrated under reduced pressure. The residue was partitioned between ethyl acetate (10 ml) and water (10 ml). The organic layer was washed with 1N-hydrochloric acid (10 ml×2) and water (10 ml), dried over anhydrous sodium sulfate and evaporated in vacuo. The residue was purified by preparative TLC (Merck, Kieselgel 60 $F_{254}$) with chloroform/methanol=20/1 for development to give the product (13.5 mg).

m.p.: 111°–116° C.

IR(KBr,cm$^{-1}$):
3400,3300,2942,2870,1659,1612,1529,1456,1383,1259, 1091,766,748

High Resolution FAB-MS(m/e,$(C_{34}H_{51}N_9O_5+H)^+$): Calcd: 666.4092, Found: 666.4113

$^1$H-NMR(300 MHz,CDCl$_3$,δ ppm): 0.83(9H,s),0.88(3H, d,J=6.7 Hz),0.98(3H,t,J=6.7 Hz), 0.99(3H,d,J=6.7 Hz), 1.08–1.90(13H,m),2.16–2.30 (1H,m),3.30–3.48(2H,m), 3.54(1H,quint,J=6.7 Hz), 3.61–3.82(2H,m),4.05(3H,s), 4.62–4.73(1H,m),4.66 (1H,d,J=6.0 Hz),5.44(1H,dt,J=3.9 Hz,9.7 Hz),6.32(1H,d, J=6.6 Hz),7.30(1H,t,J=7.4 Hz), 7.40(1H,t,J=7.4 Hz), 7.54(1H,s),7.61(1H,d,J=7.4 Hz), 7.94(1H,d,J=9.7 Hz), 8.20(1H,d,J=7.4 Hz)

Each Compound 106 and 107 in the following Examples 91 and 92 was prepared using 2,6-dimethylpiperidino-carbonyl-Val-DTrp(COOMe)-OH and each corresponding aminosulfonic acid as starting materials in the same manner described in Example 81.

EXAMPLE 91

Compound 106

IR(KBr,cm$^{-1}$):
3290,2960,2935,1738,1668,1610,1522,1458,1383,1259, 1201,1092,768,748

FAB-MS(m/e,$(C_{31}H_{47}N_5O_8+H)^+$):650

$^1$H-NMR(300 MHz,CD$_3$OD,δ ppm): 0.52(3H,d,J=6.8 Hz),0.77(3H,d,J=6.8 Hz),0.80–1.00 (3H,m),1.17+1.19(3H× 2,d×2,J=6.6 Hz),1.10–1.85 (13H,m),2.96(1H,dd,J=11.2 Hz,14.6 Hz),3.30–4.50 (5H,m),4.01(3H,s),4.75(1H,dd,J=3.9 Hz,11.2 Hz), 7.22–7.34(2H,m),7.54(1H,s),7.67(1H,d,J=7.2 Hz), 8.10(1H,d,J=8.1 Hz)

EXAMPLE 92

Compound 107 m.p.: 128°–131° C.

IR(KBr,cm$^{-1}$):
3273,2960,1778,1736,1662,1541,1456,1382,1259,1201, 1039,768,748

High Resolution FAB-MS(m/e,$(C_{32}H_{49}N_5O_8S+H)^+$): Calcd: 664.3380, Found: 664.3437

$^1$H-NMR(300 MHz,DMSO-d$_6$,δ ppm): 0.51(3H,d,J=6.4 Hz),0.65(3H,d,J=6.4 Hz),0.83(3H,t, J=7.0 Hz),1.07(6H,d,J= 6.5 Hz),1.01–2.00(13H,m),2.40–2.55 (2H,m),2.83(1H,dd,J= 11.0 Hz,14.5 Hz),2.23(1H,dd, J=3.0 Hz,14.5 Hz), 3.69–3.83(1H,m),3.95(3H,s),3.97–4.23 (3H,m), 4.35–4.48(1H,m),5.95(1H,brs),7.25(1H,t, J=7.5 Hz), 7.32(1H,t,J=7.5 Hz),7.51(1H,s),7.66(1H,d, J=7.5 Hz), 7.81(1H,d,J=8.3 Hz),8.03(1H,d,J=7.5 Hz), 8.34(1H,d,J=8.1 Hz)

Each Compound 108 and 109 in the following Examples 93 and 94 was prepared using 2,6-dimethylpiperidino-carbonyl-Leu-DTrp(COOMe)-OH and each corresponding aminosulfonic acid as starting materials in the same manner described in Example 81.

EXAMPLE 93

Compound 108 m.p.: 139°–142° C.

IR(KBr,cm$^{-1}$):
3271,2956,2871,1774,1736,1655,1543,1458,1383,1259, 1092,1039,768

High Resolution FAB-MS(m/e,$(C_{33}H_{51}N_5O_8S+H)^+$): Calcd: 678.3537, Found: 678.3585

$^1$H-NMR(300 MHz,DMSO-d$_6$,δ ppm): 0.67(3H,d,J=5.6 Hz),0.71(3H,d,J=5.6 Hz),0.83(3H,t, J=6.8 Hz),1.04(3H,d,J= 6.7 Hz),1.05(3H,d,J=6.7 Hz), 1.10–2.00(15H,m), 2.45–2.65(2H,m),2.85(1H,dd, J=10.8 Hz,14.5 Hz),3.22(1H, dd,J=3.4 Hz,14.5 Hz), 3.95(3H,s),3.95–4.45(5H,m), 6.07(1H,brs), 7.24(1H,t,J=7.6 Hz),7.32(1H,t,J=7.6 Hz), 7.47(1H,s), 7.66(1H,d,J=7.6 Hz),7.78(1H,d,J=8.5 Hz), 8.04(1H,d, J=7.6 Hz),8.21(1H,d,J=7.8 Hz)

EXAMPLE 94

Compound 109

IR(KBr,cm$^{-1}$):
3271,2956,2872,1738,1668,1610,1539,1456,1385,1259, 1203,1092,1041,768

High Resolution FAB-MS(m/e,$(C_{32}H_{49}N_5O_8S+Na)^+$): Calcd: 686.3187, Found: 686.3200

$^1$H-NMR(300 MHz,DMSO-d$_6$,δ ppm): 0.57–0.89(9H,m), 0.95–1.10(6H,m),1.10–1.97(15H,m), 2.78–2.93(1H,m), 3.09–3.31(1H,m),3.94+3.95(3H,s×2), 4.00–4.75(5H,m), 5.85+6.10(1H,brs×2),7.18+7.54 (1H,brs×2),7.20–7.36(2H, m),7.46+7.55(1H,s×2), 7.64+7.76(1H,d×2,J=7.3 Hz),8.03+ 8.05(1H,d×2, J=7.3 Hz),7.95+8.33(1H,d×2,J=9.5 Hz,8.8 Hz)

EXAMPLE 95

Synthesis of Compound 110

(1) Preparation of 2,6-dimethylpiperidinocarbonyl-γ MeLeu-DTrp(2-Br)-DNle-O$^t$Bu To a solution of 2,6-dimethylpiperidinocarbonyl-γ MeLeu-DTrp-DNle-O$^t$Bu (320 mg) in anhydrous acetic acid (1.0 ml) was added dropwise over 10 min a solution of N-bromosuccinimide (107 mg) in anhydrous acetic acid (3.0 ml). After being stirred at room temperature for 20 h, the mixture was diluted with dichloromethane (50 ml) and the solution was washed with water (25 ml×2), sat. aq. NaHCO$_3$ (25 ml) and sat. brine successively, dried over MgSO$_4$ and evaporated in vacuo. The residue was purified by preparative TLC (Merck, Kieselgel 60 $F_{254}$) with chloroform/methanol= 30/1 for development to give the product (15 mg).

FAB-MS (m/e, $(C_{36}H_{56}BrN_5O_5+H)^+$): 718 and 720

(2) Preparation of Compound 110

A solution of 2,6-dimethylpiperidinocarbonyl-γ MeLeu-DTrp(2-Br)-DNle-O$^t$Bu (14 mg, prepared in (1)) in TFA (1.0 ml) was stirred under ice cooling for 3 h. The mixture was concentrated under reduced pressure and the residue was purified by preparative TLC (Merck, Kieselgel 60 $F_{254}$) with chloroform/methanol/acetic acid =30/1/1 for development to give Compound 110 (8.4 mg).

m.p.: 145°–148° C.

IR(KBr,cm$^{-1}$):
2954,2868,1724,1659,1620,1514,1247,1136,743

High Resolution FAB-MS(m/e,$(C_{32}H_{48}BrN_5O_5+H)^+$): Calcd: 662.2917, Found: 662.2944

$^1$H-NMR(300 MHz,CDCl$_3$, a ppm): 0.78(3H,t,J=7.1 Hz), 0.91(9H,s),1.13(3H,d,J=7.1 Hz), 1.16(3H,d,J=7.1 Hz), 0.98–1.86(14H,m),3.19(1H,dd, J=6.2 Hz,14.6 Hz),3.39(1H, dd,5.7 Hz,14.6 Hz),3.93–4.20 (3H,m),4.20–4.35(1H,m), 4.50–4.66(1H,m),4.90–5.07 (1H,m),6.54–6.66(1H,m), 7.09(1H,t,J=7.6 Hz),7.15 (1H,t,J=7.6 Hz),7.25(1H,d,J=7.6 Hz),7.62(1H,d, J=7.6 Hz),7.30–7.44(1H,m),8.74(1H,brs)

EXAMPLE 96

Synthesis of Compound 111

(1) Preparation of α-N,1-bis-t-butoxycarbonyl-α-N-trifluoroacetyl- 2-chloro-D-tryptophan methyl ester To a solution of α-N-trifluoroacetyl-2-chloro-D-tryptophan methyl ester (283 mg) in acetonitrile (5 ml) were added di-tert-butyl dicarbonate and DMAP (20 mg) and the mixture was stirred at room temperature for 23 h. The mixture was evaporated in vacuo and the residue was purified by MPLC (Merck, LicChroprep Si 60) with hexane/ethyl acetate=5/1 for elution to give the product (265 mg).

FAB-MS (m/e, $(C_{24}H_{28}F_3ClN_2O_7)^+$): 548 and 550

(2) Preparation of α-N,1-bis-t-butoxycarbonyl-2-chloro-D-tryptophan

To a solution of α-N,1-bis-t-butoxycarbonyl-α-N-trifluoroacetyl- 2-chloro-D-tryptophan methyl ester (255 mg, prepared in (1)) in methanol (5 ml) was added 1N NaOH (1.03 ml) and the mixture was stirred at room temperature for 7 h. The mixture was diluted with water (50 ml), acidified with 10% citric acid aq. solution and the mixture was extracted with ethyl acetate (30 ml×3). Combined organic extracts were washed with sat. brine (30 ml), dried over MgSO$_4$ and evaporated in vacuo to give the product (206 mg).

FAB-MS (m/e, $(C_{21}H_{27}ClN_2O_6)^+$): 438 and 440

(3) Preparation of Boc-DTrp(1-Boc,2-Cl)-DNle-O$^t$Bu

To a solution of α-N,1-bis-t-butoxycarbonyl-2-chloro-D-tryptophan (206 mg, prepared in (2)) and H-DNle-O$^t$Bu·HCl (125 mg) in dichloromethane (10 ml) were added NMM (62 μl), HOBT·H$_2$O (86 mg) and EDCI·HCl (107 mg) under ice cooling. The mixture was stirred at the same temperature for 1 h and at room temperature for 3 h. The mixture was diluted with dichloromethane (20 ml), washed with sat. aq. NaHCO$_3$ (10 ml), 10% citric acid aq. solution (10 ml) and sat. brine (10 ml) successively, dried over MgSO$_4$ and evaporated in vacuo.

The residue was purified by silica gel chromatography (Merck, Kieselgel 60) with hexane/ethyl acetate=5/1 for elution to give the product (235 mg).

FAB-MS (m/e, $(C_{31}H_{46}ClN_3O_7+H)^+$): 608 and 610

(4) Preparation of H-DTrp(1-Boc,2-Cl)-DNle-O$^t$Bu

A solution of Boc-DTrp(1-Boc,2-Cl)-DNle-O$^t$Bu (252 mg, prepared in (3)) in formic acid (10 ml) was stirred at room temperature for 1 h. The mixture was concentrated under reduced pressure and the residue was dissolved in ethyl acetate (50 ml). The solution was washed with sat. aq. NaHCO$_3$ (50 ml×2) and sat. brine (50 ml) successively, dried over MgSO$_4$ and evaporated in vacuo. The residue was purified by preparative TLC (Merck, Kieselgel 60 $F_{254}$) with chloroform/methanol= 30/1 for development to give the product (98 mg).

FAB-MS (m/e, $(C_{26}H_{38}ClN_3O_5+H)^+$): 508 and 510

(5) Preparation of 2,6-dimethylpiperidinocarbonyl-γ MeLeu-DTrp(1-Boc,2-Cl)-DNle-O$^t$Bu To a solution of H-DTrp(1-Boc,2-Cl)-DNle-O$^t$Bu (39 mg, prepared in (4)) and 2,6-dimethylpiperidinocarbonyl-γ MeLeu-OH (34 mg) in dichloromethane (3 ml) were added HOBT·H$_2$O (18 mg) and EDCI·HCl (23 mg) under ice cooling.

The mixture was stirred at the same temperature for 1 h and at room temperature for 3 h. The mixture was diluted with dichloromethane (30 ml), washed with sat. aq. NaHCO$_3$ (20 ml), 10% citric acid aq. solution (20 ml) and sat. brine successively, dried over MgSO$_4$ and evaporated in vacuo. The residue was purified by preparative TLC (Merck, Kieselgel 60 $F_{254}$) with hexane/ethyl acetate=2/1 for development to give the product (51 mg).

FAB-MS (m/e, $(C_{41}H_{64}ClN_5O_7+H)^+$): 774 and 776

(6) Preparation of Compound 111

A mixture of 2,6-dimethylpiperidinocarbonyl-γ MeLeu-DTrp(1-Boc,2-Cl)-DNle-O$^t$Bu (12.3 mg, prepared in (5)) in TFA (1.0 ml) was stirred at room temperature for 1 h and concentrated in vacuo. The residue was purified by preparative TLC (Merck, Kieselgel 60 $F_{254}$) with chloroform/methanol/acetic acid=30/1/1 for development to give Compound 111 (7.4 mg).

m.p.: 145°–149° C.

IR(KBr,cm$^{-1}$):
3290,2956,2360,1646,1618,1533,1247,1128,743

High Resolution FAB-MS(m/e,$(C_{32}H_{48}ClN_5O_5+H)^+$): Calcd: 618.3422, Found: 618.3431

$^1$H-NMR(300 MHz,CDCl$_3$, δ ppm): 0.78(3H,t,J=7.2 Hz), 0.91(9H,s),1.13(3H,d,J=6.9 Hz), 1.16(3H,d,J=6.9 Hz), 0.96–1.88(14H,m),3.20(1H,dd, J=5.7 Hz,15.0 Hz),3.39(1H, dd,5.7 Hz,15.0 Hz),3.90–4.08 (2H,m),4.08–4.20(1H,m), 4.20–4.33(1H,m),4.48–4.64 (1H,m),4.90–5.05(1H,m), 6.49–6.63(1H,m),7.10(1H,t, J=8.0 Hz),7.17(1H,t,J=8.0 Hz), 7.25(1H,d,J=8.0 Hz), 7.59(1H,d,J=8.0 Hz),7.33–7.48(1H, m),8.61(1H,brs)

Each Compound 112 and 113 in the following Examples 97 and 98 was prepared using 2,6-dimethylpiperidinocarbonyl-Leu-OH or hexahydroazepinylcarbonyl-Leu-OH respectively instead of 2,6-dimethylpiperidinocarbonyl-γ MeLeu-OH in Example 96-(5) in the same manner described in Example 96-(5) and (6).

EXAMPLE 97

Compound 112 m.p.: 142°–147° C.

IR(KBr,cm$^{-1}$):
3402,2956,2870,2360,1653,1622,1522,1387,1340,1238, 1128,743

High Resolution FAB-MS(m/e,$(C_{31}H_{46}ClN_5O_5+H)^+$): Calcd: 604.3266, Found: 604.3260

¹H-NMR(300 MHz,CDCl₃, δ ppm): 0.79(3H,t,J=7.2 Hz), 0.86(3H,d,J=4.9 Hz),0.88(3H,d, J=4.9 Hz),1.15(3H,d,J=6.9 Hz),1.16(3H,d,J=6.9 Hz), 0.93–1.87(15H,m),3.21(1H,dd,J= 6.3 Hz,14.4 Hz), 3.38(1H,dd,6.3 Hz,14.4 Hz),3.91–4.07(2H, m),4.07–4.20 (1H,m),4.20–4.34(1H,m),4.52–4.73(1H,m), 4.82–5.02 (1H,m),6.52–6.70(1H,m),7.11(1H,t,J=7.1 Hz),7.17 (1H,t,J=7.1 Hz),7.26(1H,d,J=7.1 Hz),7.59(1H,d, J=7.1 Hz),7.31–7.49(1H,m),8.63(1H,brs)

EXAMPLE 98

Compound 113 m.p.: 127°–130° C.

IR(KBr,cm⁻¹):
3300,2929,2864,1647,1529,1452,1342,1217,743

High Resolution FAB-MS(m/e,($C_{30}H_{44}ClN_5O_5$+H)⁺): Calcd: 590.3109, Found: 590.3067

¹H-NMR(300 MHz,CDCl₃, δ ppm): 0.78(3H,t,J=7.2 Hz), 0.86(3H,d,J=4.4 Hz),0.88(3H,d,J= 4.4 Hz),0.92–1.87(17H, m),3.05–3.47(6H,m),3.92–4.06 (1H,m),4.23–4.38(1H,m), 4.51–4.70(1H,m),4.92–5.08 (1H,m),6.50–6.70(1H,m), 7.11(1H,t,J=7.6 Hz),7.17 (1H,t,J=7.6 Hz),7.26(1H,d,J=7.6 Hz),7.59(1H,d,J= 7.6 Hz),7.37–7.52(1H,m),8.60(1H,brs)

EXAMPLE 99

Synthesis of Compound 114

(1) Preparation of α-N-trifluoroacetyl-2-chloro-1-methyl-D-tryptophan

To a solution of α-N-trifluoroacetyl-2-chloro-1-methyl-D-tryptophan methyl ester (525 mg) in methanol (10 ml) was added 1N NaOH (1.70 ml) and the mixture was stirred at room temperature for 6 h. The mixture was diluted with water (50 ml), acidified with 1N HCl and the mixture was extracted with diethyl ether (30 ml×3). Combined organic extracts were washed with sat. brine (30 ml), dried over MgSO₄ and evaporated in vacuo. The residue was recrystallized from ethyl acetate-hexane to give the product (344 mg).

FAB-MS (m/e, ($C_{14}H_{12}ClF_3N_2O_3$+H)⁺): 449 and 451

(2) Preparation of α-N-trifluoroacetyl-DTrp(1-Me,2-Cl)-DNle-O^tBu

To a solution of α-N-trifluoroacetyl-2-chloro-1-methyl-D-tryptophan (340 mg, prepared in (1)) and H-DNle-O^tBu·HCl (230 mg) in dichloromethane (20 ml) were added NMM (0.12 ml), HOBT·H₂O (180 mg) and EDCI·HCl (225 mg) under ice cooling. The mixture was stirred at the same temperature for 1 h and at room temperature over night. The mixture was diluted with ethyl acetate (100 ml), washed with sat. aq. NaHCO₃ (100 ml), 1N HCl (100 ml) and sat. brine (100 ml) successively, dried over MgSO₄ and evaporated in vacuo. The residue was purified by silica gel chromatography (Merck, Kieselgel 60) with hexane/ethyl acetate=4/1 for elution to give the product (571 mg).

(3) Preparation of H-DTrp(1-Me,2-Cl)-DNle-O^tBu

To a solution of α-N-trifluoroacetyl-DTrp(1-Me, 2-Cl)-DNle-O^tBu (84 mg, prepared in (2)) in 1,4-dioxane (10 ml) was added 1M Na₂CO₃ aq. solution (3.0 ml) and the mixture was stirred at 50° C. over night. The mixture was diluted with water (30 ml) and extracted with ethyl acetate (10 ml×3). Combined organic extracts were washed with sat. brine, dried over MgSO₄ and evaporated in vacuo. The residue was purified by preparative TLC (Merck, Kieselgel 60 F₂₅₄) with hexane/ethyl acetate=3/7 for development to give the product (47 mg).

FAB-MS (m/e, ($C_{22}H_{32}ClN_3O_3$+H)⁺): 422 and 424

(4) Preparation of 2,6-dimethylpiperidinocarbonyl-γ MeLeu-DTrp(1-Me,2-Cl)-DNle-O^tBu To a solution of H-DTrp(1-Me,2-Cl)-DNle-O^tBu (47 mg, prepared in (3)) and 2,6-dimethylpiperidinocarbonyl-γ MeLeu-OH (38 mg) in DMF (2.0 ml) were added HOBT·H₂O (22 mg) and EDCI·HCl (27 mg) under ice cooling. The mixture was stirred at the same temperature for 30 min and at room temperature for 1.5 h. The mixture was concentrated in vacuo and the residue was dissolved in ethyl acetate. The solution was washed with sat. aq. NaHCO₃, 1N HCl and sat. brine successively, dried over MgSO₄ and evaporated in vacuo. The residue was purified by preparative TLC (Merck, Kieselgel 60 F₂₅₄) with hexane/ethyl acetate= 1/1 for development to give the product (73 mg).

FAB-MS (m/e, ($C_{37}H_{58}ClN_5O_5$+H)⁺): 688 and 690

(5) Preparation of Compound 114

A solution of 2,6-dimethylpiperidinocarbonyl-γ MeLeu-DTrP(1-Me,2-Cl)-DNle-O^tBu (28 mg, prepared in (4)) in TFA (3 ml) was stirred at room temperature for 1 h and concentrated in vacuo. The residue was purified by preparative TLC (Merck, Kieselgel 60 F₂₅₄) with chloroform/methanol=9/1 for development to give Compound 114 (19 mg).

m.p.: 103°–108° C.

IR(KBr,cm⁻¹):
3300,2954,2937,1652,1647,1541,1533,1522,741

High Resolution FAB-MS(m/e,($C_{33}H_{50}ClN_5O_5$+H)⁺): Calcd: 632.3578, Found: 632.3564

¹H-NMR(300 MHz,CDCl₃, δ ppm): 0.78(3H,t,J=7.4 Hz), 0.86(9H,s),1.14(3H,d,J=5.8 Hz), 1.15(3H,d,J=5.8 Hz), 0.91–1.92(14H,m),3.34(1H,dd,J= 5.7 Hz,14.6 Hz),3.44(1H, dd,6.2 Hz,14.6 Hz),3.73(3H,s), 3.84–4.19(3H,m),4.30(1H, ddd,J=5.7 Hz,6.2 Hz,7.6 Hz), 4.66–4.74(1H,m),4.90(1H,d, J=5.5 Hz),6.41(1H,d,J=7.6 Hz),7.11(1H,t,J=7.8 Hz), 7.22(1H,t,J=7.8 Hz),7.25(1H, d,J=7.8 Hz),7.58(1H,d,J=7.8 Hz),7.62(1H,d,J=6.9 Hz)

EXAMPLE 100

Synthesis of Compound 115

To a solution of 2,6-dimethylpiperidinocarbonyl-γ MeLeu-DTrp-DNle-O^tBu (199 mg) in acetic acid (2 ml) was added methanesulfenyl chloride and the mixture was stirred at room temperature for 2 days. The mixture was concentrated under reduced pressure and the residue was purified by preparative TLC (Merck, Kieselgel 60 F₂₅₄) with chloroform/methanol=10/1 for development to give Compound 115 (65 mg).

m.p.: 158°–161° C.

IR(KBr,cm⁻¹):
3305,2954,2869,1652,1618,1521,1448,1386,1247,744

High Resolution FAB-MS(m/e,($C_{33}H_{51}N_5O_5S$+H)⁺): Calcd: 630.3689, Found: 630.3663

¹H-NMR(300 MHz,aceton-d₆, δ ppm): 0.80–1.90(23H, m),0.83(9H,s),2.47(3H,s),3.27(1H,dd, J=8.9 Hz,14.2 Hz), 3.51(1H,dd,4.4 Hz,14.2 Hz),4.00–4.15 (1H,m), 4.15–4.35(3H,m),4.69–4.77(1H,m),5.65(1H,d, J=8.4 Hz), 7.02(1H,t,J=7.6 Hz),7.10(1H,t,J=7.6 Hz), 7.31(1H,d,J=7.6 Hz),7.40–7.43(1H,m),7.69(1H,d,J=7.6 Hz),7.75(1H,d,J=6.6 Hz),10.37(1H,s)

EXAMPLE 101

Synthesis of Compound 116

To a solution of Compound 115 (50 mg, prepared in Example 100) in acetic acid (2 ml) was added 30% hydrogen peroxide (13.6 μl) and the mixture was stirred at room temperature for 2 h. The mixture was concentrated under reduced pressure and the residue was purified by preparative TLC (Merck, Kieselgel 60 $F_{254}$) with chloroform/methanol/acetic acid=10/1/1 for development to give Compound 116 (18.9 mg).

m.p.: 161°–168° C.

IR(KBr,cm$^{-1}$):
3390,2956,1652,1603,1538,1405,1128,746

High Resolution FAB-MS(m/e,$(C_{33}H_{52}N_5O_6S+H)^+$):

Calcd: 646.3638, Found: 646.3663

$^1$H-NMR(300 MHz,acetone-$d_6$-CD$_3$OD,dppm):
0.80–1.90(23H,m),0.82+0.87(9H,s×2),3.06(3H,s),
3.15–3.65(2H,m),4.05–4.40(4H,m),4.62–4.78(1H,m),
7.12(1H,t,J=7.5 Hz),7.26(1H,t,J=7.5 Hz),7.46(1H,d, J=7.5 Hz),7.81–7.89(1H,m)

EXAMPLE 102

Synthesis of Compound 117

To a solution of Compound 116 (23 mg, prepared in Example 101) in acetic acid (1 ml) was added 30% hydrogen peroxide (41 μl) and the mixture was stirred at room temperature for 4 h. The mixture was concentrated under reduced pressure and the residue was purified by preparative TLC (Merck, Kieselgel 60 $F_{254}$) with chloroform/methanol=10/1 for development to give Compound 117 (4 mg).

FAB-MS (m/e, $(C_{33}H_{51}N_5O_7S-H)^-$): 660

$^1$H-NMR(300 MHz,acetone-$d_6$, δ ppm): 0.80(9H, s)0.84–1.86(23H,m),3.34(3H,s)3.50–3.65 (1H,m),3.78(1H, dd,J=4.3 Hz,14.3 Hz),3.90–4.04(1H,m), 4.15–4.32(3H,m), 4.65–4.75(1H,m),5.64(1H,d,J= 6.5 Hz),7.19(1H,t,J=7.4 Hz),7.36(1H,t,J=7.4 Hz), 7.55(1H,d,J=7.4 Hz),7.71(1H,brs), 7.87(1H,d,J= 7.4 Hz),7.97(1H,d,J=8.0 Hz),10.95(1H,brs)

REFERENTIAL EXAMPLE 1

Synthesis of (R)-2-Aminohexanesulfonic acid (1) Preparation of (R)-2-t-butoxycarbonylamino-1-hexanol To a solution of Boc-DNle-OMe (4.23 g) in dry THF (30 ml) were added lithium chloride (0.85 g), sodium borohydride (0.76 g) and dry ethanol (60 ml), and the mixture was stirred at the same temperature for 2 h and at room temperature over night. The mixture was with ice-water, adjusted to pH 3 by the gradual addition of 10% aq. citric acid, and concentrated in vacuo. Water (200 ml) was added to the residue,and the mixture was extracted with dichloromethane (50 ml×3).

The combined organic layers were washed with brine, dried over MgSO$_4$ and evaporated in vacuo. The residue was purified by silica gel chromatography (Merck, Kieselgel 60 ) with hexane/ethyl acetate=1/1 for elution to give the product (2.95 mg).

(2) Preparation of (R)-2-t-butoxycarbonylamino-1-hexyl methanesulfonate.

To a solution of (R)-2-t-butoxycarbonylamino-1-hexanol (2.17 g, prepared in (1)) in dichloromethane (20 ml) were added triethylamine (1.67 ml) and methanesulfonyl chloride (0.93 ml) under ice cooling. After being stirred at the same temperature for 1 h, the mixture was washed with water, 10% aq. citric acid, sat. aq NaHCO$_3$ and brine successively, dried over MgSO$_4$ and evaporated in vacuo. The residue was purified by silica gel chromatography (Merck, Kieselgel 60) with hexane/ethyl acetate=2/1 for elution to give the product (1.32 g).

(3) Preparation of (R)-2-aminohexanesulfonic acid

A mixture of (R)-2-t-butoxycarbonylamino-1-hexyl methanesulfonate (428 mg, prepared in (1)) in 4N-hydrogen chloride/1,4-dioxane (10 ml) was stirred at room temperature for 1 h, and evaporated in vacuo. The residue was dissolved in water (3.0 ml) and sodium sulfite (378 mg) was added. After being stirred at room temperature for 4 d, the reaction mixture was passed through a Dowex 50W-X8 column (H$^+$ form) and washed with excess water. The combined water solution was concentrated in vacuo to give the product (114 mg).

FAB-MS(m/e, $(C_6H_{15}NO_3S+H)^+$):182

REFERENTIAL EXAMPLE 2

Synthesis of (R)-3-Aminoheptanoic acid (1) Preparation of (R)-2-t-butoxycarbonylaminoheptanenitrile A mixture of (R)-2-t-butoxycarbonylamino-1-hexyl methanesulfonate (561 mg, prepared in Referential Example 1-(2)) and sodium cyanide (117 mg) in DMF (3 ml) was stirred at 60° C. for 5 h. After cooling, water (50 ml) was added to the mixture. The mixture was extracted with dichloromethane (25 ml×3). Combined organic layers were washed with brine, dried over MgSO$_4$ and evaporated in vacuo. The residue was purified by silica gel chromatography (Merck,Kieselgel 60) with hexane/ethyl acetate=3/1 for elution to give the product (327 mg).

(2) Preparation of (R)-3-aminoheptanoic Acid

A mixture of (R)-2-t-butoxycarbonylaminoheptanenitrile (165 mg, prepared in (1)) in 6N-hydrochloric acid (10 ml) was refluxed for 3 h. After cooling, the mixture was evaporated in vacuo. The residue was dissolved in methanol (2 ml) and propylene oxide (1 ml) was added to the mixture. After being stirred at room temperature over night, the mixture was evaporated in vacuo. The residue was crystallized from methanol and diethyl ether to give the product (52 mg).

FAB-MS(m/e, $(C_7H_{15}NO_2+H)^+$):146

We claim:

1. A peptide of the formula:

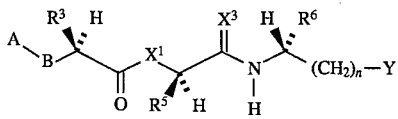

wherein

A is a group of the formula $R^{12}R^{13}N-C(=O)-$, wherein $R^{12}$ and $R^{13}$ form, together with the adjacent nitrogen atom, a 5- to 9-membered nitrogen-containing saturated heterocyclic ring having four to eight carbon atoms, and wherein one to four hydrogen atoms on the carbon atoms of the saturated heterocyclic ring may independently be replaced by a lower alkyl group;

B is a group of the formula —$NR^2$—, wherein $R^2$ is a hydrogen atom or a lower alkyl group;

$R^3$ is a lower alkyl group;

$X^1$ is a group of the formula —$NR^4$—, wherein $R^4$ is a hydrogen atom or a lower alkyl group;

$R^5$ is a 3-indolylmethyl group, wherein the indole ring is substituted at the 2-position by a substituent selected from the group consisting of a lower alkylthio group, a lower alkylsulfinyl group and a lower alkylsulfonyl group;

$X^3$ is an oxygen atom;

$R^6$ is a hydrogen atom or a lower alkyl group;

n is 0 or 1;

Y is a group of the formula $CO_2R^{71}$ wherein $R^{71}$ is a hydrogen atom or a lower alkyl group; or a pharmaceutically acceptable salt thereof.

2. The peptide of claim 1, wherein said indolylmethyl group is substituted at the 2-position with a lower alkylthio group.

3. The peptide of claim 1, wherein said indolylmethyl group is substituted at the 2-position with a lower alkysulfinyl group.

4. The peptide of claim 1, wherein said indolylmethyl group is substituted at the 2-position with a lower alkylsulfonyl group.

5. A vasodilator or bronchodilator pharmaceutical composition, comprising the peptide of claim 1 or a pharmaceutically acceptable salt thereof and a pharmaceutically acceptable carrier.

6. A method of alleviating bronchoconstriction in a mammal comprising administering to said mammal a peptide of claim 1 or a pharmaceutically acceptable salt thereof in an amount effective to alleviate said bronchoconstriction.

* * * * *